(12) United States Patent
Schroit et al.

(10) Patent No.: US 7,329,642 B2
(45) Date of Patent: Feb. 12, 2008

(54) β-2-GLYCOPROTEIN IS AN INHIBITOR OF ANGIOGENESIS

(75) Inventors: Alan Jay Schroit, Bellaire, TX (US); Krishnakumar Balasubramanian, Pearland, TX (US); Marya McCarty, Houston, TX (US)

(73) Assignee: Board of Regents, University of Texas System, Austin, TX (US)

( * ) Notice: Subject to any disclaimer, the term of this patent is extended or adjusted under 35 U.S.C. 154(b) by 644 days.

(21) Appl. No.: 10/406,158

(22) Filed: Apr. 2, 2003

(65) Prior Publication Data

US 2003/0219406 A1    Nov. 27, 2003

Related U.S. Application Data

(60) Provisional application No. 60/381,219, filed on May 17, 2002.

(51) Int. Cl.
    *A61K 38/00*    (2006.01)
(52) U.S. Cl. ............................................. 514/8
(58) Field of Classification Search ................ None
    See application file for complete search history.

(56) References Cited

U.S. PATENT DOCUMENTS

| | | | |
|---|---|---|---|
| 5,981,471 A | 11/1999 | Papathanassiu | 514/2 |
| 6,300,308 B1 | 10/2001 | Schroit | 514/8 |
| 6,312,694 B1 | 11/2001 | Thorpe et al. | 424/178.1 |
| 6,593,291 B1 | 7/2003 | Green | 514/2 |
| 6,734,163 B2 | 5/2004 | Papathanassiu | 514/2 |
| 6,946,439 B2 | 9/2005 | Hembrough | 514/2 |
| 2002/0025321 A1* | 2/2002 | Shoenfeld et al. | 424/184.1 |

FOREIGN PATENT DOCUMENTS

| | | |
|---|---|---|
| WO | WO97/43311 | 11/1997 |
| WO | WO 99/33522 | 7/1999 |
| WO | WO 00/04052 | 1/2000 |
| WO | WO 00/54801 | 9/2000 |
| WO | WO 01/19868 | 3/2001 |
| WO | WO 01/027079 | 4/2001 |
| WO | WO 02/053092 | 7/2002 |

OTHER PUBLICATIONS

Barry, B.W. Breaching the skin's barrier to drugs, Nature Biotechnology 2004, vol. 22, No. 2, 165-167.*
Alsabti and Muneir, "Serum Proteins in Breast Cancer," *Japan J. Exp. Med.* 49(4):235-240 (1979).
Adams, et al., "Roles of EphrinB Ligands and EphB Receptors in Cardiovascular Development: Demarcation of Arterial/Venous Domains, Vascular Morphogenesis, and Sprouting Angiogenesis," *Genes & Development* 13:295-306 (1999).

(Continued)

*Primary Examiner*—Misook Yu
(74) *Attorney, Agent, or Firm*—Vinson & Elkins L.L.P

(57) ABSTRACT

The present disclosure provides a method of inhibiting angiogenesis within a tissue of interest by providing either intact or nicked β2-Glycoprotein 1 (β2GP1) to cells associated with the tissue. The presence of β2GP1 inhibits angiogenesis within the tissue, in part by preventing neovascularization into the tissue. The disclosure also provides a method for treating tumors by providing β2GP1 to the tumor.

44 Claims, 11 Drawing Sheets

OTHER PUBLICATIONS

Akiba, et al., "Transforming Growth Factor-α Stimulates Prostaglandin Generation Through Cytosolic Phospholipase $A_2$ Under the Control of p11 in Rat Gastric Epithelial Cells," *British Journal of Pharmacology* 131(5):1004-1010 (2000).

Aoyama, et al., "The Primary Structure of Rat $\beta_2$-Glycoprotein I," *Nucleic Acids Research* 17(15):6401 (1989).

Asherson and Cervera, "Antiphospholipid Syndrome," *Journal of Investigative Dermatology* 100(1):21S-27S (1993).

Balasubramanian, et al., "Immune Clearance of Phosphatidylserine-Expressing Cells by Phagocytes—The Role of $\beta_2$-Glycoprotein I in Macrophage Recognition," *The Journal of Biological Chemistry* 272(49):31113-31117 (1997).

Balasubramanian and Schroit, "Characterization of Phosphatidylserine-Dependent $\beta_2$-Glycoprotein I Macrophage Interactions," *The Journal of Biological Chemistry* 273(44):29272-29277 (1998).

Balasubramanian, et al., "Binding of Annexin V to Membrane Products of Lipid Peroxidation," *Biochemistry* 40:8672-8676 (2001).

Bellagamba, et al., "Tryosine Phosphorylation of Annexin II Tetramer Is Stimulated by Membrane Building," *The Journal of Biological Chemistry* 272(6):3195-3199 (1997).

Bevers, et al., "Lupus Anticoagulant IgG's (LA) Are Not Directed to Phospholipids only, but to a Complex of Lipid-Bound Human Prothrombin," *THrombosis and Haemostasis*, 66(6):629-632 (1991).

Blank, et al., "Prevention of Experimental Antiphospholipid Syndrome and Endothelial Cell Activation by Synthetic Peptides," *Proc. Natl. Acad. Sci. USA* 96:5164-5168 (1999).

Borchman, et al., "Interactions and Molecular Structure of Cardiolipin and $\beta_2$-Glycoprotein 1 ($\beta_2$-GP1)," *Clin. Exp. Immunol.* 102:373-378 (1995).

Brighton, et al., "Beta$_2$-Glycoprotein I in Thrombosis: Evidence for a Role as a Natural Anticoagulant," *British Journal of Haematology* 93:185-194 (1996).

Bouma, et al., "Adhesion Mechanism of Human $\beta_2$-Glycoprotein I to Phospholipids Based on its Crystal Structure," *The EMBO Journal* 18(19):5166-5174 (1999).

Burri and Djonov, "Intussusceptive Angiogenesis—The Alternative to Capillary Sprouting," *Molecular Aspects of Medicine* 23:S1-S27 (2002).

Carmeliet and Jain, "Antiogenesis in Cancer and Other Diseases," *Nature* 407:249-257 (2000).

Chang, et al., "Mosaic Blood Vessels in Tumors: Frequency of Cancer Cells in Contact with Flowing Blood," *PNAS* 97(26):14608-14613 (2000).

Chen, et al., "Cloning and Expression of $\beta_2$-Glycoprotein 1 Recognized by Antiphospholipid Antibodies and its Clinical Investigation," *Chinese Medical Journal* 112(1):67-71 (1999).

Chen, et al., "Identification of the Enzymatic Mechanism of Nitroglycerin Bioactivation," *PNAS* 99(12):8306-8311 (2002).

Chiang, et al., "Specific Down-Regulation of Annexin II Expression in Human Cells Interferes with Cell Proliferation," *Molecular and Cellular Biochemistry* 199:139-147 (1999).

Connor and Schroit, "Transbilayer Movement of Phosphatidylserine in Nonhuman Erythrocytes: Evidence That the Aminophospholipid Transporter Is a Ubiquitous Membrane Protein," *Biochemistry* 28:9680-9685 (1989).

Connor, et al., "Bidirectional Transbilayer Movement of Phospholipid Analogs in Human Red Blood Cells," *The Journal of Biological Chemistry* 267(27):19412-19417 (1992).

Cozzolino, et al., "Interleukin 1 Is an Autocrine Regulator of Human Endothelial Cell Growth," *Proc. Natl. Acad. Sci. USA* 87:6487-6491 (1990).

Davis, et al., "Isolation of Angiopoietin-1, a Ligand for the TIE2 Receptor, by Secretion-Trap Expression Cloning," *Cell* 87:1161-1169 (1996).

Day, et al., "Molecular Cloning and Sequence Analysis of the cDNA Encoding Human Apolipoprotein H ($\beta_2$-Glycoprotein I)," *Int. J. Clin. Lab. Res.* 21:256-263 (1992).

Del Papa, et al., "Endothelial Cells as Target for Antiphospholipid Antibodies," *Arthritis & Rheumatism* 40(3):551-561 (1997).

Del Papa, et al., "Human $\beta_2$-Glycoprotein I Binds to Endothelial Cells Through a Cluster of Lysine Residues That Are Critical for Anionic Phospholipid Binding and Offers Epitopes for Anti-$\beta_2$-Glycoprotein I Antibodies," *The Journal of Immunology* 160:5572-5578 (1998).

Del Papa, et al., "Relationship between anti-phospholipid and anti-endothelial cell antibodies III: β2 glycoprotein I mediates the antibody binding to endothelial membranes and induces the expression of adhesion molecules," *Clinical and Experimental Rheumatology* 13: 179-185, 1995.

Dome, et al., "Vascularization of Cutaneous Melanoma Involves Vessel Co-Option and Has Clinical Significance," *Journal of Pathology* 197:355-362 (2002).

Dreier, et al., "Differential Expression of Annexins, I II and IV in Human Tissues: An Immunohistochemical Study," *Histochem. Cell Biol.* 110:137-148 (1998).

Dvorak, et al., "Vascular Permeability Factor/Vascular Endothelial Growth Factor and the Significance of Microvascular Hyperpermeability in Angiogenesis," 237:97-132 (1999).

Ellis and Fidler, "Angiogenesis and Metastasis," *European Journal of Cancer* 32A(14):2451-2460 (1996).

Erlebacher, et al., "Toward a Molecular Understanding of Skeletal Development," *Cell* 80:371-378 (1995).

Ferrara, "Role of Vascular Endothelial Growth Factor in the Regulation of Angiogenesis," *Kidney International* 56:794-814 (1999).

Ferrara, "Vascular Endothelial Growth Factor: Molecular and Biological Aspects," 237:1-30 (1999).

Folkman, "How Is Blood Vessel Growth Regulated in Normal and Neoplastic Tissue?—G.H.A. Clowes Memorial Award Lecture," *Cancer Research* 46:467-473 (1986).

Folkman and Klagsbrun, "Angiogenic Factors," *Science* 235:442-446 (1987).

Folkman and Shing, "Angiogenesis," *The Journal of Biological Chemistry* 267(16):10931-10934 (1992).

Folkman, "Angiogenesis in Cancer, Vascular, Rheumatoid and Other Disease," *Nature Medicine* 1(1):27-31 (1995).

Folkman, "Tumor Angiogenesis," *The Molecular Basis of Cancer* Ch. 10, pp. 206-232 (1995).

Friesel, et al., "Inhibition of Endothelial Cell Proliferation," *The Journal of Cell Biology* 104:689-696 (1987).

Galli, et al., "Anticardiolipin Antibodies (ACA) Directed Not to Cardiolipin but to a Plasma Protein Cofactor," *The Lancet* 335:1544-1547 (1990).

Genvresse, et al., "Case Report—Arterial Thrombosis Associated with Anticardiolipin and Anti-$\beta_2$Glycoprotein-I Antibodies in Patients with Non-Hodgkin's Lymphoma: A Report of Two Cases," *European Journal of Haematology* 65:344-347 (2000).

George, et al., "Differential Effects of Anti-$\beta_2$ -Glycoprotein I Antibodies on Endothelial Cells and on the Manifestations of Experimental Antiphospholipid Syndrome," 97:900-906 (1998).

George, et al., "Immunolocalization of $\beta_2$-Glycoprotein I (Apolipoprotein H) to Human Atherosclerotic Plaques—Potential Implications for Lesion Progression," 99:2227-2230 (1999).

Goldsmith, et al., "Inhibition of Prothrombin Activation by Antiphospholipid Antibodies and $\beta_2$-Glycoprotein I," *British Journal of Haematology* 87:548-554 (1994).

Good, et al., "A Tumor Suppressor-Dependent Inhibitor of Angiogenesis is Immunologically and Functionally Indistinguishable From a Fragment of Thrombospondin," *Proc. Natl. Acad. Sci. USA* 87:6624-6628 (1990).

Hagihara, et al., "Role of the N- and C-Terminal Domains of Bovine $\beta_2$-Glycoprotein I in Its Interaction with Cardiolipin," *J. Biochem.* 118(1):129-136 (1995).

Hagihara, et al., "Structure and function of $\beta_2$-glycoprotein I: with special reference to the interaction with phospholipid," *Lupus* 4: S3-S5 (1995).

Hagihara, et al., "Structure and Function of the Recombinant Fifth Domain of Human $\beta_2$-Glycoprotein I: Effects of Specific Cleavage between Lys77 and Thr78," *J. Biochem.* 121:128-137 (1997).

Hajjar, et al., "Interaction of the Fibrinolytic Receptor, Annexin II, with the Endothelial Cell Surface," *The Journal of Biological Chemistry* 271(35):21652-21659 (1996).

Holash, et al., "Vessel Cooption, Regression, and Growth in Tumors Mediated by Angiopoietins and VEGF," *Science* 284:1994-1998 (1999).

Hong, et al., "Flexible Loop of $\beta_2$-Glycoprotein I Domain V Specifically Interacts with Hydrophobic Ligands," *Biochemistry* 40:8092-8100 (2001).

Horbach, et al., "$\beta_2$-Glycoprotein I Is Proteolytically Cleaved *In Vivo* upon Activation of Fibrinolysis," *Thromb Haemost* 81:87-95 (1999).

Hoshino, et al., "Identification of the Phospholipid-Binding Side of Human $\beta_2$-Glycoprotein I Domain V by Heteronuclear Magnetic Resonance," *J. Mol. Biol.* 304:927-939 (1998).

Hunt, et al., "Identification of a Region of $\beta_2$-Glycoprotein I Critical for Lipid Binding and Anti-Cardolipin Antibody Cofactor Activity," *Proc. Natl. Acad. Sci. USA* 90:2141-2145 (1993).

Hunt and Krilis, "The Fifth Domain of $\beta_2$-Glycoprotein I Contains a Phospholipid Binding Site (Cys281-Cy288) and a Region Recognized by Anticardiolipin Antibodies," *Journal of Immunology* 152:653-659 (1994).

Ingber, et al., "Synthetic Analogues of Fumagillin That Inhibit Angiogenesis and Suppress Tumour Growth," *Nature* 348:555-557 (1990).

Itoh, et al., "Highly Increased Plasma Concentrations of the Nicked Form of $\beta_2$ Glycoprotein I in Patients with Leukemia and with Lupus Anticoagulant: Measurement with a Monoclonal Antibody Specific for a Nickel Form of Domain V," *J. Biochem.* 128:1017-1024 (2000).

Iverson, et al., "Anti-$\beta_2$ Glycoprotein I ($\beta$2GPI) Autoantibodies Recognize and Epitope on the First Domain of $\beta$2GPI," *Proc. Natl. Acad. Sci. USA* 95:15542-15546 (1998).

Kandiah, et al., $\beta_2$ -glycoprotein I: Target antigen for autoantibodies in the 'antiphospholipid syndrome' , *Lupus* 5:381-385 (1996).

Khanna, et al., "Purification and Characterization of Annexin Proteins from Bovine Lung," *Biochemistry* 29:4852-4862 (1990).

Klærke, et al., "Identification of $\beta_2$-Glycoprotein I as a Membrane-Associated Protein in Kidney: Purification by Calmodulin Affinity Chromatography," *Biochimica et Biophysica Acta* 1339:203-216 (1997).

Koike, "Antiphospholipid Antibodies in Arterial Thrombosis," *The Finnish Medical Society Duodecim, Ann Med* 32(1):27-31 (2000).

Kouts, et al., "Expression of Human Recombinant $\beta_2$-Glycoprotein I with Anticardiolipin Antibody Cofactor Activity," *Federation of European Biochemical Societies* 326(1,2,3):105-108 (1993).

Kristensen, et al., "Molecular Cloning and Mammalian Expression of Human $\beta_2$-Glycoprotein I cDNA," *Federation of European Biochemical Societies* 289(2) 183-186 (1991).

Krogh, "A contribution to the physiology of the capillaries," Presentation Speech, The Novel Prize in Physiology or Medicine, (1920).

Larsson, et al., "A Novel Anti-Angiogenic Form of Antithrombin with Retained Proteinase Binding Ability and Heparin Affinity," *The Journal of Biological Chemistry* 276(15):11996-12002 (2001).

Lee, et al., "$\beta_2$-Glycoprotein I-Dependent Alterations in Membrane Properties," *Biochimica et Biophysica Acta* 1509:475-484 (2000).

Li and Eriksson, "Novel VEGF Family Members: VEGF-B, VEGF-C and VEGF-D," *The International Journal of Biochemistry & Cell Biology* 33:421-426 (2001).

Lozier, et al., "Complete Amino Acid Sequence of Human Plasma $\beta_2$-Glyocprotein I," *Proc. Natl. Acad. Sci. USA* 81:3640-3644 (1984).

Ma, et al., "High Affinity Binding of $\beta_2$-Glycoprotein I to Human Endothelial Cells Is Mediated by Annexin II," *The Journal of Biological Chemistry* 275(20):15541-15548 (2000).

Mackworth-Young, "Antiphospholipid Antibodies: More Than Just a Disease Marker?" *Immunology Today* 11(2):60-65 (1990).

Maione, et al., "Inhibition of Angiogenesis by Recombinant Human Platelet Factor-4 and Related Peptides," *Science* 247:77-79 (1990).

Matsuda, et al., "Inhibitory Activity of Anti-$\beta_2$-Glycoprotein I Antibody on Factor Va Degradation by Activated-Protein C and Its Cofactor Protein S," *American Journal of Hematology* 49:89-91 (1995).

Matsuura, et al., "Molecular Definition of Human $\beta_2$-Glycoprotein I ($\beta_2$-GPI) by cDNA Cloning and Inter-Species Differences of $\beta_2$-GPI in Alternation of Anticardiolipin Binding," *International Immunology* 3(12):1217-1221 (1991).

Matsuura, et al., "Proteolytic Cleavage of $\beta_2$-Glycoprotein I: Reduction of Antigenicity and the Structural Relationship," *International Immunology* 12(8):1183-1192 (2000).

McNeil, Patrick, et al., "Anti-phospholipid antibodies are directed against a complex antigen that includes a lipid-binding inhibitor of coagulation: $\beta_2$-Glyprotein I (apolipoprotein H)," *Proc. Natl. Acad. Sci. USA*, 87:4120-4124 (1990).

Mehdi, et al., "Nucleotide Sequence and Expression of the Human Gene Encoding Apolipoprotein H ($\beta$2-Glycoprotein I)," *Gene* 108:293-298 (1991).

Miyato, et al., "Phosphatidylserine Induces Apoptosis in CHO Cells Without Mitochondrial Dysfunction in a Manner Dependent on Caspases Other Than Caspases-1, -3, -8 and -9," *Federation of European Biochemical Societies* 504:73-77 (2001).

Moestrup, et al., "$\beta_2$-Glycoprotein-1 (Apolipoprotein H) and $\beta_2$-Glycoprotein-I—Phospholipid Complex Harbor a Recognition Site for the Endocytic Receptor Megalin," *J. Clin. Invest.* 102(5):902-909 (1998).

Mori, et al., "$\beta_2$-Glycoprotein I Modulates the Anticoagulant Activity of Activated Protein C on the Phospholipid Surface," *Thrombosis and Haemostasis* 75(1):49-55 (1996).

Müller, et al., "Inhibitory Action of Transforming Growth Factor $\beta$ on Endothelial Cells," *Proc. Natl. Acad. Sci. USA* 84:5600-5604 (1987).

Nabai, et al., "Cost Reduction of Skin Biopsy and Surgical Instrumentation," *Dermatology* 191:240-241 (1995).

Nimpf, et al., "$\beta_2$-Glycoprotein-I (apo-H) Inhibits the Release Reaction of Human Platelets During ADP-Induced Aggregation," *Atherosclerosis* 63:109-114 (1987).

Nimpf, et al., "Prothrombinase Activity of Human Platelets is Inhibited by $\beta_2$-Glycoprotein-I," *Biochimica et Biophysica Acta* 884:142-149 (1986).

Nonaka, et al., "Molecular cloning of mouse beta 2-glycoprotein I and mapping of the gene to chromosome II", *Genomics* 13: 1082-1087 (1992).

Ohkura, et al., "Plasmin Can Reduce the Function of Human $\beta_2$-Glycoprotein I by Cleaving Domain V Into a Nicked Form," *Blood* 91(11):4173-4179 (1998).

O'Reilly, et al., "Angiostatin: A Novel Angiogenesis Inhibitor That Mediates the Suppression of Metastases by a Lewis Lung Carcinoma," *Cell* 79:315-328 (1994).

O'Reilly, et al., "Angiostain Induces and Sustains Dormancy of Human Primary Tumors in Mice," *Nature Medicine* 2(6):689-692 (1996).

O'Reilly, et al., "Endostatin: An Endogenous Inhibitor of Angiogenesis and Tumor Growth," *Cell* 88:277-285 (1997).

O'Reilly, et al., "Antiangiogenic Activity of the Cleaved Conformation of the Serpin Antithrombin," *Science* 285:1926-1928 (1999).

Patan, et al., "Intussusceptive Microvascular Growth in a Human Colon Adenocarinoma Xenograft: A Novel Mechanism of Tumor Angiogenesis," *Microvascular Research* 51:260-272 (1996).

Polz and Kostner, "The Binding of $\beta_2$-Glycoprotein-I to Human Serum Lipoproteins," *FEBS Letter* 102(1):183-186 (1979).

Polz, et al., "Investigations on $\beta_2$-Glycoprotein-I in the Rat: Isolation From Serum and Demonstration in Lipoprotein Density Fractions," *Int. J. Biochem.* 11:265-270 (1980).

Rafi, "Circulating Endothelial Precursors: Mystery, Reality, and Promise," *The Journal of Clinical Investigation* 105(1):17-19 (2000).

Ran, et al., "Infarction of Solid Hodgkin's Tumors in Mice by Antibody-Directed Targeting of Tissue Factor to Tumor Vasculature," *Cancer Research* 58:4646-4653 (1998).

Raynor, et al., "Annexin II Enhances Cytomegalovirus Binding and Fusion to Phospholipid Membranes," *Biochemistry* 38:5089-5095 (1999).

Rhim, et al., "Human Prothrombin Fragment 1 and 2 Inhibit bFGF-Induced BCE Cell Growth," *Biochemical and Biophysical Research Communications* 252:513-516 (1998).

Røjkjær, et al., "Characterization of the Interaction between $\beta_2$-Glycoprotein I and Calmodulin, and Identification of a Binding Sequence in $\beta_2$-Glycoprotein I," *Biochimica et Biophysical Acta* 1339:217-225 (1997).

Schousboe, "Purification, Characterization and Identification of an Agglutinin in Human Serum," *Biochimica et Biophysica Acta* 579:396-408 (1979).

Schousboe, "Binding of $\beta_2$-Glycoprotein I to Platelets: Effect of Adenylate Cyclase Activity," *Thrombosis Research* 19:225-237 (1980).

Schousboe, "$\beta_2$-Glycoprotein I: A Plasma Inhibitor of the Contact Activation of the Intrinsic Blood Coagulation Pathway," *Blood* 66(5):1086-1091 (1985).

Schousboe and Rasmussen, "Synchronized Inhibition of the Phospholipid Mediated Autoactivation of Factor XII in Plasma by $\beta_2$-Glycoprotein I and Anti-$\beta_2$-Glycoprotein I," *Thrombosis and Haemostasis* 73(5):798-804 (1995).

Schroit, et al., "Radioiodinated, Photoactivatable Phosphatidylcholine and Phosphatidylserine: Transfer Properties and Differential Photoreactive Interaction with Human Erythrocyte Membrane Proteins," *Biochemistry* 26:1812-1819 (1987).

Schroit, et al., "Involvement of Rh Blood Group Polypeptides in the Maintenance of Aminophospholipid Asymmetry," *Biochemistry* 29:10303-10306 (1990).

Schulter, et al., "Impact of Apolipoprotein(a) on In Vitro Angiognesis," *Arterioscler Thromb Vasc Biol.* 21:433-438 (2001).

Schwarzenbacher, et al., "Crystal Structure of Human $\beta_2$-Glycoprotein I: Implications for Phospholipid Binding and the Antiphospholipid Syndrome," *The EMBO Journal* 18(22):6228-6239 (1999).

Sheng, et al., "Imparied Thrombin Generation in $\beta_2$-Glycoprotein I Null Mice," *The Journal of Biological Chemistry* 276(17):13817-13821 (2001).

Shi, Wei, et al., "Anticardiolipin Antibodies Block the Inhibition by $\beta_2$-Glycoprotein I of the Factor Xa Generating Activity of Platelets," *Thrombosis and Haemostasis*, 70(2):342-345 (1993).

Singh and Liu, "Modification of Cysteine Residues by N-Ethylmaleimide Inhibits Annexin II Tetramer Mediated Liposome Aggregation," *Archives of Biochemistry and Biophysics* 381(2):235-240 (2000).

Steinkasserer, et al., "Complete Nucleotide and Deduced Amino Acid Sequence of Human $\beta_2$-Glycoprotein I," *Biochem. J.* 277:387-391 (1991).

Takigawa, et al., "Induction of Angiogenesis in Chick Yolk-Sac Membrane by Polyamines and Its Inhibition by Tissue Inhibitors of Metalloproteinases (TIMP and TIMP-2)," *Biochemical and Biophysical Research Communications* 171(3):1264-1271 (1990).

Taylor and Folkman, "Protamine is an Inhibitor of Angiogenesis," *Nature* 297:307-312 (1982).

Thompson, et al., "Tumours Acquire Their Vasculature by Vessel Incorporation, Not Vessel Ingrowth," *Journal of Pathology* 151:323-332 (1987).

Thurston, et al., "Leakage-Resistant Blood Vessels in Mice Transgenically Overexpressing Angiopoietin-1," *Science* 286:2511-2514 (1999).

Thurston, et al., "Angiopoietin-1 Protects the Adult Vasculature Against Plasma Leakage," *Nature Medicine* 6(4):460-463 (2000).

Trieu and Uckun, "Apolipoprotein(a), a Link between Atherosclerosis and Tumor Angiogenesis," *Biochemical and Biophysical Research Communications* 257:714-718 (1999).

Tsopanoglou, et al., "Thrombin Promotes Angiogenesis by a Mechanism Independent of Fibrin Formation," *American Journal of Physiology* 264:C1302-C1307 (1993).

Uchida, et al., "Induction of Apoptosis by Phosphatidylserine," *J. Biochem.* 123:1073-1078 (1998).

van Boven and Lane, "Antithrombin and Its Inherited Deficiency States," *Seminars in Hematology* 34(3):188-204 (1997).

Veikkola, et al., Regulation of Angiogenesis via Vascular Endothelial Growth Factor Receptors, *Cancer Research* 60:203-212 (2000).

Vogel, et al., "Apolipoprotein E: A Potent Inhibitor of Endothelial and Tumor Cell Proliferations," *Journal of Cellular Biochemistry* 54:299-308 (1994).

Wagenknecht and McIntyre, "Changes in $\beta_2$-Glycoprotein I Antigenicity Induced by Phospholipid Binding," *Thrombosis and Haemostasis,* 69(4):361-365 (1993).

Weidner, et al., "Tumor Angiogenesis and Metastasis—Correlation in Invasive Breast Carcinoma," *The New England Journal of Medicine* 324(1):1-8 (1991).

Willems, et al., "Role of Divalency in the High-Affinity Binding of Anticardiolipin Antibody—$\beta_2$-Glyprotein I Complexes to Lipid Membranes," *Biochemistry* 35:13833-13842 (1996).

Wurm, "$\beta_2$-Glycoprotein-I (Apolipoprotein H) Interactions with Phospholipid Vesicles," *Int. J. Biochem.* 16(5):511-515 (1984).

Yancopoulos, et al., "Vascular-Specific Growth Factors and Blood Vessel Formation," *Nature* 407:242-248 (2000).

U.S. Appl. No. 11/183,555, filed Jul. 18, 2005, Hembrough.

Beecken et al., "An Endogenous Inhibitor of Angiogenesis Derived From a Transitional Cell Carcinoma; Clipped$\beta_2$ -Glycoprotein-I", *Ann. Surg. Oncol.*, 13(9):1241-1251, 2006.

Hammel et al., "Mechanism of the Interaction of $\beta_2$ -Glycoprotein I with Negatively Charged Phospholipid Membranes", *Biochemistry*, 40:14173-14181, 2001.

Lin et al., "$\beta_2$-Glycoprotein I Protects J774A.1 Macrophages and Human Coronary Artery Smooth Muscle Cells Against Apoptosis", *J. Cell. Biochem.*, 94:485-496, 2005.

Shi et al., "$\beta_2$-Glycoprotein I Binds Factor XI and Inhibits its Activation by Thrombin and Factor XIIa: Loss of Inhibition by Clipped B2-Glycoprotein I", *Proc. Natl. Acad. Sci., USA*, 101(11):3939-3944, 2004.

Shi et al., "Domain V of $\beta_2$-Glycoprotein I Binds Factor XI/Xia and is Cleaved at $Lys^{317}$-$Th4^{318}$", *J. Biol. Chem.*, 280(2):907-912, 2005.

* cited by examiner

β-2-GLYCOPROTEIN IS AN INHIBITOR OF ANGIOGENESIS

This application claims benefit of Ser. No. 60/381,219 filed May 17, 2002.

STATEMENT REGARDING FEDERALLY SPONSORED RESEARCH OR DEVELOPMENT

Not Applicable.

REFERENCE TO A "Microfiche Appendix"

Not Applicable.

BACKGROUND OF THE INVENTION

1. Field of the Invention

The present disclosure relates to methods and compositions for inhibiting angiogenesis.

2. Description of Related Art

β2-Glycoprotein 1 (β2GP1), also known as apolipoprotein H, is a 50 kDa plasma protein that is an abundant plasma glycoprotein found both free and associated with lipoprotein (Polz et al., *FEBS Letters* 102:183–186, 1979; Wurm, H., *Int. J. Biochem.* 16:511–515, 1984). Although the precise physiological role of β2GP1 is not known, in vitro studies suggest that it likely functions as a natural anticoagulant. β2GP1 has been shown to inhibit intrinsic pathway activation (Schousboe, I., *Blood* 66:1086–109, 1985; Schousboe and Rasmussen, *Throm. Haemostasis* 73:798–804, 1995), tenase (Shi et al., *Throm. Haemostasis* 70:342–345, 1993), and prothrombinase activities (Nimpf et al., *Biochim. Biophys. Acta* 884:142–149, 1986; Goldsmith et al., *Brit. J. Heamatol.* 87:548–554, 1994) on the surface of activated platelets and synthetic phospholipid vesicles. β2GP1 also inhibits the activity of activated protein C on procoagulant surfaces (Matsuda et al., *American Journal of Hematology* 49:89–91, 1995; Mori et al., *Throm. Haemostasis* 75:49–55, 1996). Plasma levels of β2GP1 have also been shown to fall during disseminated intravascular coagulation (Brighton et al., *Brit. J. Heamatol.* 93:185–194, 1996), which is consistent with the consumption of β2GP1 in this thrombotic process.

β2GP1 inhibits ADP-induced platelet aggregation (Schousboe, I., *Throm. Res.* 19:225–237, 1980; Nimpf et al., *Atherosclerosis* 63:109–114, 1987) and participates in the etiology of several thrombolytic diseases (see, e.g., Brighton et al., *Brit. J. Heamatol.* 93:185–194, 1996; Asherson and Cervera, *J Invest Dermatol* 100(1):21S–27S, 1993; Mackworth-Young, C., *Immunol. Today* 11:60–65, 1990; Kandiah et al., *Lupus* 5:381–385, 1996). β2GP1 preferentially binds to surfaces bearing negatively charged phospholipids. β2GP1 binds the negatively charged lipids phosphatidylserine (PS) and cardiolipin (CL), and regulates thrombosis by its ability to compete for the assembly of coagulation factors on PS-expressing platelet and endothelial cell membranes.

β2GP1 binds endothelial cells with high affinity, particularly endothelial cells that express acidic phospholipids (Ma et al., *J. Biol. Chem.* 275:15541–15548, 2000; Del Papa et al., *J. Immunol.* 160:5572–5578, 1998; Del Papa et al., *Arthritis Rhuem.* 40:551–561, 1997; Del Papa et al., *Clinical & Experimental Rheumatology* 13:179–185, 1995), and undergoes specific proteolytic cleavage (Horbach et al., *Throm. Haemostasis* 81:87–95, 1999). Other important in vivo targets of β2GP1 interaction are apoptotic or necrotic cells, where anionic phospholipids normally located in the inner side of the cell membrane become surface-exposed and serve as targets for β2GP1 binding (Balasubramanian and Schroit, *J. Biol. Chem.* 273:29272–29277, 1998; Balasubramanian et al., *J. Biol. Chem.* 272:31113–31117, 1997). Subsequent to binding, the protein undergoes a conformational change (Wagenknecht and McIntyre, *Throm. Haemostasis* 69:361–365, 1993; Borchman et al., *Clin. Exp. Immunol.* 102:373–378, 1995; Lee et al., *Biochim. Biophys. Acta* 1509:475–484, 2000) that is recognized by a specific lipid/β2GP1 dependent receptor on the surface of phagocytes (Balasubramanian and Schroit, *J. Biol. Chem.* 273:29272–29277, 1998). Similarly, the association of β2GP1 with lipids can serve as antigens for antiphospholipid/β2GP1 autoantibodies (aPLAs) that are associated with systemic lupus erythematosus and antiphospholipid syndrome (McNeil et al., *Proc. Natl. Acad. Sci.* (USA) 87:4120–4124, 1990; Bevers et al., *Throm. Haemostasis* 66:629–632, 1991; Galli et al., *Lancet* 335:1544–1547, 1990). Although the structural rearrangements that are important for lipid-dependent phagocyte recognition and the generation of antiphospholipid antibodies are unknown, it is unequivocal that both the protein and the target membranes undergo critical changes in their conformation.

β2GP1 is a single-chain glycoprotein composed of 326 amino acid residues and consists of four complement control protein (CCP) modules (domains I through IV), as well as a distinct C-terminal domain V (Steinkasserer et al., *Biochem. J.* 277:387–391, 1991). From the crystal structure of β2GP1 (Bouma et al., *EMBO Journal* 18:5166–5174, 1999; Schwarzenbacher et al., *EMBO Journal* 18:6228–6239, 1999), it is known that the four CCP domains exhibit an elliptically shaped β-sandwich structure comprised of several antiparallel β-strands wrapped around a well-defined hydrophobic core containing one conserved tryptophan each. In contrast, domain V folds into a central β-spiral with two small helices and carries a distinct positive charge in the proximity of a surface-exposed loop region comprising Trp316. Domain V carries the lipid binding region within the lysine-rich sequence motif (281CKNKEKKC288) and a hydrophobic loop (313LAFW316) important to membrane binding.

From experiments designed to identify the lipid-binding site of β2GP1 (now known to be domain V), Hunt and Krilis identified an inactive form of β2GP1 that does not bind lipids and as a result did not bind lipid/β2GP1 complex-specific phospholipid antibodies (Hunt and Krilis, *J. Immunol.* 152:653–659, 1994; Hunt et al., *Proc. Natl. Acad. Sci.* (USA) 90:2141–2145, 1993). Sequence analyses of the inactive form yielded two N-terminal sequences. One of the N-terminal sequences corresponded to the N-terminus of the intact active form of β2GP1, while the other was a new sequence that started at Thr-318. The authors concluded that the inactive form was cleaved in domain V between amino acids Lys-317 and Thr-318 but was still a single polypeptide because the disulfides delineating the five domains remained intact. Although the crystal structure of the nicked protein has yet to be determined, it is reasonable to assume that the cleavage of 32GP 1 at Lys 317/Thr 318 results in a dramatic change in the proteins conformation since its lipid binding properties are essentially abrogated and lipid/β2GP1 complex-specific antiphospholipid antibodies no longer bind the protein. Using the crystal structure of the intact protein, molecular modeling, and epitope mapping with monoclonal β2GP1 antibody, Matssura et al. (*International Immunology* 12:1183–1192, 2000) proposed that cleavage results in novel hydrophobic and electrostatic interactions in domain V that affect lipid and phospholipid antibody binding. Importantly, these changes might propagate down through the polypeptide to other domains.

Varying levels of endogenous nicked protein can be found in the plasma of certain individuals, especially leukemia patients (Itoh et al., *J. Biochem.* 128:1017–1024, 2000) and patients treated with streptokinase (Horbach et al., *Throm. Haemostasis* 81:87–95, 1999). In vitro, β2GP1 is proteolytically cleaved by enzymes that participate in the coagulation cascade; factor Xa, elastase, and plasmin all clip β2GP1 at Lys-317 and Thr-318. Moreover, the addition of urokinase to plasmin inhibitor (α2PI) depleted plasma also generated nicked β2GP1 (Ohkura et al., *Blood* 91:4173–4179, 1998). These observations suggest that activation of fibrinolysis in vivo induces the cleavage of intact β2GP1 by plasmin which results in the generation of the nicked protein (Blank et al., *Proc. Natl. Acad. Sci.* (USA) 96:5164–5168, 1999). These data taken together with the observations that β2GP1 binds endothelial cells (George et al., *Circulation* 99:2227–2230, 1999; George et al., *Circulation* 97:900–906, 1998) through annexin II (Ma et al., *J. Biol. Chem.* 275:15541–15548, 2000) raises the possibility that localized production of plasmin at the endothelial invasion front during wound repair could cleave β2GP1. Thus, the nicked form of β2GP1 could be generated directly on the cell surface, which would result in altered properties that directly affect endothelial cell function.

Angiogenesis, the process by which new blood vessels are formed by sprouting from pre-existing vessels, is a highly regulated process that involves endothelial cell proliferation, proteolysis of matrix molecules, self-association, elongation and migration. Angiogenic agents may be used to induce angiogenesis, or it may be the result of a natural condition. Angiogenesis is essential to a variety of normal activities, such as reproduction, development, tissue and organ growth, and wound repair, and involves a complex interplay of molecules that stimulate and inhibit the growth and migration of endothelial cells, the primary cells of the capillary blood vessels. Normally these molecules maintain the microvasculature in a quiescent state (i.e., without capillary growth) for prolonged periods which can last for several years or even decades.

While angiogenesis is essential to homeostasis (Adams et al., *Genes & Development* 13:295–306, 1999; Erlebacher et al., *Cell* 80:371–378, 1995), its timely inhibition is critical to normal wound healing and development. For example, during wound repair endothelial cells can undergo rapid proliferation, with a much shorter turnover time (Folkman and Shing, *J. Biol. Chem.*, 267:10931–34, 1992; Folkman and Klagsbrun, *Science* 235:442–47, 1987). Should the balance between pro and antiangiogenic regulators go awry, uncontrolled capillary formation such as that seen in rheumatoid arthritis, diabetic retinopathy, psoriasis, retrolental fibroplasias, hemangiomas, and tumor cell growth, as well as metastasis, may result (Folkman, J., *Nature Medicine* 1:27–31, 1995; Ellis and Fidler, *European Journal of Cancer* 32A:2451–2460, 1996).

There are many diseases, categorized as "angiogenic diseases," which are characterized by persistent unregulated angiogenesis. Unregulated angiogenesis can either be the direct cause of the particular disease, or it may exacerbate an existing pathological condition. For example, ocular neovascularization appears to be the most common cause of blindness and underlies the pathology of several eye diseases. In arthritis, newly formed capillary blood vessels can invade joints and destroy cartilage. In diabetes, new capillaries may form in the retina and invade the vitreous humor, which can cause bleeding and blindness.

The growth and metastasis of solid tumors can also be angiogenesis-dependent (Folkman, J., *Cancer Res.* 46:467–73, 1986; Folkman et al., "Tumor Angiogenesis," Chapter 10, pp. 206–32, in The Molecular Basis of Cancer, Mendelsohn et al., eds. (W. B. Saunders, 1995)). Tumor cells must attract new vessels to expand locally and produce metastasis. For example, tumors that enlarge to greater than 2 mm. in diameter need to obtain their own blood supply, and can do so by inducing the growth of new capillary blood vessels. These new blood vessels become embedded in the tumor and provide nutrients and growth factors essential for tumor growth, as well as a means for tumor cells to enter the circulation and metastasize to other distant sites (Weidner et al., *New Eng. J. Med.,* 324(1):1–8, 1991). Drugs that function as natural inhibitors of angiogenesis have been shown to prevent the growth of small tumors in tumor-bearing animals (O'Reilly et al., *Cell* 79:315–328, 1994). Sometimes the use of such negative regulators leads to tumor regression and dormancy even after cessation of treatment (O'Reilly et al., *Cell* 88:277–85, 1997). Additionally, it has also been shown that supplying inhibitors of angiogenesis to certain tumors can potentiate their response to other therapeutic regimens (e.g., chemotherapy).

During the past decade, several negative regulators of angiogenesis have been discovered. Compounds that have been reported to inhibit endothelial cell proliferation in different experimental systems include TGF-β, (Muller et al., *Proc. Natl. Acad. Sci.* (USA) 84:5600–5604, 1987), thrombospondin (Good et al., *Proc. Natl. Acad. Sci.* (USA) 87:6624–6628, 1990), IL-1 (Cozzolino et al., *Proc. Natl. Acad. Sci.* (USA) 87:6487–6491, 1990), IFN-γ and IFN-α (Friesel et al., *J. Cell. Biol.* 104:689–696, 1987), tissue inhibitor of metalloproteinase-1 (TIMP-1) (Takigawa et al., *Biochem. Biophy. Res. Commun.* 171:1264–1271, 1990), platelet factor 4 (PF4) (Maione et al., *Science* 247:77–79, 1990), protamine (Taylor and Folkman, *Nature* 297:307–312, 1982), fumagillin (Ingber et al., *Nature* 348: 555–557, 1990) and angiostatin (O'Reilly et al., *Cell* 79:315–328, 1994).

Some of these proteins are proteolytic fragments of the same proteins that control the balance between the formation and dissolution of fibrin clots formed as a result of tissue damage and wound healing. For example, proteolysis of antithrombin III (van Boven and Lane, *Seminars in Hematology* 34:188–204, 1997), thrombin (Tsopanoglou et al., *American Journal of Physiology* 264:C1302–C1307, 1993), and plasminogen, which all play a critical role in controlling clot formation and angiogenesis, result in the production of cleaved antithrombin III (O'Reilly et al., *Science* 285: 1926–1928, 1999; Larsson, et al., *J. Biol. Chem.* 276: 11996–12002, 2001), prothrombin fragments 1 and 2 (Rhim et al., *Biochem. Bioph. Res. Co.* 252:513–516, 1998), and angiostatin (O'Reilly et al., *Cell* 79:315–328, 1994; O'Reilly et al, *Nature Medicine* 2:689–692, 1996), respectively, all of which inhibit the growth of vascular endothelial cells. Although several angiogenesis inhibitors are currently under development for use in treating diseases, there exists a need for better therapeutic options for inhibiting angiogenesis.

BRIEF SUMMARY OF THE INVENTION

The present disclosure describes methods for inhibiting, treating, or preventing unwanted endothelial cell proliferation, cord formation, cell migration, angiogenesis and angioectasia, especially as related to cancer or tumor growth, by the administration of an angiogenesis inhibitor, Beta-2-glycoprotein 1 (β2GP1). β2GP1 plays an important regulatory role in endothelial cell physiology, angiogenesis, and tumor biology, and has important therapeutic implications in inhibiting the angiogenic properties of proliferating tumors. In particular, β2GP1 is able to abrogate angiogenesis and angioectasia, inhibit endothelial cell growth, cord formation, and cell migration, and significantly inhibit tumor growth and metastasis. Also disclosed are methods of inhibiting, treating, or preventing unwanted endothelial cell proliferation and/or migration, as well as angiogenesis and angioectasia within a tissue or organism by providing β2GP1 to cells associated with the tissue or organism. Inhibition of angiogenesis and/or angioectasia is useful for the treatment of diseases and conditions associated with increased or abnormal angiogenesis and/or endothelial cell proliferation.

As used herein, the term "β2GP1" includes both the intact form of β2GP1 and the nicked form of β2GP1 ("N-β2GP1"). The amino acid sequence of β2GP1 varies slightly between species, and such variations fall within the scope of the term "β2GP1." As used herein, N-β2GP1 is a β2GP1 protein that is cleaved at Lys 317/Thr 318. In a preferred embodiment, the N-β2GP1 is still a single polypeptide. As used herein, the term "β2GP1 polypeptide" includes polypeptides, proteins, and peptides of β2GP1. It is to be understood that β2GP1 polypeptides, proteins, peptides, analogs, derivatives, and fragments thereof may have endothelial and/or angiogenesis inhibiting activity and that any such β2GP1 polypeptides, proteins, peptides, analogs, derivatives, and fragments thereof fall within the scope and spirit of the present disclosure.

The present disclosure provides methods for treating diseases and processes mediated by undesired and uncontrolled angiogenesis and/or angioectasia by administering to a cell, a tissue, or an organism a composition comprising a substantially purified β2GP1 in a dosage sufficient to inhibit, prevent, or treat angiogenesis and/or angioectasia. The present disclosure is particularly useful for treating or for repressing the growth of neoplasms or tumors, as well as reducing tumor mass. Administration of β2GP1 to a human or animal with prevascularized metastasized tumors can prevent the growth or expansion of those tumors. The presence of β2GP1 inhibits, prevents, or treats angiogenesis and/or angioectasia within a tissue or organism, in part by preventing or arresting neovascularization into the tissue and blood vessel dilation within a tissue. β2GP1 may be provided to a cell, tissue, or organism exogenously, by upregulating the expression of endogenous β2GP1, or by exogenously providing an expression vector or construct that expresses β2GP1 in the target cell, tissue, or organism.

The disclosure also includes diagnostic methods and kits for determining the prognosis of an organism by assaying for the presence of β2GP1 in biological fluids such as plasma and/or within a cancer or tumor. The diagnostic methods and kits can be in any configuration well known to those of ordinary skill in the art. The present disclosure also includes antibodies specific for β2GP1 and antibodies that inhibit the binding of antibodies specific for β2GP1. These antibodies can be polyclonal antibodies or monoclonal antibodies. The antibodies specific for β2GP1 can be used in diagnostic kits to detect the presence and quantity of β2GP1, which may be diagnostic or prognostic for the occurrence or recurrence of cancer or other disease mediated by angiogenesis.

The methods of the present disclosure are clinically useful for treating a host of diseases and conditions associated with angiogenesis, and for interfering with angiogenesis associated with reproductive functions. Diseases and conditions that are mediated by angiogenesis include, but are not limited to, hemangioma, neoplasm, cancer, solid tumors, leukemia, metastasis, angioectasia, telangiectasia, psoriasis, scleroderma, pyogenic granuloma, Myocardial angiogenesis, plaque neovascularization, cororany collaterals, ischemic limb angiogenesis, corneal diseases, rubeosis, neovascular glaucoma, diabetic retinopathy, retrolental fibroplasia, arthritis, diabetic neovascularization, macular degeneration, wound healing, peptic ulcer, fractures, keloids, vasculogenesis, hematopoiesis, ovulation, menstruation, and placentation. The methods are also diagnostically useful for assessing the prognosis of tumors and other disorders associated with angiogenesis. Furthermore, the methods are useful reagents for investigation of angiogenesis in the laboratory setting.

A preferred embodiment of the present disclosure is a method of inhibiting angiogenesis and/or angioectasia within a tissue comprising administering an effective amount of β2GP1 to cells associated with the tissue, wherein the amount is sufficient to inhibit angiogenesis within the tissue. Preferably angiogenesis and/or angioectasia is inhibited in human tissue. In preferred embodiments, the β2GP1 is intact β2GP1, N-β2GP1, or recombinant β2GP1. Preferably the β2GP1 is administered to the cells by exposing a composition comprising β2GP1 polypeptide to the cells. In a preferred embodiment, the cells associated with the tissue are endothelial cells. Preferably the endothelial cells are selected from the group consisting of pulmonary endothelial cells, heart endothelial cells, gastrointestinal endothelial cells, brain endothelial cells, lymphatic endothelial cells, genital-urinary endothelial cells, skin endothelial cells, bone endothelial cells, muscle endothelial cells, breast endothelial cells, retinal endothelial cells, endocrine endothelial cells, central nervous system endothelial cells, hepatic endothelial cells, and umbilical cord endothelial cells. In another preferred embodiment, the tissue is a tumor, and the administration of β2GP1 to the tumor tissue inhibits neovascularization into the tumor. In yet another preferred embodiment, an antiangiogenic agent is administered to the cells in conjunction with β2GP1. Preferably the antiangiogenic agent is selected from the group consisting of angiostatin, endostatin, trastuzumab, thrombospondin, IFN-α, TIMP-1, PF4, fumagillin, and mixtures thereof. In another preferred embodiment, the β2GP1 is supplied to the cells topically, intravenously, subcutaneously, by direct injection into the tissue, or intraperitoneally.

Another preferred embodiment of the present disclosure is a method of inhibiting endothelial cell proliferation comprising administering an effective amount of β2GP1 to the cells, wherein the amount is sufficient to inhibit endothelial cell proliferation. Preferably endothelial cell proliferation is inhibited in human endothelial cells. In preferred embodiments, the β2GP1 is intact β2GP1, N-β2GP1, or recombinant β2GP1. In other preferred embodiments, administering an effective amount of β2GP1 is also able to inhibit endothelial cell migration and/or differentiation, in particular inhibit endothelial cells from differentiating into tubular capillary structures.

Yet another preferred embodiment of the present disclosure is a method of inhibiting angiogenesis and/or angioectasia within a neoplasm comprising administering an effective amount of β2GP1 to the neoplasm, wherein the amount is sufficient to inhibit angiogenesis and/or angioectasia within the neoplasm. Preferably angiogenesis and/or angioectasia is inhibited in a human neoplasm. In preferred embodiments, the β2GP1 is intact β2GP1, N-β2GP1, or recombinant β2GP1. Preferably the neoplasm is a tumor. In another preferred embodiment, administering an effective amount of β2GP1 is also able to inhibit neovascularization into the tumor. In yet another preferred embodiment, administering of an effective amount of β2GP1 is able to inhibit metastasis of the neoplasm or tumor. In yet another preferred embodiment, an antiangiogenic agent is administered to the neoplasm in conjunction with β2GP1. Preferably the antiangiogenic agent is selected from the group consisting of angiostatin, endostatin, trastuzumab, thrombospondin, IFN-α, TIMP-1, PF4, fumagillin, and mixtures thereof. In yet another preferred embodiment, a therapeutic agent useful in the treatment of the neoplasm is administered in conjunction with β2GP1. Preferably the therapeutic agent is selected from the group consisting of cisplatin, doxorubicin, paclitaxel, vincristine, and vinblastin.

A preferred embodiment of the present disclosure is a method of inhibiting angiogenesis and/or angioectasia at a tumor site in a subject comprising administering an effective amount of β2GP1 to the subject, wherein the amount is sufficient to inhibit angiogenesis and/or angioectasia at the tumor site. Preferably the subject is human. In preferred embodiments, the β2GP1 is intact β2GP1, N-β2GP1, or recombinant β2GP1. In other preferred embodiments, the route of administration of β2GP1 to the subject is oral, intravenous, intramuscular, intrathecal, intradermal, intraperitoneal, subcutaneous, intrapleural, intrauterine, rectal, vaginal, topical, intratumor, transdermal, or transmucosal.

Another preferred embodiment of the present disclosure is a method of inhibiting angiogenesis and/or angioectasia at a site in a subject suffering from an angiogenic disease comprising administering an effective amount of β2GP1 to the subject, wherein the amount is sufficient to inhibit angiogenesis and/or angioectasia at the site. Preferably the subject is human in preferred embodiments, the β2GP1 is intact β2GP1, N-β2GP1, or recombinant β2GP1. Preferably the β2GP1 is administered to the subject orally, intravenously, subcutaneously, intramuscularly, or topically. In yet another preferred embodiment the angiogenic disease is characterized by persistent unregulated angiogenesis. Preferably the angiogenic disease is selected from the group consisting of diabetic retinopathy, retrolental fibroplasia, trachoma, neovascular glaucoma, psoriases, immune-inflammation, non-immune inflammation, atherosclerosis, and excessive wound repair. In other preferred embodiments, the site in the subject is dermis, epidermis, endometrium, retina, surgical wound, gastrointestinal tract, umbilical cord, liver, kidney, reproductive system, lymphoid system, central nervous system, breast tissue, urinary tract, circulatory system, bone, muscle, or respiratory tract.

Examples of other preferred embodiments of the present disclosure include, but are not limited to a method of inhibiting angiogenesis and/or angioectasia in melanoma tissue comprising administering from about 50 to about 200 mg of β2GP1 topically; a method of inhibiting angiogenesis and/or angioectasia in fibrosarcoma tissue comprising administering from about 200 to about 300 mg of β2GP1 intravenously; a method of inhibiting angiogenesis and/or angioectasia in renal cell carcinoma tissue comprising administering from about 25 to about 125 mg of β2GP1 intravenously; a method of inhibiting angiogenesis and/or angioectasia in breast cancer tissue comprising administering from about 250 to about 400 mg of β2GP1 to the tissue by direct injection; a method of inhibiting angiogenesis and/or angioectasia in prostate cancer tissue comprising administering from about 150 to about 300 mg of β2GP1 to the tissue by direct injection; a method of inhibiting angiogenesis and/or angioectasia in bladder cancer tissue comprising administering from about 200 to about 300 mg of β2GP1 intravenously; and a method of inhibiting angiogenesis and/or angioectasia in colon cancer tissue comprising administering from about 50 to about 250 mg of β2GP1 intravenously.

A preferred embodiment of the present disclosure is a pharmaceutical composition comprising β2GP1 and a second antiangiogenic agent useful for the inhibition of angiogenesis and/or angioectasia. Preferably the second antiangiogenic agent is selected from the group consisting of angiostatin, endostatin, trastuzumab, thrombospondin, IFN-α, TIMP-1, PF4, and fumagillin. Another preferred embodiment is a pharmaceutical composition comprising β2GP1 and a therapeutic agent useful for the treatment of a neoplasm. Preferably the therapeutic agent is selected from the group consisting of cisplatin, doxorubicin, paclitaxel, vincristine, and vinblastin.

BRIEF DESCRIPTION OF THE SEVERAL VIEWS OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 10. Mice treated with intact β2GP1 and N-β2GP1 were injected with FITC-HSA. The mice were then prepared as described in. FIG. 8 and videotaped throughout the application of VEGF. The arrows on the left point to the same vessel (orientation problems after moving the animals) 1 hour after adding VEGF. Note absence of dilation in the mice treated with N-β2GP1. These results suggest that N-β2GP1 inhibits growth factor-induced angioectasia in vivo.

FIG. 12. Mice treated with intact β2GP1, N-β2GP1, and HSA were prepared as described in. FIG. 8 and videotaped before and after (0.5 hours) the application of nitroglycerin. The circles mark the areas of obvious vessel dilation. These results suggest that β2GP1 does not inhibit chemically-induced angioectasia in vivo.

DETAILED DESCRIPTION OF THE INVENTION

Figure 1:
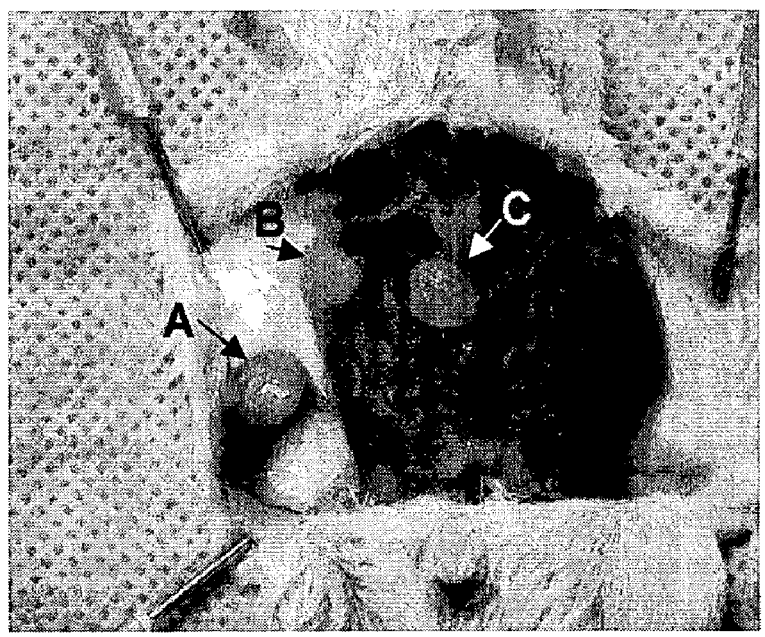
FIG. 1. Antiangiogenic property of β2GP1: Control gel foam plugs containing human serum albumin (A) and plugs containing intact β2GP1 (B) and N-β2GP1 (C) were implanted subcutaneously. The mice were sacrificed two weeks later. Note the dramatic vascularization of plug A and the clear non-adherent and non-vascularized plugs B and C, which demonstrates the ability of β2GP1 to inhibit or prevent neovascularization.

Beta-2-glycoprotein 1 (β2GP1) is a protein that has antiangiogenic properties. The present disclosure relates to the inhibition, treatment, or prevention of unwanted endothelial cell proliferation, cord formation, and cell migration, as well as angiogenesis and angioectasia. Angiogenic diseases that may be treated by using β2GP1 include but are not limited to, diabetic retinopathy, retrolental fibroplasia, trachoma, neovascular glaucoma, psoriases, angio-fibromas, immune and non-immune inflammation, capillary formation within atherosclerotic plaques, hemangiomas, excessive wound repair, solid tumors, Kaposi's sarcoma, and the like. In a preferred embodiment, the present disclosure relates to the use of β2GP1 to inhibit angiogenesis and angioectasia at the site of tumorigenesis or tumor growth, which can then prevent or inhibit tumor growth.

β2GP1 includes both the intact form of β2GP1 and N-β2GP1. One form of β2GP1 polypeptide (a human amino acid sequence) is set forth below:

```
                                                    SEQ ID:1
GRTCPKPDDLPFSTVVPLKTFYEPGEEITYSCKPGYVSRGGMRKFICPLT

GLWPINTLKCTPRVCPFAGILENGAVRYTTFEYPNTISFSCNTGFYLNGA

GDSAKCTEEGKWSPELPVCAPIICPPPSIPTFATLRVYKPSAGNNSLYRDT

AGVFECLPQHAMFGNDTITCTTHGNWTKLPECREVKCPFPSRPDNGFVNYP

GAKPTLYYKDKATFGCHDGYSLDGPEEIECTKLGNWSAMPSCKASCKVPVK

GKATVVYQGERVKIQEKFKNGMLHGDKVSFFCKNKEKKCSYTEDAQCIDGT

GIEVPKCFKEHSSLAFWKTDASDVKPC
```

However, the β2GP1 polypeptide is not limited to the use of the above exemplary sequence. Indeed, many other β2GP1 sequences are known in the art, and genetic sequences can vary between different species and individuals. For example, nucleic acid, cDNA, and protein sequences have been determined for human, rat, bovine, and mouse β2GP1, and reveal a high degree of homology in the β2GP1 sequences between species (see e.g., Steinkasserer et al., *Biochem. J.* 277:387–391, 1991; Lozier et al., *Proc. Natl. Acad. Sci.* (USA) 81:3640–3645, 1984; Kristensen et al., *FEBS Lett.* 289(2):183–186, 1991; Matsuura et al., *Int. Immunol.* 3(12):1217–1221, 1991; Mehdi et al., *Gene* 108: 293–298, 1991; Day et al., *Int. J. Clin. Lab. Res.* 21(3): 256–263, 1992; Aoyama et al., *Nucleic Acids Res.* 17:6401, 1989; Nonaka et al., *Genomics* 13:1082–1087, 1992; incorporated herein by reference). This natural scope of allelic variation is included within the scope of the present disclosure. It is to be understood that the spirit of the present disclosure is contemplated to include any derivatives of β2GP1 that inhibit, treat, or prevent unwanted endothelial cell proliferation and/or angiogenesis. The β2GP1 polypeptide can also include other domains, such as epitope tags and His tags (e.g., the protein can be a fusion protein). The present disclosure also includes genes and cDNAs that code for β2GP1 and proteins that are expressed by those genes.

Within the context of the present disclosure, the β2GP1 polypeptide may be or comprise insertion, deletion, or substitution mutants of a known β2GP1 sequence or derivative thereof. Included as analogs, derivatives, and fragments of β2GP1 are polypeptides with conservative amino acid substitutions or non-conservative amino-acid substitutions, deletions, or insertions, which do not significantly reduce the anti-angiogenic activity of the β2GP1. Preferably, any substitution is conservative in that it minimally disrupts the biochemical properties and/or biologically functional properties of the β2GP1 polypeptide. Thus, where mutations are introduced to substitute amino acid residues, positively-charged residues (H, K, and R) are preferably substituted with positively-charged residues; negatively-charged residues (D and E) are preferably substituted with negatively-charged residues; neutral polar residues (C, G, N, Q, S, T, and Y) are preferably substituted with neutral polar residues; and neutral non-polar residues (A, F, I, L, M, P, V, and W) are preferably substituted with neutral non-polar residues. The present disclosure also includes β2GP1 attached to a carrier or ligand, or coupled to carbohydrates such as PEG or protein carriers as long as the β2GP1 retains anti-angiogenic activity.

In the methods of treatment disclosed herein, the administration of β2GP1 may be for either "prophylactic" or "therapeutic" purposes. When provided prophylactically, β2GP1 is provided in advance of any symptom. The prophylactic administration of β2GP1 serves to prevent or inhibit unwanted endothelial cell proliferation and/or angiogenesis at a site. When provided therapeutically, β2GP1 is provided at (or after) the onset of one or more symptoms or indications of unwanted endothelial cell proliferation and/or angiogenesis. Thus, β2GP1 may be provided either prior to the anticipated angiogenesis at a site or after angiogenesis has begun at a site.

Without being bound by any particular theory, β2GP1 may inhibit angiogenesis, in part, by attenuating the migration of endothelial cells, thus reducing or preventing neovascularization into a tissue. Thus, the disclosure provides a method of inhibiting endothelial cell migration by providing β2GP1 to such cells. Aside from attenuating angiogenesis, β2GP1 is useful for treating disorders associated with stimulation of endothelial cell migration such as intestinal adhesions, Crohn's disease, atherosclerosis, scleroderma, and hypertrophic scars (e.g., keloids). β2GP1 is also useful for treating pathological angiogenesis, which is characterized by the persistent proliferation of endothelial cells, and is a prominent feature of diseases such as, but not limited to, rheumatoid arthritis, scleroderma, lupus erythematosus, and psoriasis. Angiogenesis associated with wound repair may also be treated using β2GP1. Although controlled angiogenesis occurs during a variety of physiological processes, such as embryogenesis and wound repair, wound healing can be associated with excessive neovascularization and may result in keloid formation, excessive dermal scarring at sites of skin trauma or surgical sites, and other complications. Thus, it may appropriate in a number of circumstances to inhibit physiological neovascularization to prevent or alleviate complications of excessive neovascularization.

The present disclosure is useful in inhibiting angiogenic function of target cells, tissues, or organisms. In particular embodiments, at least one β2GP1 may be transfected into at least one cell, tissue, or organism. In particular aspects, the β2GP1 is transcribed, and in more specific aspects, translated into a protein, polypeptide or peptide in at least one cell, tissue, or organism. As used herein, the terms "cell," "cell line," and "cell culture" may be used interchangeably. All of these term also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector or construct and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

In the present disclosure, target cells may be endothelial cells, both in vitro and in vivo. β2GP1 can be provided to endothelial cells associated with the tissue of interest. As used herein, a tissue of interest includes, but is not limited to dermis, epidermis, endometrium, retina, surgical wound, gastrointestinal tract, umbilical cord, liver, kidney, reproductive system, lymphoid system, central nervous system, breast tissue, urinary tract, circulatory system, bone, muscle, respiratory tract, skin, endocrine system, brain, neoplasm, or tumor tissue. The endothelial cells can be cells in the tissue of interest, exogenous cells introduced into the tissue, or neighboring cells not within the tissue. Thus, for example, the cells can be cells of the tissue, with β2GP1 provided to them such that the β2GP1 contacts the cells. Alternatively, the cells can be introduced into the tissue, in which case the β2GP1 or an expression vector or construct of β2GP1 can be transferred to the cells before they are so introduced into the tissue (e.g., in vitro), as well as being transferred in situ after introduction into the tissue.

The cell or cells to be transformed with a β2GP1 vector or construct may be comprised in a tissue. The target tissue may be part or separated from an organism. In certain embodiments, a tissue may comprise, but is not limited to, skin, bone, neuron, axon, cartilage, blood vessel, cornea, muscle, fascia, brain, prostate, breast, endometrium, lung, pancreas, small intestine, blood, liver, testes, ovaries, cervix, colon, skin, stomach, esophagus, spleen, lymph node, bone marrow, kidney, peripheral blood, embryonic, ascite tissue, and all cancers thereof. Tissue with which endothelial cells are associated are also contemplated herein, and β2GP1 can be used in any tissue in which it is desired to inhibit the migration or expansion of endothelia (e.g., for inhibiting angiogenesis).

In certain embodiments, the cell or tissue may be comprised in at least one organism. In certain embodiments, the organism may be, but is not limited to, an eukaryote, an animal, a vertebrate, a primate (e.g., monkey, lemur, gorilla, chimp, human), a canine, a feline, a bovine, an equine, an ovine, a murine, a caprine, a porcine species, and the like.

A. Treatment of Angiogenic Diseases with β2GP1

A variety of tissues may be treated with β2GP1 to inhibit the proliferation, cord formation, cell migration, or differentiation of endothelial cells and/or angiogenesis. In a preferred embodiment, the tissue is a neoplasm (e.g., a cancerous tumor), in which β2GP1 inhibits the growth of blood vessels within and to the neoplasm. In another preferred embodiment, β2GP1 inhibits metastasis of the neoplasm. As used herein, the term "neoplasm" refers to any type of malignant or benign neoplasm, including any type of diffuse neoplasm such as leukemia, as well as malignant or benign cancers and tumors (including any carcinoma, sarcoma, or adenoma). A neoplasm is abnormal tissue that grows by cellular proliferation more rapidly than normal, and can continue to grow after the stimuli that initiated the new growth has ceased. A neoplasm may also have partial or complete lack of structural organization and functional coordination with normal tissue. Specifically contemplated neoplasms are, for example, tumors such as tumors of the mammary, pituitary, thyroid, prostate gland, brain, liver, meninges, bone, ovary, uterus, cervix, and the like.

Additional specifically contemplated neoplasms include, but are not limited to, adenocarcinoma, adenoma, astrocytoma, bladder tumor, bone carcinoma, brain carcinoma, Burkitt lymphoma, Kaposi Sarcoma, non-Hodgkins lymphoma, Hodgkins lymphoma, gastric tumor, breast carcinoma, cervical carcinoma, colon carcinoma, kidney carcinoma, liver carcinoma, lung carcinoma, ovarian carcinoma, pancreatic carcinoma, prostate carcinoma, rectal carcinoma, skin carcinoma, stomach carcinoma, testis carcinoma, thyroid carcinoma, chondrosarcoma, choriocarcinoma, fibroma, fibrosarcoma, glioblastoma, glioma, hepatoma, histiocytoma, leiomyoblastoma, leiomyosarcoma, leukemia, lymphoma, liposarcoma cell, mammary carcinoma, medulloblastoma, melanoma, metastases, muscle tumor, myeloma, ovarian carcinoma, plasmacytoma, neuroblastoma, neuroglioma, osteogenic sarcoma, pancreatic tumor, pituitary carcinoma, renal tumors, retinoblastoma, rhabdomyosarcoma, sarcoma, testicular tumor, thymoma, uterine carcinoma, Wilms' tumor, and the like.

Inhibiting the growth of blood vessels within a neoplasm will prevent sufficient nutrients and oxygen from being supplied to the neoplasm to support growth beyond a given size. Thus, β2GP1 can prevent the nucleation of neoplasms from cancerous cells already present due to genetic predisposition (e.g., BRCA-1 mutation carriers, Li Fraumeni patients with p53 mutations, etc.) or the presence of external carcinogens (e.g., tobacco, alcohol, industrial solvents, etc.). Aside from preventing neoplastic disease or tumerogenesis, β2GP1 can also retard the growth of existing neoplasms, thus rendering them more easily contained and excised. This application is highly advantageous for treating neoplasms that are difficult to operate on (e.g., brain or prostate tumors). Moreover, minimizing the number of blood vessels within an existing neoplasm lessens the probability that the neoplasm will metastasize.

In treating neoplasms, β2GP1 can be used alone or in conjunction with other therapeutic agents and/or treatments to control the growth of a neoplasm. Such therapies are particularly useful when the subject to be treated has a large preexisting tumor mass which is well vascularized. Indeed, employing β2GP1 can potentiate the response of some neoplasms to other therapeutic agents and/or treatments therapies. For example, the administration of β2GP1 optionally can be employed as a pretreatment for (e.g., for about a week in advance of), and/or continued during, a chemotherapeutic, anti-neoplastic, or radiation regimen. Additional therapeutic agents specifically contemplated by the present disclosure include but not limited to anti-neoplastic agents, chemotherapeutic agents, or even cocktails. Additional neoplastic therapies specifically contemplated by the present disclosure include but are not limited to surgery, chemotherapy, radiation therapy, pharmacotherapy, gene therapy, and immunotherapy treatments. Radiation therapy includes but is not limited to ionizing radiation; gamma radiation from radioactive isotopes such as cobalt-60, radium, radon, iridium, or electrically generated roentgen rays; radiation by external beam, implant, pellet, or seed; or variants thereof. β2GP1 may be administered to a patient before, during, and/or after other available neoplastic therapies. Additionally, separate administration of β2GP1 from the other therapeutic agents and/or treatments, or even an administration which is spaced in time, is contemplated by the present disclosure.

The present disclosure further encompasses methods for treating a neoplasm by administering to the subject a pharmaceutical composition that includes β2GP1 and one or more additional therapeutic agents, including but not limited to anti-neoplastic agents, chemotherapeutic agents, or even cocktails, to treat the neoplasm. Such a pharmaceutical composition may be used to inhibit, prevent, or suppress the growth of a neoplasm. The therapeutic agents used in combination with β2GP1 to treat a neoplasm can be presented to the subject in a separate formulation or as a mixture. Thus, separate administration of a therapeutic agent or even an administration which is spaced in time is contemplated by the present disclosure, particularly when the therapeutic agent and β2GP1 have a synergistic therapeutic action.

Examples of therapeutic agents useful in the treatment of neoplasms include, but are not limited to, taxol, tamoxifen, taxotere, doxorubicin, cisplatin, cyclophosphamide, gancyclovir, paclitaxel, methotrexate, mechlorethamine, aldesleukin, altretamine, amsacrine, azacitidine, ifosfamide, melphalan, chlorambucil, hexamethylmelamine, thiotepa, triethylenethiophosphoramide, busulfan, carmustine, lomustine, semustine, streptozocin, dacarbazine, fluorouacil, floxuridine, fludarabine, goserelin, cytarabine, levamisole, mercaptopurine, thioguanine, pentostatin, pipobroman, vinblastine, vincristine, vindesine, etoposide, teniposide, dactinomycin, daunorubicin, estramustine, filgrastim, bleomycin, plicamycin, uracil mustard, mitomycin, L-asparaginase, interferon-alpha, carboplatin, mitoxantrone, hydroxyurea, procarbazine, mitotane, aminoglutethimide, prednisone, hydroxyprogesterone caproate, medroxyprogesterone acetate, megastrol acetate, diethylstilbestrol, ethinyl estradiol, testosterone propionate, fluoxymesterone, flutamide, and leuprolide, an interferon, a tumor necrosis factor, a radiation implant such as a pellet or seed, or variants thereof.

In treating neoplasms, β2GP1 can also be used alone or in conjunction with other antiangiogenic agents to control the growth of a neoplasm. Indeed, employing β2GP1 and one or more additional antiangiogenic agents may potentiate the response of some neoplasms to these agents. Additional antiangiogenic agents specifically contemplated by the present disclosure include but not limited to angiostatin, endostatin, trastuzumab, TGF-β, thrombospondin, IL-1, IFN-γ, IFN-α, tissue inhibitor of metalloproteinase-1 (TIMP-1), platelet factor 4 (PF4), protamine, retinoic acid, AGM-1470, fumagillin, tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interleukin-12, pentosan polysulfate, a cyclooxygenase inhibitor, fibronectin, laminin, prolactin, carboxyamidotriazole, combretastatin A-4, squalamine, 6-O-chloroacetyl-carbonyl)-fumagillol, thalidomide, troponin-1, and an antibody to VEGF In addition, β2GP1 can be used in conjunction with antibodies and polypeptides that block integrin engagement, proteins and small molecules that inhibit metalloproteinases (e.g., marmistat), agents that block phosphorylation cascades within endothelial cells (e.g., herbamycin), dominant negative receptors for known inducers of angiogenesis, anti-inflammatory agents (e.g., ibuprofen, aspirin, prednisone), antibodies against inducers of angiogenesis or other compounds that block their activity (e.g., suramin), or other compounds (e.g., retinoids, IL-4, interferons, etc.) acting by other means. Indeed, because other antiangiogenic factors may inhibit angiogenesis by different mechanisms, employing β2GP1 in combination with other antiangiogenic agents may potentiate a more potent (and potentially synergistic) inhibition of angiogenesis within the desired tissue. β2GP1 may be administered to a patient before, during, and/or after the administration of other available antiangiogenic agents to a subject. Additionally, separate administration of β2GP1 from the other antiangiogenic agents, or even an administration which is spaced in time, is contemplated by the present disclosure.

The present disclosure further encompasses methods for treating a neoplasm by administering to the subject a pharmaceutical composition that includes β2GP1 and one or more additional antiangiogenic agents to treat the neoplasm. Such a pharmaceutical composition may be used to inhibit, prevent, or suppress the growth of a neoplasm. The antiangiogenic agents used in combination with β2GP1 to treat a neoplasm can be presented to the subject in a separate formulation or as a mixture. Thus, separate administration of a antiangiogenic agent or even an administration which is spaced in time is contemplated by the present disclosure, particularly when the antiangiogenic agent and β2GP1 have a synergistic therapeutic action.

Where β2GP1 is applied to other tissues, the prevention of neovascularization effectively treats a host of disorders. Thus, for example, β2GP1 can be used as part of a treatment for disorders of blood vessels (e.g., hemangiomas and capillary proliferation within atherosclerotic plaques), muscle diseases (e.g., myocardial angiogenesis or angiogenesis within smooth muscles), joints (e.g., arthritis, hemophiliac joints, etc.), and other disorders associated with angiogenesis (e.g., Osler-Webber Syndrome, plaque neovascularization, telangiectasia, angiofibroma, wound granularization, etc.).

In one embodiment, the tissue can be eye tissue, in which case the presence of β2GP1 will inhibit novel angiogenesis associated with a variety of disorders of the eye. For example, β2GP1 is useful for treating eye injury, hypoxia, infection, surgery, laser surgery, diabeties, retinoblastoma, or other diseases or disorders of the eye. In this respect, the method is useful for preventing blindness or retarding loss of vision associated with a variety of eye diseases.

In another embodiment, the tissue is skin tissue, in which case the presence of β2GP1 prevents neovascularization associated with several skin diseases. For example, the inventive method is useful for treating diseases and disorders such as psoriasis, scleroderma, tumors of the skin, neovascularization as a consequence of infection (e.g., cat scratch disease, bacterial ulceration, etc.), or other skin disorders. Where β2GP1 is provided to the skin, it can be provided to the surface of the skin or to skin tissue beneath the skin's surface. Furthermore, transfer of β2GP1 to skin of a mammal may also stimulate the growth of hair in the skin.

The present disclosure also provides a method for determining the prognosis of a tumor by assaying for the presence of β2GP1 within the tumor. The method involves obtaining tissue or fluid from the tumor and detecting the presence or absence of β2GP1 within the tissue or fluid. Greater β2GP1 concentration within the tumor may correlate with a lesser likelihood that the tumor is undergoing angiogenesis, depending on the tumor assayed. The method can employ an assay for the presence of β2GP1 gene expression (e.g., via rtPCR, Northern hybridization, in situ hybridization, etc.). Alternatively, the method can employ an assay for the presence of β2GP1 polypeptides (e.g., immunological assays, β2GP1 purification and PAGE analysis, etc.).

B. β2GP1 Proteins, Polypeptides, and Peptides

As discussed herein, β2GP1 is a polypeptide. Contemplated by the present disclosure are methods for providing β2GP1 by supplying a β2GP1 polypeptide to cells, tissues, or organisms of interest (e.g., within a suitable composition). Any suitable method known to those of skill in the art can be employed to obtain a β2GP1 polypeptide for use in the present disclosure, and β2GP1 may be obtained from natural, recombinant, or synthetic sources. For example, β2GP1 can be purified from animal plasma, or β2GP1 can be produced recombinantly, chemically, or enzymatically.

A particularly good source of naturally occurring β2GP1 is human plasma. Plasma can be obtained from regional blood centers without regard to race, gender, or ethnic background. Examples of protocols for purifying β2GP1 from human plasma known to those of skill in the art include but are not limited to perchloric acid precipitation, ion-exchange, and heparin affinity chromatography (Wurm, H., *Int. J. Biochem.* 16:511–515, 1984; Polz et al., *Int. J. Biochem.* 11:265–270, 1980; Schousboe, I., *Biochim. Biophys. Acta* 579:396–408, 1979; incorporated herein by reference). N-β2GP1 (Lys-317/Thr-318) may also be prepared using techniques known to those of skill in the art. For example, N-β2GP1 can be isolated from human plasma (see Horbach et al., *Throm. Haemostasis* 81:87–95, 1999, incorporated herein by reference), or N-β2GP1 may be prepared from plasmin and purified by an additional heparin affinity chromatography step (Horbach et al, *Throm. Haemostasis* 81:87–95, 1999; Ohkura et al., *Blood* 91:4173–4179, 1998; incorporated herein by reference). Additionally, N-β2GP1 can also be prepared by proteolytically cleaving intact β2GP1 at Lys-317 and Thr-318 in vitro with the enzymes factor Xa or elastase. Unwanted proteolytic cleavage of intact β2GP1 at Lys-317 and Thr-318 can be prevented by, for example, pretreating plasma with perchloric acid precipitation. Other protocols for purifying β2GP1 polypeptides are known in the art.

Yet another method of producing β2GP1, or biologically active fragments thereof, is by peptide synthesis. A β2GP1 polypeptide is identified via SDS-PAGE as a protein of about 50 kDa. β2GP1 polypeptides can be synthesized using standard direct peptide synthesizing techniques known to those of skill in the art, such as via solid-phase synthesis (see, e.g., Barany et al., *Int. J. Peptide Protein Res.*, 30:705–739, 1987; U.S. Pat. No. 5,424,398; Solid Phase Peptide Synthesis: A Practical Approach E. Atherton and R. C. Sheppard, IRL Press, Oxford England; incorporated herein by reference). Similarly, multiple fragments can be synthesized which are subsequently linked together to form larger fragments.

The present disclosure provides for purified, and in preferred embodiments, substantially purified, β2GP1 polypeptides. As used herein the term "β2GP1 polypeptide" includes β2GP1 proteins, polypeptides, or peptides. The term "purified β2GP1 polypeptides" as used herein is intended to refer to a β2GP1 proteinaceous composition, isolatable from natural, recombinant, or synthetic sources, wherein the β2GP1 polypeptide is purified to any degree relative to its naturally-obtainable state, i.e., relative to its purity within a cellular extract. As used herein, the term "proteinaceous composition" encompasses the terms protein, polypeptide, and peptide. A β2GP1 polypeptide therefore also refers to a wild-type or mutant β2GP1 polypeptide free from the environment in which it naturally occurs. As used herein "wild-type" refers to the naturally occurring sequence of a nucleic acid at a genetic locus in the genome of an organism, or a sequence transcribed or translated from such a nucleic acid. The term "wild-type" also may refer to an amino acid sequence encoded by a nucleic acid. Since a genetic locus may have more than one sequence or alleles in a population of individuals, the term "wild-type" encompasses all such naturally occurring allele(s). The β2GP1 polypeptides may be full length proteins, for example 326 amino acids in length, or they may also be less then full length proteins, such as individual domains, regions, or even epitopic peptides. The most preferred less than full length β2GP1 proteins are those containing predicted immunogenic sites and those containing the functional domains identified herein.

Generally, "purified" will refer to a β2GP1 polypeptide composition that has been subjected to fractionation to remove various non-β2GP1 polypeptides, and which composition substantially retains its β2GP1 antiangiogenic activity. The term "substantially purified" refers to a composition in which the β2GP1 polypeptide forms the major component of the composition, such as constituting about 50% of the proteins in the composition or more. In preferred embodiments, a substantially purified protein will constitute more than 60%, 70%, 80%, 90%, 95%, 99%, or even more of the proteins in the composition. A polypeptide that is "purified to homogeneity," as applied to the present disclosure, means that the polypeptide has a level of purity where the polypeptide is substantially free from other proteins and biological components. For example, a purified polypeptide will often be sufficiently free of other protein components so that degradative sequencing may be performed successfully.

Various methods for quantifying the degree of purification of β2GP1 polypeptides will be known to those of skill in the art in light of the present disclosure. These include, for example, determining the specific β2GP1 protein activity of a fraction, or assessing the number of polypeptides within a fraction by gel electrophoresis. Assessing the number of polypeptides within a fraction by SDS/PAGE analysis will often be preferred in the context of the present disclosure because it is a straightforward protocol. The activity of a fraction may also be determined by a number of methods known to those of skill in the art, including but not limited to affinity chromatography, gelatin enzymography, or zymography.

To purify a β2GP1 polypeptide, a natural or recombinant composition comprising at least some β2GP1 polypeptide will be subjected to fractionation to remove various non-β2GP1 components from the composition. Techniques suitable for use in protein purification are well known to those of skill in the art. These include, for example, precipitation with ammonium sulfate, PEG, antibodies and the like or by heat denaturation, followed by centrifugation; chromatography steps such as ion exchange, gel filtration, reverse phase, hydroxylapatite, lectin affinity and other affinity chromatography steps; isoelectric focusing; gel electrophoresis; and combinations of such and other techniques. Additionally, recombinant β2GP1 may be purified from cell-free lysates by affinity chromatography on anti-β2GP1-sepharose. Another example is the purification of β2GP1 fusion proteins using specific binding partners. Such purification methods are routine in the art. Since DNA coding sequences sequences for β2GP1 are known, any fusion protein purification method can be practiced.

Isolated β2GP1 polypeptides can be conclusively identified by N-terminal amino acid sequencing (intact β2GP1: single N-terminal sequence (GRTCPK . . . ); N-β2GP1: two N-terminal sequences (GRCPTK . . . and TDASD . . . )). β2GP1 polypeptides can also be labeled using a variety of methods known to those of skill in the art. For example, polypeptides can be labeled by iodination with $^{125}$I using iodogen or iodobeads as previously described (Ma et al., *J. Biol. Chem.* 275:15541–15548, 2000; incorporated herein by reference) or by direct coupling to appropriately activated (N-hydroxysuccinimide-, maleimide- or hydrazine-) fluorophores. β2GP1 binds endothelial cells through annexin II, which can be purified as described in Khanna et al., *Biochemistry* 29:4852–4862, 1990, incorporated herein by reference.

C. Recombinant Vectors, Host Cells and Expression

Recombinant vectors form important further aspects of the present disclosure. In methods disclosed herein, β2GP1 polypeptide can be provided to a cell, tissue, or organism of interest by transferring an expression vector or construct that includes a nucleic acid encoding β2GP1 to cells associated with the tissue or organism of interest. The term "expression vector or construct" refers to any type of genetic construct containing a nucleic acid coding for a gene product in which part or all of the nucleic acid encoding sequence is capable of being transcribed. The transcript may be translated into a protein, but it need not be. Thus, in certain embodiments, expression includes both transcription of a gene and translation of a RNA into a gene product. An expression vector or construct may include any desired DNA sequence that can be incorporated into the genome of a cell, including but not limited to genes or DNA sequences that are not normally present in the genome, genes or DNA sequences that are normally present, but are not normally transcribed and translated ("expressed") in a given genome, or any other genes or DNA sequences that one desires to introduce into the genome. This may include genes or DNA sequences that are normally present in the genome of the cell, tissue, or organism of interest, but which one desires to have altered in expression, or which one desires to introduce in an altered or variant form.

Methods for producing β2GP1 polypeptide recombinantly are well to those of skill in the art. One example of a method for producing β2GP1 using recombinant DNA techniques entails the steps of (1) inserting the β2GP1 gene or cDNA into an appropriate vector such as an expression vector, (2) inserting the gene-containing vector into a microorganism or other expression system capable of expressing the β2GP1 gene, and (3) isolating the recombinantly produced β2GP1. The above techniques are more fully described in laboratory manuals such as Sambrook et al. (1989), supra, incorporated herein by reference. Examples of methods for generating recombinant β2GP1 are disclosed in Kouts et al., *FEBS Lett.* 326:105–108, 1993; Chen et al., *Chinese Med. J.* 112:67–71, 1999; and Kristensen et al., *FEBS Lett.* 289:183–186, 1991, incorporated herein by reference.

Any suitable vector or construct can be employed as a recombinant vector, many of which are known in the art. Examples of such vectors include but are not limited to naked DNA vectors (such as oligonucleotides or plasmids), viral vectors such as adeno-associated viral vectors (Bern and Giraud, *Ann. N.Y. Acad. Sci.* 772:95–104, 1995; incorporated herein by reference), adenoviral vectors (Bain et al., *Gene Therapy Suppl.* 1;S68, 1994; incorporated herein by reference), herpesvirus vectors (Fink et al., *Ann. Rev. Neurosci.* 19:265–87, 1996; incorporated herein by reference), packaged amplicons (Carew et al., *Mol. Ther.* 4:250–256, 2001; incorporated herein by reference), pappiloma virus vectors, picornavirus vectors, polyoma virus vectors, retroviral vectors, SV40 viral vectors, vaccinia virus vectors, and the like.

In one embodiment, the expression vector or construct will be introduced into the cell, tissue, or organism of interest to produce and secrete the β2GP1 polypeptide, for example, to endothelial cells within the tissue, such that angiogenesis is inhibited or attenuated within the tissue or organism of interest. Coding sequences for β2GP1 genes, cDNAs, and polypeptides are known, and others can be deduced from the genetic sequences discussed herein. Thus, β2GP1 expression vectors or constructs will typically employ coding sequences homologous to these known sequences, e.g., they will hybridize to at least a fragment of the known sequences under at least mild stringency conditions, more preferably under moderate stringency conditions, most preferably under high stringency conditions (employing the definitions of mild, moderate, and high stringency as set forth in Sambrook et al., (1989) Molecular Cloning: A Laboratory Manual, 2d ed., 1989, Cold Spring Harbor Laboratory Press, Cold Spring Harbor, N.Y., incorporated herein by reference).

In addition to the β2GP1 coding sequence, an expression vector or construct may include regulatory elements that drive expression of β2GP1 by providing transcriptional and translational initiation regions associated with gene expression in the cell or tissue of interest, and functional transcriptional and translational termination regions. Particularly useful vectors or constructs are contemplated to be those in which the coding portion of the DNA segment, whether encoding a full length protein, polypeptide, or smaller peptide, is positioned under the transcriptional control of a promoter. A "promoter" refers to a DNA sequence recognized by the transcriptional machinery of the cell, or introduced transcriptional machinery, required to initiate the specific transcription of a gene. The phrases "operatively positioned," "under control," or "under transcriptional control" means that the promoter is in the correct location and orientation in relation to the nucleic acid to control RNA polymerase initiation and expression of the gene. As used herein, the term "operable linkage" refers to a linkage of polynucleotide elements in a functional relationship.

For example, a promoter or enhancer is in operable linkage to a coding sequence if it affects and/or regulates the transcription of the coding sequence. As long as this operable linkage is maintained, the expression cassette can include more than one gene, such as multiple genes separated by ribosome entry sites. The promoter may be in the form of the promoter that is naturally associated with a β2GP1 gene, as may be obtained by isolating the 5' non-coding sequences located upstream of the coding segment or exon, for example, using recombinant cloning and/or PCR™ technology (PCR™ technology is disclosed in U.S. Pat. No. 4,683,202 and U.S. Pat. No. 4,682,195, incorporated herein by reference).

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a β2GP1 gene in its natural environment. Such promoters may include promoters normally associated with other genes, and/or promoters isolated from any other bacterial, viral, eukaryotic, or mammalian cell, and/or promoters that are not "naturally occurring," i.e., containing difference elements from different promoters, or mutations that increase, decrease, or alter expression.

Naturally, it will be important to employ a promoter that effectively directs the expression of the DNA segment in the cell type, tissue, or organism chosen for expression. The use of promoter and cell type combinations for protein expression is generally known to those of skill in the art of molecular biology, for example, see Sambrook et al. (1989), supra, incorporated herein by reference. The promoters employed may be constitutive, or inducible, and can be used under the appropriate conditions to direct high level expression of the introduced DNA segment, such as is advantageous in the large-scale production of recombinant proteins or peptides. Promoters of varying strength in terms of their ability to drive expression may also be used to drive expression of the β2GP1 gene.

At least one module in a promoter generally functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30–110 base pairs (bp) upstream of the start site, although a number of promoters have been shown to contain functional elements downstream of the start site as well. The spacing between promoter elements frequently is flexible, so that promoter function is preserved when elements are inverted or moved relative to one another. Depending on the promoter, it appears that individual elements can function either co-operatively or independently to activate transcription.

The particular promoter that is employed to control the expression of a nucleic acid is not believed to be critical, so long as it is capable of expressing the nucleic acid in the targeted cell. Thus, where a human cell or tissue is targeted, it is preferable to position the nucleic acid coding region adjacent to and under the control of a promoter that is capable of being expressed in that human cell or tissue. Generally speaking, such a promoter might include either a human or viral promoter.

Several different types of promoters may be used to drive expression of β2GP1, including a promoter from a naturally-occurring heterologous gene, a promoter from an endogenous β2GP1 gene, tissue-specific, developmental pattern, or cell-type-specific promoters, or a transcriptional regulatory element heterogenous with respect to both the β2GP1 encoding sequences and the host cell or tissue type. Many viral promoters are appropriate for use in an expression vector or construct to obtain high-level expression of β2GP1 (e.g., retroviral ITRs, LTRs, immediate early viral promoters (IEp) (such as herpesvirus IEp (e.g., ICP4-IEp and ICP0-IEp), cytomegalovirus (CMV)IEp, and the SV40 early promoter), and other viral promoters (e.g., late viral promoters, latency-active promoters (LAPs), Rous Sarcoma Virus (RSV) promoters, and Murine Leukemia Virus (MLV) promoters)). Other suitable promoters are eukaryotic promoters, such as enhancers (e.g., the rabbit β-globin regulatory elements), constitutively active promoters (e.g., the β-actin promoter, etc.), signal specific promoters (e.g., inducible and/or repressible promoters, such as a promoter responsive to TNF or RU486, the metallothionine promoter, etc.), and tumor-specific promoters. The use of other viral or mammalian cellular or bacterial phage promoters which are well-known in the art to achieve expression are contemplated as well, provided that the levels of expression are sufficient for a given purpose. This list of is not intended to be exhaustive of all the possible elements involved in the promotion of expression but, merely, to be exemplary thereof.

The expression or vector construct can also include other genetic elements, for example, polyadenylation sequences, transcriptional regulatory elements (e.g., enhancers, silencers, etc.), or other sequences. An enhancer is a regulatory DNA sequence that is capable of activating transcription from a promoter linked to it. Enhancers can function in both orientations either upstream or downstream of a promoter. Some embodiments will employ transcriptional regulatory sequences which confer high level expression and/or a cell-type-specific expression pattern. Enhancers were originally detected as genetic elements that increased transcription from a promoter located at a distant position on the same molecule of DNA. Subsequent work showed that regions of DNA with enhancer activity are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Additionally, any promoter/enhancer combination (as per the Eukaryotic Promoter Data Base EPDB) could also be used to drive expression. Use of a T3, T7, or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

The expression vector or construct may also take advantage of endogenous regulatory elements in the genome of the particular cells or tissue of interest, by integrating into a chromosomal location containing functional endogenous regulatory elements that are suitable for the expression of β2GP1 sequences. Endogenous regulatory elements include sequences that are natural to the host cell, tissue, or organism, as well as sequences present in the host as a result of an infectious disease, e.g. virus, prion, and the like. The expression vector or construct may integrate into the genome via nonhomologous integration or targeted homologous recombination, or the expression vector or construct may express β2GP1 without integrating into the genome.

Expression vectors or constructs contemplated herein can also include other genetic elements, such as, for example, genes encoding a selectable marker (e.g., β-gal or a marker conferring resistance to a toxin), a pharmacologically active protein, a transcription factor, or other biologically active substance. Positive selection expression cassettes used in a vector or construct encode a selectable marker that affords a means for selecting cells that have integrated the vector transgene sequence spanning the positive selection expression cassette. Suitable drug resistance genes are well known to those of skill in the art and include but are not limited to: gpt (xanthine-guanine phosphoribosyltransferase), which can be selected for with mycophenolic acid; neo (neomycin phosphotransferase), which can be selected for with G418 or hygromycin; and DFHR (dihydrofolate reductase), which can be selected for with methotrexate (Mulligan and Berg, (1981) *Proc. Natl. Acad. Sci. USA* 78:2072; Southern and Berg, (1982) *J. Mol. Appl. Genet.* 1:327). Positive selection involves expression of the selectable marker, which encodes a functional protein (e.g., neo or gpt) that confers a selectable phenotype to targeted cells or tissue that harbor the endogenously integrated expression cassette, such that by addition of a selection agent (e.g., G418 or mycophenolic acid), targeted cells have a growth or survival advantage over cells that do not have an integrated expression cassette.

The β2GP1 coding sequence present in a suitable expression vector or construct may be a cDNA sequence, genomic DNA sequence, or the coding sequence may include one or more introns. Many genes or cDNAs that encode β2GP1 polypeptides are known in the art, or can be deduced from known polypeptide sequences. Once a suitable clone or clones of β2GP1 coding sequences have been obtained, whether they be cDNA or genomic sequences, an expression system may be prepared. The engineering of DNA segments for expression in a prokaryotic or eukaryotic system may be performed by techniques generally known to those of skill in recombinant expression.

It is believed that virtually any expression system may be employed in the expression of the proteins of the present disclosure. Both cDNA and genomic sequences are suitable for eukaryotic expression, as the host cell will generally process the genomic transcripts to yield functional mRNA for translation into protein. Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude or more larger than the cDNA gene. However, it is contemplated that a genomic version of a particular gene may be employed where desired.

In expression, typically a polyadenylation signal is included to effect proper polyadenylation of the transcript. The nature of the polyadenylation signal is not believed to be crucial to the successful practice of the disclosure, and any such sequence may be employed. Preferred embodiments include the SV40 polyadenylation signal and the bovine growth hormone polyadenylation signal, convenient and known to function well in various target cells. Also contemplated as an element of the expression cassette is a terminator. These elements can serve to enhance message levels and to minimize read through from the expression cassette into other sequences.

A specific initiation signal also may be required for efficient translation of coding sequences. These signals include the ATG initiation codon and adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

It is proposed that β2GP1 proteins, polypeptides, or peptides may be co-expressed with other selected proteins, wherein the proteins may be co-expressed in the same cell or a β2GP1 gene may be provided to a cell that already expresses another selected protein. Co-expression may be achieved by co-transfecting the cell with two distinct recombinant vectors, each bearing a copy of either of the respective DNA. Alternatively, a single recombinant vector may be constructed to include the coding regions for both of the proteins, which could then be expressed in cells transfected with the single vector. In either event, the term "co-expression" herein refers to the expression of both β2GP1 and the other selected protein in the same recombinant cell.

As used herein, the terms "engineered" and "recombinant" cells or host cells are intended to refer to a cell into which an exogenous DNA segment or gene, such as a cDNA or gene encoding a β2GP1 polypeptide, has been introduced. Therefore, engineered cells are distinguishable from naturally occurring cells which do not contain a recombinantly introduced exogenous DNA segment or gene. Recombinant cells include those having an introduced cDNA or genomic gene, and also include genes positioned adjacent to a promoter not naturally associated with the particular introduced gene. To express a recombinant β2GP1 protein, polypeptide, or peptide, whether mutant or wild-type, in accordance with the present disclosure, one would prepare an expression vector that comprises a wild-type, or mutant β2GP1 protein-encoding nucleic acid under the control of one or more promoters. In general, to bring a coding sequence under the control of a promoter, one positions the 5' end of the transcription initiation site of the transcriptional reading frame between about 1 and about 50 nucleotides "downstream" of (i.e., 3' of) the chosen promoter. The "upstream" promoter stimulates transcription of the DNA and promotes expression of the encoded recombinant protein. This is the meaning of "recombinant expression" in this context.

Many standard techniques are available to construct expression vectors containing the appropriate nucleic acids and transcriptional/translational control sequences in order to achieve protein, polypeptide, or peptide expression in a variety of host-expression systems. Once a given type of vector or construct is selected, its genome must be manipulated for use as a background vector, after which it must be engineered to incorporate exogenous polynucleotides. Methods for manipulating the genomes of vectors are well known in the art (see, e.g., Sambrook et al., supra), and include direct cloning, site specific recombination using recombinases, homologous recombination, and other suitable methods of constructing a recombinant vector. Vectors containing a targeting construct are typically grown in *E. coli* and then isolated using standard molecular biology methods, or may be synthesized as oligonucleotides.

Host cells may be derived from prokaryotes or eukaryotes, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials (www.atcc.org). In certain embodiments, a cell may comprise, but is not limited to, at least one skin, bone, neuron, axon, cartilage, blood vessel, cornea, muscle, fascia, brain, prostate, breast, endometrium, lung, pancreas, small intestine, blood, liver, testes, ovaries, cervix, colon, skin, stomach, esophagus, spleen, lymph node, bone marrow, kidney, peripheral blood, embryonic or ascite cell, and all cancers thereof. An appropriate host can be determined by one of skill in the art based on the vector backbone and the desired result.

Cell types available for expression include, but are not limited to, bacteria, such as *E. coli* and *B. subtilis* transformed with recombinant bacteriophage DNA, plasmid DNA, or cosmid DNA expression vectors. Certain examples of prokaryotic hosts are *E. coli* strain RR1, *E. coli* LE392, *E. coli* B, *E. coli* X 1776 (ATCC No. 31537) as well as *E. coli* W3110 (F-, lambda-, prototrophic, ATCC No. 273325); bacilli such as *Bacillus subtilis*; and other enterobacteriaceae such as *Salmonella typhimurium*, *Serratia marcescens*, and various *Pseudomonas* species. Additional bacterial cells used as host cells for vector replication and/or expression include DH5a, JM109, and KC8, as well as a number of commercially available bacterial hosts such as SURE® Competent Cells and SOLOPACKTm Gold Cells (STRATAGENE©, La Jolla). Alternatively, bacterial cells such as *E. coli* LE392 could be used as host cells for phage viruses. Examples of eukaryotic host cells for replication and/or expression of a vector include HeLa, NIH3T3, Jurkat, 293, Cos, Chinese hamster ovary (CHO), Saos, PC 12, and S2 cells. Many host cells from various cell types and organisms are available and would be known to one of skill in the art.

Some β2GP1 may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is often transformed using derivatives of pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own proteins. Additionally, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as *E. coli* LE392.

Further useful vectors include pIN vectors (Inouye et al., 1985); and pGEX vectors, for use in generating glutathione S-transferase (GST) soluble fusion proteins for later purification and separation or cleavage. Other suitable fusion proteins are those with O-galactosidase, ubiquitin, and the like. Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

The following details concerning recombinant protein production in bacterial cells, such as *E. coli*, are provided by way of exemplary information on recombinant protein production in general, the adaptation of which to a particular recombinant expression system will be known to those of skill in the art. Bacterial cells, for example, *E. coli*, containing the expression vector are grown in any of a number of suitable media, for example, LB. The expression of the recombinant protein may be induced, e.g., by adding IPTG to the media or by switching incubation to a higher temperature. After culturing the bacteria for a further period, generally of between 2 and 24 h, the cells are collected by centrifugation and washed to remove residual media. The bacterial cells are then lysed, for example, by disruption in a cell homogenizer and centrifuged to separate the dense inclusion bodies and cell membranes from the soluble cell components. This centrifugation can be performed under conditions whereby the dense inclusion bodies are selectively enriched by incorporation of sugars, such as sucrose, into the buffer and centrifugation at a selective speed.

If the recombinant protein is expressed in the inclusion bodies, as is the case in many instances, these can be washed in any of several solutions to remove some of the contaminating host proteins, then solubilized in solutions containing high concentrations of urea (e.g. 8M) or chaotropic agents such as guanidine hydrochloride in the presence of reducing agents, such as (β-mercaptoethanol or DTT (dithiothreitol). Under some circumstances, it may be advantageous to incubate the protein for several hours under conditions suitable for the protein to undergo a refolding process into a conformation which more closely resembles that of the native protein. Such conditions generally include low protein concentrations, for example, less than 500 mg/ml, low levels of reducing agent, concentrations of urea less than 2 M and often the presence of reagents such as a mixture of reduced and oxidized glutathione which facilitate the interchange of disulfide bonds within the protein molecule. The refolding process can be monitored, for example, by SDS-PAGE, or with antibodies specific for the native molecule (which can be obtained from animals vaccinated with the native molecule or smaller quantities of recombinant protein). Following refolding, the protein can then be purified further and separated from the refolding mixture by chromatography on any of several supports including ion exchange resins, gel permeation resins, or on a variety of affinity columns.

For expression in Saccharomyces, the plasmid YRp7, for example, is commonly used. This plasmid already contains the trp1 gene which provides a selection marker for a mutant strain of yeast lacking the ability to grow in tryptophan, for example ATCC No. 44076 or PEP4-1. The presence of the trp1 lesion as a characteristic of the yeast host cell genome then provides an effective environment for detecting transformation by growth in the absence of tryptophan. Suitable promoting sequences in yeast vectors include the promoters for 3-phosphoglycerate kinase or other glycolytic enzymes, such as enolase, glyceraldehyde-3phosphate dehydrogenase, hexokinase, pyruvate decarboxylase, phosphofructokinase, glucose-6phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other suitable promoters, which have the additional advantage of transcription controlled by growth conditions, include the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In addition to micro-organisms, cultures of cells derived from multicellular organisms may also be used as hosts, and are known to those of skill in the art. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV), or transformed with recombinant plasmid expression vectors (e.g., Ti plasmid) containing one or more β2GP1 protein, polypeptide, or peptide coding sequences. Examples of useful mammalian host cell lines are VERO and HeLa cells, Chinese hamster ovary (CHO) cell lines, W138, BHK, COS-7, 293, HepG2, 3T3, RIN and MDCK cell lines. Additionally, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed.

Expression vectors for use in mammalian cells ordinarily include an origin of replication (as necessary), a promoter located in front of the gene to be expressed, along with any necessary ribosome binding sites, RNA splice sites, poly-adenylation site, and transcriptional terminator sequences. The origin of replication may be provided either by construction of the vector to include an exogenous origin, such as may be derived from SV40 or other viral (e.g., Polyoma, Adeno, VSV, BPV) sources, or may be provided by the host cell chromosomal replication mechanism. If the vector is integrated into the host cell chromosome, the latter is often sufficient. The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with β2GP1 gene sequence(s), provided such control sequences are compatible with the host cell systems.

A number of viral based expression systems may be utilized, for example, commonly used promoters are derived from polyoma, Adenovirus 2, and most frequently Simian Virus 40 (SV40). The early and late promoters of SV40 virus are particularly useful because both are obtained easily from the virus as a fragment, which also contains the SV40 viral origin of replication. In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1, E3, or E4) will result in a recombinant virus that is viable and capable of expressing β2GP1 proteins, polypeptides, or peptides in infected hosts.

Specific initiation signals may also be required for efficient translation of β2GP1 protein, polypeptide, or peptide coding sequences. These signals include the ATG initiation codon and adjacent sequences. Exogenous translational control signals, including the ATG initiation codon, may also need to be provided. One of ordinary skill in the art would readily be capable of determining this and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements and transcription terminators. In eukaryotic expression, one will also typically desire to incorporate into the transcriptional unit an appropriate polyadenylation site (e.g., 5'-AATAAA-3'), particularly if one is not contained within the original cloned segment. Typically, the poly A addition site is placed about 30 to 2000 nucleotides "downstream" of the termination site of the protein at a position prior to transcription termination.

For long-term, high-yield production of a recombinant β2GP1 protein, polypeptide, or peptide, stable expression is preferred. For example, cell lines that stably express constructs encoding a β2GP1 protein, polypeptide, or peptide may be engineered. Rather than using expression vectors or constructs that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells are allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including, but not limited to, the herpes simplex virus thymidine kinase (tk), hypoxanthine-guanine phosphoribosyltransferase (hgprt) and adenine phosphoribosyltransferase (aprt) genes, in tk−, hgprt− or aprt− cells, respectively. Also, antimetabolite resistance can be used as the basis of selection for dihydrofolate reductase (dhfr), that confers resistance to methotrexate; gpt, that confers resistance to mycophenolic acid; neomycin (neo), that confers resistance to the aminoglycoside G-418; and hygromycin (hygro), that confers resistance to hygromycin.

Animal cells can be propagated in vitro in two modes: as non-anchorage dependent cells growing in suspension throughout the bulk of the culture or as anchorage-dependent cells requiring attachment to a solid substrate for their propagation (i.e., a monolayer type of cell growth). Nonanchorage dependent or suspension cultures from continuous established cell lines are the most widely used means of large scale production of cells and cell products. Suspension cultured cells have limitations, however, such as tumorigenic potential and lower protein production than adherent cells.

Large scale suspension culture of mammalian cells in stirred tanks is a common method for production of recombinant proteins. Two suspension culture reactor designs are in wide use the stirred reactor and the airlift reactor. The stirred design has successfully been used on an 8000 liter capacity for the production of interferon. Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts. The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively easily, has good mass transfer of gases, and generates relatively low shear forces.

In order to effect expression of gene constructs, the expression construct must be delivered into a cell. Viral vectors are best transferred into the cells by infecting them; however, the mode of infection can vary depending on the virus. This delivery may be accomplished in vitro, as in laboratory procedures for transforming cells lines, or in vivo or ex vivo (see below), as in the treatment of certain disease states. The preferred mechanism for delivery is via viral infection where the expression construct is encapsidated in an infectious viral particle. Several non-viral methods for the transfer of expression constructs into cultured mammalian cells are also contemplated by the present disclosure. Expression vectors or constructs can be introduced or transferred to cells or tissues of interest by any one of many known suitable techniques, including but not limited to microinjection, biolistics, calcium phosphate precipitation (Graham and Van Der Eb, *Virology* 54:536–539, 1973; Chen and Okayama, *Mol. Cell Biol.* 7:2745–2752, 1987; Rippe et al., *Mol. Cell Biol.* 10:689–695, 1990, incorporated herein by reference) DEAE-dextran (Gopal, *Mol. Cell Biol.* 5:1188–1190, 1985, incorporated herein by reference), electroporation (Tur-Kaspa et al., *Mol. Cell Biol.* 6:716–718, 1986; Potter et al., *Proc. Natl. Acad. Sci.* (USA) 81:7161–7165, 1984, incorporated herein by reference), direct microinjection (Harland and Weintraub, *J. Cell Biol.* 101:1094–1099, 1985, incorporated herein by reference), DNA-loaded liposomes (Nicolau and Sene, *Biochim. Biophys. Acta* 721:185–190, 1982; Fraley et al., *J. Biol. Chem.* 255:10431–10435, 1980, incorporated herein by reference) and lipofectamine-DNA complexes, cell sonication (Fechheimer et al., *Proc. Natl. Acad. Sci.* (USA) 84:8463–8467, 1987, incorporated herein by reference), gene bombardment using high velocity microprojectiles (Fitzpatrick-McElligott, *Biotechnology* 10:1036–1040, 1992, incorporated herein by reference), receptor-mediated transfection (Wu and Wu, *J. Biol. Chem.* 263:14621–14624, 1988; Wu and Wu, *Biochemistry* 27:887–892, 1988, incorporated herein by reference), gene gun, and others (see, generally, Sambrook et al., supra; see also Watson et al., (1992) Recombinant DNA, Chapter 12, 2d edition, Scientific American Books; incorporated herein by reference). Other methods used to transform mammalian cells include the use of polybrene-mediated transfer and protoplast fusion. Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In one embodiment of the present disclosure, the expression vector or construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (*Proc. Natl. Acad. Sci.* (USA) 81:7529–7533, 1984) successfully injected polyomavirus DNA in the form of $CaPO_4$ precipitates into liver and spleen of adult and newborn mice demonstrating active viral replication and acute infection. Benvenisty and Reshef (*Proc. Natl. Acad. Sci.* (USA) 83:9551–9555, 1986, incorporated herein by reference) also demonstrated that direct intraperitoneal injection of $CaPO_4$ precipitated plasmids results in expression of the transfected genes. It is envisioned that DNA encoding a gene of interest may also be transferred in a similar manner in vivo and express the gene product.

Another embodiment of the disclosure for transferring a naked DNA expression construct into cells may involve particle bombardment. This method depends on the ability to accelerate DNA coated microprojectiles to a high velocity allowing them to pierce cell membranes and enter cells without killing them (Klein et al., *Biotechnology* 10:286–291, 1992, incorporated herein by reference). Several devices for accelerating small particles have been developed. One such device relies on a high voltage discharge to generate an electrical current, which in turn provides the motive force. The microprojectiles used have consisted of biologically inert substances such as tungsten or gold beads. Selected organs including the liver, skin, and muscle tissue of rats and mice have been bombarded in vivo (Zelenin et al., *Genetika* 27:2182–2186, 1991, incorporated herein by reference). This may require surgical exposure of the tissue or cells, to eliminate any intervening tissue between the gun and the target organ, i.e., ex vivo treatment.

In a further embodiment of the disclosure, the expression construct maybe entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, *Targeted Diagn. Ther.* 4:87–103, 1991). Also contemplated are lipofectamine-DNA complexes. Liposome-mediated nucleic acid delivery and expression of foreign DNA in vitro has been very successful. Wong et al. (*Gene* 10:87–94, 1980, incorporated herein by reference) demonstrated the feasibility of liposome-mediated delivery and expression of foreign DNA in cultured chick embryo, HeLa, and hepatoma cells. Nicolau et al. (*Methods Enzymol.* 149:157–176, 1987, incorporated herein by reference) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., *J. Biol. Chem.* 264:12126–12129, 1989, incorporated herein by reference). In other embodiments, the liposome may be complexed or employed in conjunction with nuclear non-histone chromosomal proteins (HMG-1) (Kato et al., *J. Biol. Chem.* 266:3361–3364, 1991, incorporated herein by reference). In yet further embodiments, the liposome may be complexed or employed in conjunction with both HVJ and HMG-1. In that such expression constructs have been successfully employed in transfer and expression of nucleic acid in vitro and in vivo, then they are applicable for the present disclosure. Where a bacterial promoter is employed in the DNA construct, it also will be desirable to include within the liposome an appropriate bacterial polymerase.

Other expression constructs that can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific. Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, *J. Biol. Chem.* 262:4429–4432, 1987, incorporated herein by reference) and transferrin (Wagner et al., *Proc. Natl. Acad. Sci. (USA)* 87:3410–3414, 1990, incorporated herein by reference). A synthetic neoglycoprotein, which recognizes the same receptor as ASOR, has also been used as a gene delivery vehicle (Ferkol et al., *FASEB J.* 7:1081–1091, 1993; Perales et al., *Proc. Natl. Acad. Sci.* (USA) 91:4086–4090, 1994, incorporated herein by reference) and epidermal growth factor (EGF) has been used to deliver genes to squamous carcinoma cells (Myers, EPO 0273085).

In an embodiment of the present disclosure, β2GP1 may be administered in the form of a chimeric protein comprising the biologically active portion of β2GP1 and a ligand. The ligand may be a growth factor, chemokine, growth factor receptor, antibody and the like that targets β2GP1 to a specific site, protein, or cell type. Administration of the β2GP1 chimeric protein allows for efficient targeting of β2GP1 to a site. For example, the ligand comprising the chimeric protein may be a modified bFGF protein that binds to the FGF receptor but does not cause angiogenesis. In another example, the chimeric protein may include a ligand for the endothelial cell surface molecule CD31 or other endothelial cell ligands.

In other embodiments, the delivery vehicle may comprise a ligand and a liposome. For example, Nicolau et al. (*Methods Enzymol.* 149:157–176, 1987, incorporated herein by reference) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type such as endothelial or tumor cells, by any number of receptor-ligand systems with or without liposomes. For example, epidermal growth factor (EGF) may be used as the receptor for mediated delivery of a nucleic acid encoding a gene in many tumor cells that exhibit upregulation of EGF receptor. Also, antibodies to CD5 (CLL), CD22 (lymphoma), CD25 (T-cell leukemia), and MAA (melanoma) can similarly be used as targeting moieties.

Cells into which the β2GP1 gene has been transferred can be used in the present disclosure as transient transformants. Alternatively, where the cells are cells in vitro, they can be subjected to several rounds of clonal selection (if the vector also contains a gene encoding a selectable marker, such as a gene conferring resistance to a toxin) to select for stable transformants. Within the cells, the β2GP1 gene is expressed such that the cells express the β2GP1 polypeptide. Successful expression of the gene can be assessed via standard molecular biological techniques (e.g., Northern hybridization, Western blotting, immunoprecipitation, enzyme immunoassay, etc.).

D. In vivo Delivery and Treatment Protocols

The present disclosure also encompasses methods for the in vivo or ex vivo delivery of β2GP1, for example to treat a tumor or a patient using gene therapy. Many expression vectors known in the art are particularly well suited for in vivo delivery of nucleic acid sequences that are then expressed in cells, tissues, or organisms of interest, for example adenovirus, retrovirus, vaccinia virus, adeno-associated virus (AAV), herpes viruses, and hepatitis B virus. In certain embodiments, gene transfer may be more easily be performed under ex vivo conditions. Ex vivo gene therapy refers to the isolation of cells from an organism, the delivery of a nucleic acid into the cells, in vitro, and then the return of the modified cells back into the organism. This may involve the surgical removal of tissue/organs from an organism or the primary culture of cells and tissues. Anderson et al., U.S. Pat. No. 5,399,346, incorporated herein in its entirety, discloses ex vivo therapeutic methods.

(i) Adenovirus

One of the preferred methods for in vivo delivery involves the use of an adenovirus expression vector. As used herein, "adenovirus expression vector" refers to those constructs containing adenovirus sequences sufficient to (a) support packaging of the construct and (b) to express a polynucleotide that has been cloned therein. In this context, expression does not require that the gene product be synthesized, but in a preferred embodiment, the gene product is expressed.

The expression vector comprises a genetically engineered form of adenovirus. Knowledge of the genetic organization or adenovirus, a 36 kilobases (kB), linear, double-strained DNA virus, allows substitution of large pieces of adenoviral DNA with foreign sequences up to approximately 7 kB. In contrast to retrovirus, the infection of adenovira DNA in host cells does not result in chromosomal integration because adenoviral DNA can replicate in an episomal manner without potential genotoxicity. Also, adenoviruses are structurally stable, and no genome rearrangement has been detected after extensive amplification. So far, adenoviral infection appears to be linked only to mild disease such as acute respiratory disease in humans.

Adenovirus is particularly suitable for use as a gene transfer vector because of its midsized genome, ease of manipulation, high titer, wide target-cell range and high infectivity. In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure. Use of the YAC system is an alternative approach for the production of recombinant adenovirus.

Generation and propagation of the current adenovirus vectors, which are replication deficient, depend on a unique helper cell line, for example, the helper cell line designated 293 (Graham et al., *J. Gen. Virol.* 36:59–74, 1977, incorporated herein by reference). Helper cell lines may be derived from human cells such as human embryonic kidney cells, muscle cells, hematopoictic cells, or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Other than the requirement that the adenovirus vector be replication defective, or at least conditionally defective, the nature of the adenovirus vector is not believed to be crucial to the successful practice of the disclosure. The adenovirus may be one of any of the 42 different known serotypes or subgroups A-F. Adenovirus type 5 of subgroup C is the preferred starting material in order to obtain the conditional replication-defective adenovirus vector for use in the present disclosure. This is because Adenovirus type 5 is a human adenovirus about which a great deal of biochemical and genetic information is known, and it has historically been used for most constructions employing adenovirus as a vector. The typical vector according to the present disclosure is replication defective and does not have an adenovirus E1 region. Thus, it will be most convenient to introduce the polynucleotide encoding the gene of interest at the position where the El coding sequences have been removed. However, the position of insertion of the construct within the adenovirus sequences is not critical. The polynucleotide encoding the gene of interest may also be inserted in lieu of the deleted E3 region in E3 replacement vectors or in the E4 region where a helper cell line or helper virus complements the E4 defect.

Adenovirus is easy to grow and manipulate and exhibits a broad host range in vitro and in vivo. This group of viruses can be obtained in high titers, e.g., $10^9$–$10^{11}$ plaque-forming units per ml, and they are highly infective. The life cycle of adenovirus does not require integration in to the host cell genome. The foreign genes delivered by adenovirus vectors are episomal and, therefore, have low genotoxicity to host cells. No side effects have been reported in studies of vaccination with wild-type adenovirus, demonstrating their safety and therapeutic potential as in vivo gene transfer vectors.

Adendovirus have been used in eukaryotic gene expression and vaccine development. Recently, animal studies suggested that recombinant adenovirus could be used for gene therapy (Stratford-Perricaudet et al., *Bone Marrow Transplant* 9 Suppl. 1:151–152, 1992; Stratford-Perricaudet et al., *Hum. Gene Ther.* 1:241–256, 1990; Rich et al., *Hum. Gene Ther.* 4:461–476, 1993, incorporated herein by reference). Studies in administering recombinant adenovirus to different tissues include trachea instillation (Rosenfeld et al., *Science* 252:431–434, 1991; Voshimura et al., *Nucleic Acids Res.* 20:3233–3240, 1992, incorporated herein by reference), muscle injection (Ragot et al., *Nature* 361:647–650, 1993, incorporated herein by reference), peripheral intravenous injections (Herz and Gerard, *Proc. Natl. Acad. Sci.* (USA) 90:2812–2816, 1993, incorporated herein by reference) and stereotatic inoculation into the brain (Le Gal La Salle et al., *Science* 259:988–990, 1993, incorporated herein by reference).

(ii) Retroviruses

Retroviruses are a group of single-stranded RNA viruses characterized by an ability to convert their RNA to double-stranded DNA to infected cells by a process of reverse-transcription. The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. Methods for packaging a recombinant plasmid containing a nucleic acid sequence of interest, which are then secreted into the culture media, are well known in the art (see, e.g., Nicolas and Rubenstein, *Biotechnology* 10:493–513, 1988, incorporated herein by reference). The media containing the recombinant retroviruses is collected, optionally concentrated, and used for gene transfer. Retroviral vectors are able to infect a broad variety of cell types. However, integration and stable expression require the division of host cells (Paskind et al., *Virology* 67:242–248, 1975).

There are certain limitations to the use of retrovirus vectors in all aspects of the present disclosure. For example, retrovirus vectors usually integrate into random sites in the cell genome. This can lead to insertional mutagenesis through the interruption of host genes or through the insertion of viral regulatory sequences that can interfere with the function of flanking genes. Another concern with the use of defective retrovirus vectors is the potential appearance of wild-type replication-competent virus in the packaging cells. New packaging cell lines are now available, however, that should greatly decrease the likelihood of recombination (see, e.g., Markowitz et al., *Adv. Exp. Med. Biol.* 241:35–40, 1988, incorporated herein by reference).

(iii) Other Viral Vectors as Expression Constructs

Other viral vectors may be employed as expression constructs in the present disclosure. Vectors derived from viruses such as vaccinia virus (Coupar et al., *Gene* 68:1–10, 1988, incorporated herein by reference), adeno-associated virus (AAV) (Hermonat and Muzycska, *Proc. Natl. Acad. Sci.* (USA) 81:6466–6470, 1984, incorporated herein by reference), herpes viruses, and defective hepatitis B virus (Chang et al., *J. Virol.* 68:646–653, 1991, incorporated herein by reference) may be employed. These viral vectors offer several attractive features for various mammalian cells.

E. Pharmaceutical Compositions and Administration

Where clinical applications are contemplated, it will be necessary to prepare pharmaceutical compositions in a form appropriate for the intended application. Pharmaceutical compositions disclosed herein can be administered to a subject using a variety of routes of administration and dosage forms well known to those of skill in the art. As used herein, "pharmaceutical compositions of β2GP1" include compositions of β2GP1 polypeptides produced from natural, recombinant, or synthetic sources; expression vectors or constructs encoding β2GP1, including viral and non-viral gene delivery vectors or construct; and engineered cells expressing recombinant β2GP1. Generally, this will entail preparing compositions that are essentially free of pyrogens, as well as other impurities that could be harmful to cells, humans, or animals.

Pharmaceutical compositions of β2GP1 also include proteinaceous composition, which encompasses β2GP1 proteins, polypeptides, and peptides. In certain embodiments, the present disclosure concerns proteinaceous compositions comprising at least one proteinaceous molecule. As used herein, a "proteinaceous molecule" or "proteinaceous composition" generally refers, but is not limited to, a protein of greater than about 200 amino acids or the full length endogenous sequence translated from a gene, for example, a β2GP1 gene; a polypeptide of greater than about 100 amino acids; and/or a peptide of from about 3 to about 100 amino acids. "Proteinaceous" terms described above may be used interchangably herein.

In certain embodiments the size of the at least one proteinaceous molecule may comprise, but is not limited to, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or greater amino molecule residues, and any range derivable therein.

As used herein, an "amino molecule" refers to any amino acid, amino acid derivative, or amino acid mimic as would be known to one of ordinary skill in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties. Accordingly, a proteinaceous composition encompasses amino molecule sequences comprising at least one of the 20 common amino acids in naturally synthesized proteins, or at least one modified or unusual amino acid, known to those of skill in the art.

In certain embodiments, the proteinaceous composition comprises at least one protein, polypeptide, or peptide. In further embodiments, the proteinaceous composition comprises a biocompatible protein, polypeptide, or peptide. As used herein, the term "biocompatible" refers to a substance which produces no significant untoward effects when applied to, or administered to, a given organism according to the methods and amounts described herein. Such untoward or undesirable effects are those such as significant toxicity or adverse immunological reactions. In preferred embodiments, biocompatible protein, polypeptide or peptide containing compositions will generally be mammalian proteins or peptides or synthetic proteins or peptides each essentially free from toxins, pathogens, and harmful immunogens.

Proteinaceous compositions may be made by any technique known to those of skill in the art, including the expression of proteins, polypeptides, or peptides through standard molecular biological techniques, the isolation of proteinaceous compounds from natural sources, or the chemical synthesis of proteinaceous materials. The nucleotide and protein, polypeptide, and peptide sequences for various β2GP1 genes have been previously disclosed, and may be found at computerized databases known to those of ordinary skill in the art. One such database is the National Center for Biotechnology Information's Genbank and GenPept databases (http://www.ncbi.nlm.nih.gov/). The coding regions for these known genes may be amplified and/or expressed using the techniques disclosed herein or as would be know to those of ordinary skill in the art. Alternatively, various commercial preparations of proteins, polypeptides, and peptides are known to those of skill in the art.

In certain embodiments a proteinaceous compound may be purified. Generally, "purified" will refer to a protein, polypeptide, or peptide composition that has been subjected to fractionation to remove various other proteins, polypeptides, or peptides, and which composition substantially retains its activity, as may be assessed, for example, by protein assays, as would be known to one of ordinary skill in the art for the specific or desired protein, polypeptide, or peptide.

In certain embodiments, the proteinaceous composition may comprise at least one antibody. It is contemplated that antibodies to specific tissues may bind the tissue(s) and foster tighter adhesion to the tissue(s). As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting. The term "antibody" is used to refer to any antibody-like molecule that has an antigen binding region, and includes antibody fragments such as Fab', Fab, F(ab')2, single domain antibodies (DABs), Fv, scFv (single chain Fv), and the like. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

It is contemplated that virtually any protein, polypeptide, or peptide containing component may be used in the compositions and methods disclosed herein. In preferred embodiments, however, the proteinaceous material is biocompatible. In certain embodiments, it is envisioned that the formation of a more viscous composition will be advantageous in that will allow the composition to be more precisely or easily applied to the tissue and to be maintained in contact with the tissue throughout the procedure. In such cases, the use of a peptide composition, or more preferably, a polypeptide or protein composition, is contemplated. Ranges of viscosity include, but are not limited to, about 40 to about 100 poise. In certain aspects, a viscosity of about 80 to about 100 poise is preferred.

Polypeptides, proteins, and peptides suitable for use in the present disclosure may be autologous proteins or peptides, although the disclosure is clearly not limited to the use of such autologous proteins. As used herein, the term "autologous protein, polypeptide, or peptide" refers to a protein, polypeptide or peptide which is derived or obtained from an organism. Organisms that may be used include, but are not limited to, a primate, a canine, a feline, a bovine, an equine, an ovine, a murine, a caprine, a porcine species, and the like, with a selected animal or human subject being preferred. The "autologous protein, polypeptide, or peptide" may then be used as a component of a composition intended for application to the selected animal or human subject.

To select other proteins, polypeptides, peptides and the like for use in the methods and compositions of the present disclosure, one would preferably select a proteinaceous material that possesses one or more of the following characteristics: it forms a solution with a high percentage of proteinaceous material solubilized; it possesses a high viscosity (i.e. about 40 to about 100 poise); it has the correct amino-acids present to form covalent cross-links; and/or it is biocompatible (i.e. from mammalian origin for mammals, preferably from human origin for humans, from canine origin for canines, etc.; it is autologous; it is non-allergenic, and/or it is nonimmunogenic).

Pharmaceutical compositions of β2GP1 may be administered through a number of different routes, including oral, peroral, enteral, pulmonary, rectal, nasal, vaginal, lingual, direct injection, intravenous, intraarterial, intracardial, intradermal, intramuscular, intraperitoneal, intracutaneous, intraocular, intranasal, intrapleural, intrathecal, intratumor, intrauterine, orthotopic, and subcutaneous administration. β2GP1 may also be suitable for systemic administration to the subject, including parenteral, topical, buccal, sublingual, transdermal, gavage, and oral administration. β2GP1 may also be administered parenterally, i.e. subcutaneously, intramuscularly, or intravenously. Agents can also be delivered to a tissue or organism in a variety of different compositions, including tablets, pills, capsules, powders, aerosols, suppositories, skin patches, parenterals, and oral liquids, including oil-aqueous suspensions, solutions, and emulsions. Also contemplated is the administration of β2GP1 in single or multiple dosage regimens, as well as by using compositions that involve sustained release (long acting) formulations and devices.

In addition to other routes of administration, β2GP1 can be presented to the tissue of interest by direct infusion or by using expression vectors or constructs, including but not limited to genetically modified cells or tissues, viral vectors, or infusion of genetic material, which can then be incorporated by cells or in the tissue of a host organism. Thus, for example, a composition containing a source of β2GP1 (i.e., a β2GP1 polypeptide or a β2GP1 expression vector or construct, as described herein) can be introduced into the systemic circulation, which will distribute the source of β2GP1 to the tissue of interest. Alternatively, a composition containing a source of β2GP1 can be applied topically or injected directly into a tissue of interest (e.g., injected as a bolus within a tumor or intercutaneous or subcutaneous site, applied to all or a portion of the surface of the skin, dropped onto the surface of the eye, etc.). Additionally, β2GP1 may be incorporated into biodegradable polymers that allow for the sustained release of the compound. The polymers can be implanted in the vicinity of where drug delivery is desired, for example, at the site of a tumor, or implanted so that the β2GP1 is slowly released systemically. The biodegradable polymers and their use are described, for example, in Brem et al., *J. Neurosurg.* 74:441–446, 1991, which is incorporated herein by reference.

In general, appropriate salts and buffers will be employed to render delivery vectors stable and allow for uptake by target cells. Buffers also will be employed when recombinant cells are introduced into a cell, tissue, or organism. Aqueous compositions of the present disclosure contain an effective amount of the expression vector or cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an organism, animal, or human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present disclosure, its use in therapeutic compositions is contemplated. Supplementary active ingredients also can be incorporated into the compositions.

β2GP1 can be administered as a free base, as well as any acid addition salt thereof. Pharmacologically acceptable salts of β2GP1 include those derived from organic and inorganic acids such as, without limitation, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embonic acid, enanthic acid, and the like. Solutions of the active ingredients as free base or pharmacologically acceptable salts can be prepared in water suitably mixed with surfactant, such as hydroxypropylcellulose. Dispersions also can be prepared in glycerol, liquid polyethylene glycols, mixtures thereof, and in oils. Under ordinary conditions of storage and use, these preparations contain a preservative to prevent growth of microorganisms.

The expression vectors, constructs, and delivery vehicles of the present disclosure may include classic pharmaceutical preparations. Administration of these compositions according to the present disclosure will be via any common route so long as the target tissue is available via that route. Such compositions would normally be administered as pharmaceutically acceptable compositions, described supra.

The polypeptides, vectors, or cells of the present disclosure are advantageously administered in the form of injectable compositions either as liquid solutions or suspensions;

solid forms or lyophilized forms suitable for solution in, or suspension in, liquid prior to injection also may be prepared. These preparations also may be emulsified. A typical compositions for such purposes comprises a 50 mg or up to about 100 mg of human serum albumin per milliliter of phosphate buffered saline. Other pharmaceutically acceptable carriers include aqueous solutions, non-toxic excipients, including salts, preservatives, buffers and the like. Examples of non-aqueous solvents are propylene glycol, polyethylene glycol, vegetable oil, and injectable organic esters, such as theyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components in the pharmaceutical compositions are adjusted according to well known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations, nasal sprays, suppositories, tonics, or powders. When the route is topical, the form may be a cream, ointment, salve, gel, or spray.

An effective amount of the therapeutic agent is determined based on the intended goal. For example, an effective amount of β2GP1 as used herein is an amount of β2GP1 that is effective for inhibiting, treating, or preventing unwanted endothelial cell proliferation, cord formation, cell migration, angiogenesis, and/or angioectasia, especially as related to neoplasm or tumor growth. The term "unit dose" refers to a physically discrete unit suitable for use in an organism, each unit containing a predetermined quantity of the therapeutic composition calculated to produce the desired response in association with its administration, i.e., the appropriate route and treatment regimen. The quantity to be administered, both according to number of treatments and unit dose, depends on the organism to be treated, the state of the organism, and the protection desired. Precise amounts of the therapeutic composition also depend on the judgment of the practitioner and may be peculiar to each individual organism. The optimal daily dose of β2GP1 useful for the purposes of the present disclosure is determined by methods known in the art, e.g., based on the severity of the angiogenic disease or condition and the symptoms being treated, the condition of the organism to whom treatment is being given, the desired degree of therapeutic response, and the concomitant therapies being administered to the organism or human. The total daily dosage administered to an organism, typically a human patient, should be at least the amount required to inhibit, treat, or prevent unwanted endothelial cell proliferation and/or angiogenesis.

The optimal dosage of administered β2GP1 will be determined by methods known in the art and will vary depending on such factors as the organism's age, weight, height, sex, general medical/clinical condition, previous medical history, disease progression, tumor burden, route of administration, formulation, concomitant therapies being administered, observed response of the organism, and the like. The dosage can be administered in a single or multiple dosage regimen, or delivered in an essentially continuous manner, e.g., via a transdermal patch. Depending on the formulation of a composition comprising β2GP1, it is supplied over a time course sufficient to inhibit, treat, prevent, attenuate, or retard unwanted endothelial cell proliferation and/or angiogenesis within the desired tissue or organism. In some protocols (e.g., where the β2GP1 is supplied to the surface of skin), repeated application may enhance the antiangiogenic effect. Where the source of β2GP1 is a β2GP1 expression vector or construct, cells expressing the vector or construct may produce an effective amount of the protein (i.e., sufficient to inhibit angiogenesis in the tissue).

In general, it is desirable to provide the organism with a dosage of β2GP1 of at least about 0.01 mg/kg, 0.02 mg/kg or 0.05 mg/kg to about 0.10 mg/kg, or about 0.15 mg/kg to about 0.175 mg/kg, or about 0.20 mg/kg to about 0.30 mg/kg, or about 0.5 mg/kg and may extend to about 1.0 mg/kg or even 1.5, 2.0, 3.0, 5.0 or 10.0 mg/kg of the organism's body weight depending on the route of administration. In other preferred embodiments, a range of from about 1 mg/kg to about 25 mg/kg, preferably at least about 50 mg/kg, more preferably about 100 mg/kg is contemplated, although a lower or higher dose may be administered. In other preferred embodiments, the daily dose will be in the range of about 0.01 mg to about 1000 mg per day. Preferred doses will be about 0.05, 0.1, 0.2, 0.3, 0.4, 0.5, 1.0, 2.0, 3.0, 4.0, 5.0, 10, 20, 30, 40, 50, 60, 70, 80, 90, 100, 150, 200, 300, 400, 500, 600, 700, 800, 900, or 1000 mg per day.

The present disclosure also contemplates providing to a subject a pharmacological composition with a source of β2GP1 and a suitable diluent, such as saline, phosphate-buffered saline, or other physiologically tolerable diluents. In addition to the source of P32GP1, the composition includes a diluent, which includes one or more pharmacologically-acceptable carriers. Pharmaceutical compositions for use in accordance with the present disclosure can be formulated in a conventional manner using one or more pharmacologically or physiologically acceptable carriers comprising excipients, as well as optional auxiliaries which facilitate processing of the active compounds into preparations which can be used pharmaceutically. Proper formulation is dependent upon the route of administration chosen. Thus, for systemic injection, the source of β2GP1 can be formulated in aqueous solutions, preferably in physiologically compatible buffers. For transmucosal administration, penetrants appropriate to the barrier to be permeated are used in the formulation. Such penetrants are generally known in the art. For oral administration, the source of β2GP1 can be combined with carriers suitable for inclusion into tablets, pills, dragees, capsules, liquids, gels, syrups, slurries, diposomes, suspensions and the like. For administration by inhalation, the source of β2GP1 is conveniently delivered in the form of an aerosol spray presentation from pressurized packs or a nebuliser, with the use of a suitable propellant. The source of β2GP1 can be formulated for parenteral administration by injection, e.g., by bolus injection or continuous infusion. Such compositions can take such forms as suspensions, solutions, or emulsions in oily or aqueous vehicles, and can contain formulatory agents such as suspending, stabilizing, and/or dispersing agents. For application to the skin, the source of β2GP1 can be formulated into a suitable gel, magma, creme, ointment, or other carrier. For application to the eyes, the source of β2GP1 can be formulated in aqueous solutions, preferably in physiologically compatible buffers. The source of β2GP1 can also be formulated into other pharmaceutical compositions such as those known in the art.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Quantitative Neovascularization Assays

β2GP1 is able to abrogate neovascularization into subcutaneous gel foam implants using a novel technique for quantifying vascular volume. This technique uses a reproducible and readily quantifiable assay to study angiogenesis in vivo, and in particular assesses the propensity of different compounds to inhibit angiogenesis. This assay uses absorbent surgical gel foam (Nabai et al., *Dermatology* 191: 240–241, 1995, incorporated herein by reference). Briefly, sterile gel foam absorbable sponges (Pharmacia & Upjohn, NJ) were cut into approximately 5×5 mm pieces and hydrated overnight at 4° C. in sterile phosphate-buffered saline (PBS). Excess PBS was removed by blotting. Sterile 0.4% agarose (100 μl) containing human serum albumin, intact β2GP1, or N-β2GP1 was aliquoted to each sponge cube at 45° C. The gel foam sponges were allowed to harden for 1 hour at room temperature before implantation. After the mice were anesthetized, a ~5 mm midline incision was made through the skin and subcutaneous pockets were formed on both sides with forceps. One gel foam sponge was inserted into each pocket and the wound was closed with two surgical metal clips. Fourteen days later, the mice were sacrificed and the gel foam sponges were recovered.

The extent of angiogenesis into the gel foam plugs can be determined by assessing microvessel density (MVD) by immunofluorescence of antigen-specific endothelial cell markers and by directly estimating vascular volume (QVV). To quantify the degree of neovascularization/vascular volume in the gel foam implants recovered from the mice, vascular volume was estimated by assessing blood volume in the gel foam plugs. Mice were first injected intravenously with 0.1 mL of 40% packed syngeneic red blood cells (RBC) labeled with $^{51}$Cr (1.0 mCi/mL packed red cells). The mice were bled from the tail vein approximately 10 minutes later and an aliquot (10 μL) of blood was collected to determine cpm/μL blood. The mice were then sacrificed and the vascular volume of the excised gel foam implants was quantified by scintillation counting. Vascular volume was determined by comparing counts from tail vein samples to counts obtained in the plugs (used to calculate the vascular volume/gram). This same method can also be used to assess vascular volume and the extent of angiogenesis in tumors.

After vascular volume has been quantified, MVD can be assessed by immunofluorescence of antigen-specific endothelial cell markers, for example CD31 and PECAM-1. To do this, frozen gel foam specimens are sectioned (10–12 μm), mounted on positively charged slides, air-dried for 30 minutes, fixed in cold acetone for 5 minutes, followed by acetone:chloroform (1:1) for 5 minutes, and acetone alone for an additional 5 minutes. After rehydrating the sections with PBS they are incubated for 20 minutes at room temperature with a protein-blocking solution containing 5% normal horse serum and 1% normal goat serum in PBS, and then incubated at 4° C. with a 1:400 dilution of rat monoclonal anti-mouse CD31 antibody (Pharmingen, San Diego, Calif.). The slides are then washed and stained with 1:200 dilution of secondary goat anti-rat antibody conjugated to Texas Red (Jackson Research Laboratories, West Grove, Calif.). The samples are mounted in Vectashield mounting medium for fluorescence with DAPI (Vector Laboratories, Burlingame, Calif.). Fluorescence microscopy can be done with a Zeiss Axioplan2 microscope (Carl Zeiss, New York, N.Y.) equipped with a 100-W HBO mercury bulb and filter sets to individually capture red, green, and blue fluorescent images. Images can be captured using a C5810 Hamamatsu color chilled 3CCD camera (Hamamatsu, Japan) and digitized using Optimas imaging software (Silver Springs, Md.). Endothelial cells are identified by red fluorescence. For quantification of MVD, ten 0.159-mm$^2$ fields at 100× magnification are digitized and stored for analysis.

Figure 2:
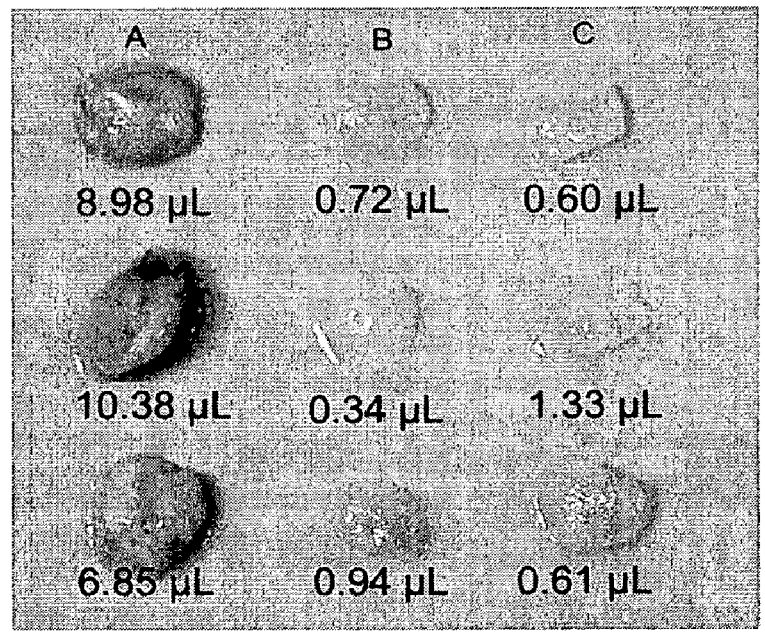
FIG. 2. Quantitative vascular volume of gel foam implants as described in FIG. 1: Calculated vascular volumes appear under each set of individual plugs. Estimated μL vascular volume in the plugs was calculated by comparing the counts of 10 μL of tail vein blood from mice injected with $^{51}$Cr-labeled syngeneic red blood cells (cpm/μL) with cpm associated with the gel foam implants. Plugs A, B, and C contained human serum albumin, intact β2GP1, and N-β2GP1, respectively. Again, the vascular volume in B and C plugs was dramatically less than in A plugs, demonstrating the ability of β2GP1 to inhibit or prevent neovascularization.

FIG. 1 shows dramatic neovascularization into control implants (gel foam plug A). Plugs containing intact β2GP1 or N-β2GP1, on the other hand, appear to completely block the growth of new blood vessels into the implants. Moreover, control plugs (containing either buffer alone or human serum albumin) were strongly attached to the fascia whereas most of the β2GP1-containing plugs remained very loosely attached or not attached at all (FIG. 1). The extent of vascularization into the implants quantified by scintillation counting indicated that neo vascularization was inhibited >10-fold in plugs containing β2GP1 (FIG. 2). Note that both intact β2GP1 and N-β2GP1 inhibited neovascularization into the plugs. It is possible that since implantation of the gel foam creates a wound, intact β2GP1 may be cleaved to the nicked form by endogenous proteases in situ. Similarly, wounding caused by subcutaneous injection could also result in activation of endogenous plasmin and cleavage of the injected β2GP1 to N-β2GP1.

EXAMPLE 2

β2GP1 Kills and Inhibits the Growth of In vitro Cultivated Pulmonary Microvascular Endothelial Cells The inhibitory effect of β2GP1 on neovascularization shown in Example 1 could be due to a variety of effects on endothelial cells, including but not limited to β2GP1-induced apoptosis, inhibition of cell growth, cell migration, and/or cord assembly. To determine whether intact β2GP1 and/or N-β2GP1 inhibit cell growth or induce apoptosis, murine pulmonary microvascular endothelial cells were grown for 4 days in the presence of β2GP1, N-β2GP1 and, as a control, human serum albumin ($Log_2$ dilution from 100 μg/ml). An MTT assay (3-(4,5-dimethylthiazol-2-yl)-2,5-diphenyl tetrazolium bromide) was used to measure the cell growth of each set of treated pulmonary microvascular cells.

Figure 3:
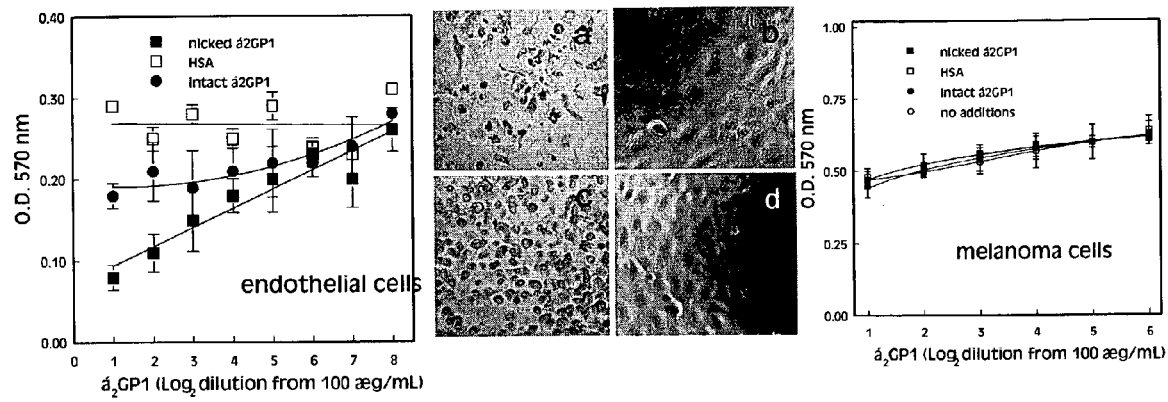
FIG. 3. Left Panel. MTT assay (3-(4,5-dimethylthiazol-2-yl)-2,5-diphenyl tetrazolium bromide) of pulmonary microvascular cells grown for 4 days in the presence of the indicated proteins. Double dilutions from 100 μg/mL. Middle Panel. Photomicrographs of typical cultures (same plate as the MTT assay data); a: N-β2GP1; b: human serum albumin; c: intact β2GP1; and d: control cells without any treatment. As shown, there is a substantial reduction in the number of viable endothelial cells after incubation with intact β2GP1 and N-β2GP1 compared to the controls. Right Panel. MTT assay of B16 melanoma cells ($20 \times 10^3$) grown for 5 days in the presence of the indicated compounds. Double dilutions from 100 μg/mL. As shown, neither N-β2GP1 or intact β2GP1 inhibited proliferation of this tumor cell line.

The data in the left panel of FIG. 3 shows a substantial reduction in the number of viable endothelial cells after 4 days of incubation with intact β2GP1 and N-β2GP1. Importantly, N-β2GP1 was 20 times more effective in inhibiting endothelial cell growth than β2GP1 (5 μg/mL of N-β2GP1 resulted in the same degree of inhibition as 100 μg/mL of β2GP1). In the middle panel of FIG. 3, microscopic analysis of the cultures revealed a significant reduction in the number of cells/field in the N-β2GP1 containing cultures (FIG. 3 middle panel a). The intact β2GP1 treated cultures contained a relatively large number of round pyknotic cells (FIG. 3 middle panel b), and although they were not as sparse as the N-β2GP1 cultures, they were much more sparse than the controls. Interestingly, other experiments have shown that the effect of N-β2GP1 on endothelial cells is not species specific. For example, the addition of N-β2GP1 to subconfluent bovine aorta endothelial cells resulted in >50% cell death within three days. Intact β2GP1 did not have an effect on these cells. The lack of (species) specificity is not surprising given the very high homology of β2GP1 between species.

The same experiment outlined for the murine pulmonary microvascular endothelial cells was repeated on B16 melanoma cells to determine whether the β2GP1-dependent decrease in viable cell number was specific to endothelial cells. As shown in the right panel of FIG. 3, neither intact β2GP1 nor N-β2GP1 had any effect on the proliferation of tumor cells.

EXAMPLE 3

β2GP1 Inhibits the Growth of Syngeneic Mouse Tumors

Figure 4:
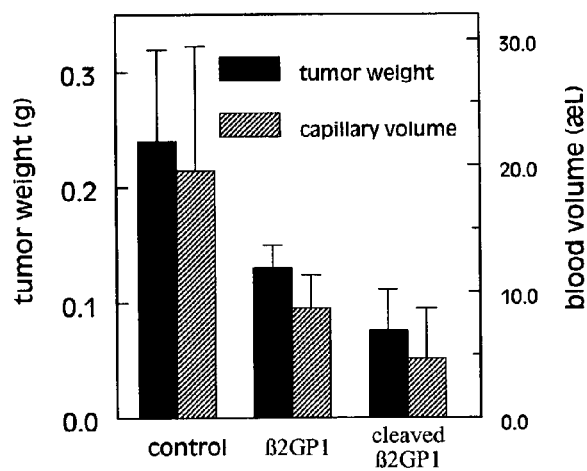
FIG. 4. C3H mice were injected with $10^6$ UV 2237 cells. Daily subcutaneous injections with buffer alone, intact β2GP1, and N-β2GP1 were started five days later for 14 days. After injecting the mice with $^{51}$Cr-labeled red blood cells, the mice were sacrificed, tumors weighed, and tumor blood vessel volume was calculated. As shown, mice treated with intact β2GP1 and N-β2GP1 had a significant reduction in both tumor weight and blood capillary volume of the tumors.

As shown in Example 1, β2GP1 and N-β2GP1 were able to abrogate the growth of new vasculature into gel foam implants. Next, experiments were preformed to determine whether repeated administration of β2GP1 could also inhibit vascularization into proliferating syngeneic tumors. Three independent mouse models were used to test whether treatment of mice with intact β2GP1 or N-β2GP1 inhibits tumor growth. The first model of fibrosarcoma was generated by subcutaneously injecting C3H mice with $0.5 \times 10^6$ UV2237 fibrosarcoma cells. When the tumors were palpable (after 5 days), buffer, intact β2GP1, or N-β2GP1 was injected subcutaneously every day for two weeks. The dosage of intact β2GP1 or N-β2GP1 for different experiments ranged from 0.1 to 0.5 mg/mouse/day. Thus, the dosage was approximately 5 mg/kg to 25 mg/kg per day. The mice were then injected intravenously with $^{51}Cr$ labeled syngeneic red blood cells to determine vascular volume (as described in Example 1). The tumors were excised, weighed, and assessed for vascularity by determining the amount of labeled red cells present in the tumor tissue ($^{51}Cr$) as compared to an aliquot of tail blood. The results presented in FIG. 4 show a significant reduction in both tumor weight and blood capillary volume in animals treated with both intact β2GP1 and N-β2GP1.

Figure 5:
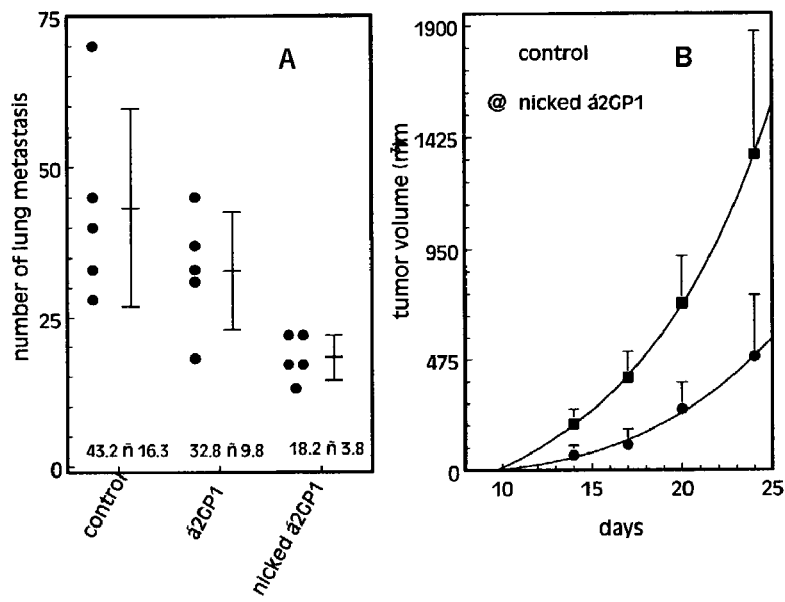
FIG. 5. C57BL/6 mice were injected with B16F10 melanoma cells intravenously (A) or subcutaneously (B). Daily intraperitoneal injections with buffer alone, intact β2GP1, or N-β2GP1 started 1 day later and lasted for 3 weeks. (A) Mice were sacrificed, lungs removed and fixed; tumors were then enumerated. (B) Tumor size was measured at the indicated time points. Mice treated with N-β2GP1 had a significant reduction in both the size of the subcutaneous growing tumors and the number of lung metastasis.

The second model of B16 melanoma was generated by intravenously and subcutaneously injecting C57BL/6 mice with $4 \times 10^5$ B16F10 syngeneic melanoma cells; these injections were designed to model experimental lung metastasis and local tumor growth, respectively. The mice were injected intraperitoneally at 24 hour intervals for the entire duration of the experiment (3 weeks) with intact β2GP1 and N-β2GP1 beginning one day after the tumor cells were injected. Again, the dosage of intact β2GP1 or N-β2GP1 for different experiments ranged from 0.1 to 0.5 mg/mouse/day. The rate of subcutaneous tumor growth was monitored by assessing tumor volume. Lung metastases were counted on day 24. FIG. 5 shows a significant reduction in both the size of the subcutaneous growing tumors and the number of lung metastasis in animals treated with N-β2GP1.

The third model of Tramp C2RE3 parental orthotopic prostate mode was generated by injecting C57BL/6 mice in the prostate with $0.4 \times 10^6$ TRAMP cells in 40 ill under magnification. On day 3 after the injection, buffer, intact β2GP1 (100 µg/day), or N-β2GP1 (100 µg/day) was injected intraperitoneally every day. On day 33, the tumors were harvested and weighed. The results of this experiment are shown below in Table 1 (data shown is based on the results of 6 animals/group):

TABLE 1

Effect of β2GP1 on the growth of orthotopically implanted TRAMP cells.

| Treatment | Mean tumor weight (g) SD |
|---|---|
| control | 0.388 ± 0.02 |
| intact β2GP1 | 0.466 ± 0.11 |
| N-β2GP1 | 0.147 ± 0.12* |

*The difference in tumor size between the group treated N-β2GP1 was significantly different from the other two groups ($P < 0.05$ Student's t-test).

As shown in Table 1, repeated administration of N-β2GP1 resulted in a significant decrease in tumor size. Taken together, the results of these experiments suggest that proteolytically nicked β2GP1 plays an important regulatory function in angiogenesis by preventing neovascularization into syngeneic tumors, as well as into model gel foam assay systems (see Example 1). Although as shown in FIG. 4, intact β2GP1 was effective in inhibiting the growth of UV2237, it is possible that the subcutaneously injected intact β2GP1 protein undergoes proteolytic cleavage in situ thereby generating the active nicked form, which is then able to prevent neovascularization into syngeneic tumors. Nevertheless, although N-β2GP1 may be the active anti-angiogenic form of the protein, these studies do not rule out the possibility that intact β2GP1 is also active as an anti-angiogenic protein.

EXAMPLE 4

N-β2GP1 Inhibits Cord Formation, Migration, and Invasion

Figure 6:
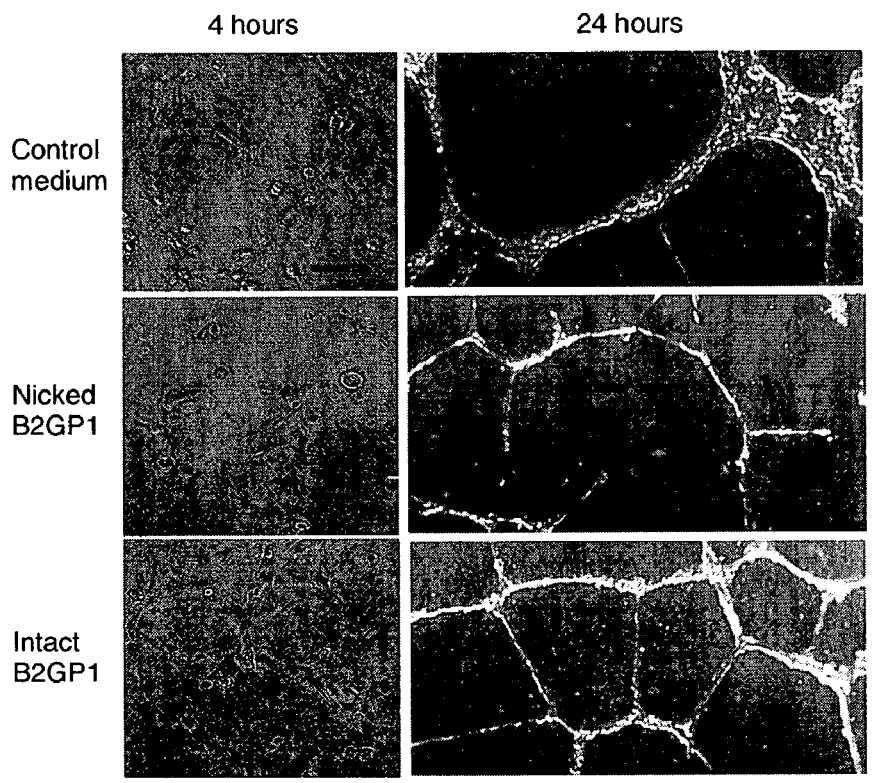
FIG. 6. Ability of β2GP1 to inhibit the formation of capillary-like tubes in in vitro Matrigel assays. Human umbilical cord vascular endothelial cells (HUVEC) ($10^5$/mL) resuspended in medium M-200 containing intact β2GP1 or N-β2GP1 (0.1 mg/mL) was added to 96 well plates coated with Matrigel. Images were recorded after 4 and 24 hours incubation at 37° C. N-β2GP1 caused cells to wander without direction on the plate, while control cultures incubated in medium alone or in media supplemented with intact β2GP1 began to assemble into capillary like structures within ~4 hours. Differences in the architecture of the fully formed tubes were also evident after 24 hours.

Since migration and invasion are processes required for the formation of new capillaries, β2GP1 was tested in in vitro Matrigel assays for the formation of capillary-like tubes. 96 well plates were first coated with Matrigel (50 µL at 10 mg/mL) according to the manufacturer's protocol. HUVEC ($10^5$/mL) were resuspended in medium M-200 containing intact β2GP1 or N-β2GP1 (0.1 mg/mL). 200 µl of the cell suspension was then added to the Matrigel-coated wells. Images were recorded after 4 and 24 hours incubation at 37° C., as shown in FIG. 6. As shown in the middle panel of FIG. 6, cells plated in the presence of N-β2GP1 seemed to wander without direction on the plate, while control cultures incubated in medium alone or media supplemented with intact β2GP1 were clearly beginning to assemble into capillary like structures within ~4 hours (FIG. 6, top and bottom panels). Differences in the architecture of the fully formed tubes were also evident after 24 hours, although the differences were somewhat less striking. Tubes in the N-β2GP1-containing cultures were composed of significantly fewer cells than the control cultures and gave rise to what appeared to be very thin and fractured tubes compared to thicker and more robust structures in the controls.

Figure 7:
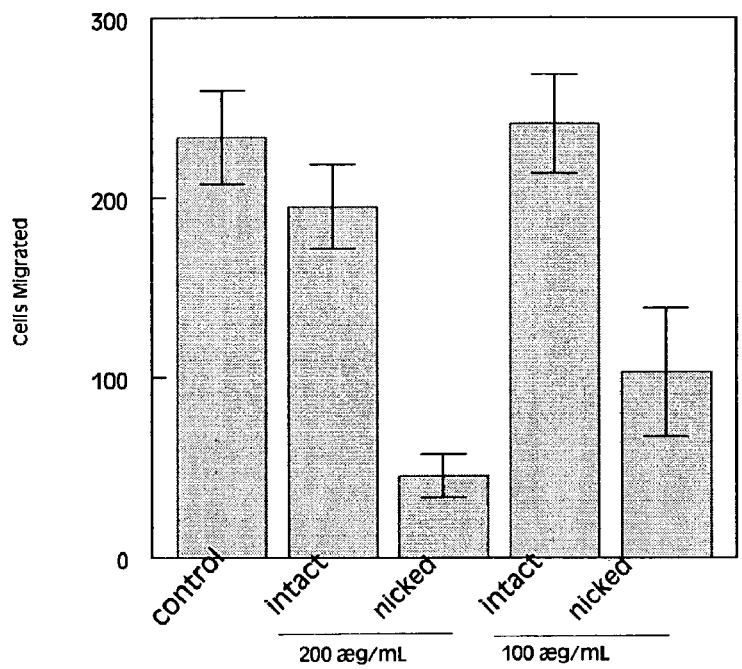
FIG. 7. Ability of β2GP1 to inhibit endothelial cell migration. To examine migration, BFGF chemo-attractant was added to the lower chambers of the transwells of a 24-well polycarbonate Boyden chamber. Next, HUVEC were resuspended with or without β2GP1 or N-β2GP1 (100 μg/mL or 200 μg/mL), and added to upper chamber. After a 5 hour incubation at 37° C., the transwells were fixed and stained and the number of cells that migrated was counted. N-β2GP1 at both concentrations was able to inhibit migration of endothelial cells in the Boyden chamber invasion assay, while intact β2GP1 was without effect.

Next, the effect of β2GP1 on endothelial cell migration was examined using the 24-well polycarbonate Boyden chambers (8.0 µM pore size, Becton Dickinson). For the migration assay, 750 µL of M-200 medium containing BFGF chemo-attractant was added to the lower chambers of the transwells. HUVEC ($10^5$ cells) were resuspended in 500 µL of M-200 medium with or without intact β2GP1 or N-β2GP1, and were added to upper chamber. After incubation at 37° C. for 5 hours, the transwells were fixed and stained, and the number of cells that migrated was counted (10 fields/chamber) by two blinded observers. Consistent with the above results for the formation of capillary-like tubes, N-β2GP1 inhibited the migration of endothelial cells in the Boyden chamber invasion assay, while intact β2GP1 had no effect on endothelial cell migration (FIG. 7). Taken together, these data suggest that N-β2GP1 can modulate endothelial cell migration, invasion, and formation of capillary tubes during an angiogenic response.

EXAMPLE 5

The Effect of β2GP1 on Endothelial Cells In vivo

In order for a tumor to grow, it must be able to manipulate the host vasculature to provide an adequate blood supply for its growth. Over the past decade, many studies have shown that the development of a tumor-directed blood supply occurs by several mechanisms that are not necessarily mutually exclusive. These mechanisms include sprouting angiogenesis, in which host vessels expand into the growing tumor by sprouting from pre-existing vessels (Carmeliet and Jain, *Nature* 407:249–57, 2000), and intussusceptive angiogenesis, which involves the repeated addition of transcapillary pillars in existing tumor vessels, thus allowing the vessels to grow from within themselves (Patan et al., *Microvascular Research* 51:260–72, 1996; Burri and Djonov, *Mol. Aspects Med.* 23: S1–S27, 2002). New vessels can also be formed by vasculogenesis, in which bone marrow precursors home directly to tumors and generate new vessels in situ (Rafii, *J. Clin. Invest.* 105:17–9, 2000). In some cases, a tumor can fulfill its needs by co-opting pre-existing vasculature without angiogenesis (Thompson et al., *Journal of Pathology* 151:323–32, 1987; Holash et al., *Science* 284:1994–8, 1999; Dome et al., *Journal of Pathology* 197:355–62, 2002). Tumors can also form mosaic vessels where tumor cells form part of the capillary wall (Chang et al., *Proc. Natl. Acad. Sci. (USA)* 97:14608–13, 2000). Because of the potential contribution of multiple angiogenic mechanisms to tumor growth, growth inhibition by β2GP1 could be due to the inability of a tumor exposed to β2GP1 to develop an effective blood supply by any one or more of these mechanisms.

Figure 8:
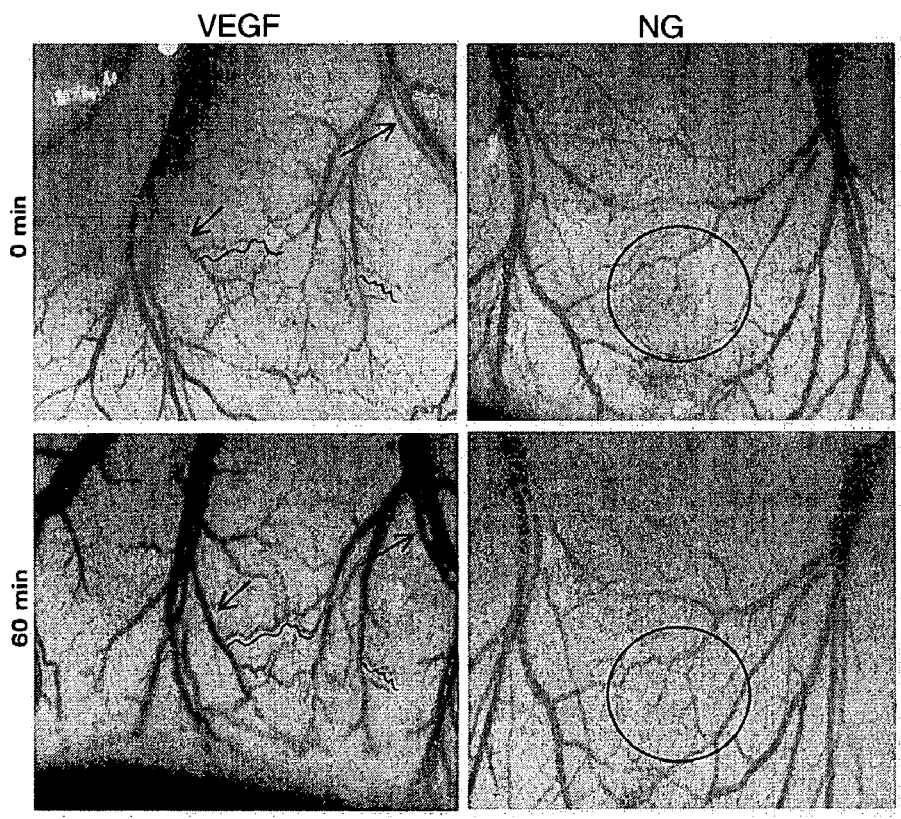
FIG. 8. Growth factor and chemically-induced blood vessel dilation (angioectasia). Normal mice were anesthetized and the mesentery was draped on the specimen stage of a dissecting microscope. After wetting the area of interest with vascular endothelial cell growth factor (VEGF) or nitroglycerin (NG), images were collected in real-time for 1 hour. VEGF: Areas of obvious dilation are marked with arrows. Note the increased tortuousness of vessels after the addition of VEGF, marked by the squiggly trace following some vessels in the VEGF frame (lower left), which was copied and superimposed on the same vessel in the zero time image (upper left). NG: Obvious areas of dilated vessels are also marked, although the magnitude of change is not as great as that obtained with VEGF. The circled area marks an area were small vessels became visible after the addition of NG.

To examine the potential direct effects of β2GP1 on blood vessels, an in vivo model system that monitored blood vessel hemodynamics using real-time imaging was developed. In this in vivo model system, normal mice were anesthetized and the mesentery was draped on the specimen stage of a dissecting microscope. FIG. 8 shows blood vessel architecture of the normal mesentery. To assess the effects of tumor-derived growth factors on the architecture of the normal vasculature, vascular endothelial growth factor (VEGF) and nitroglycerin (NG) were applied directly to the tissue and recorded under a dissecting microscope. Images were collected in real-time for 1 hour after wetting the area of interest with VEGF (0.1 µg/mL; ~0.05 mL) or NG (40 µg/mL). Consistent with the known vessel dilation properties of VEGF/VPF and NG, analysis of videotapes revealed what appeared to be increased tortuousness of vessels and a significant increase in the dilation of small capillaries some of which were barely visible before the addition of VEGF or NG.

Frames of interest were digitized and captured as shown in FIG. 8. Areas of obvious dilation after treatment with VEGF are marked with arrows (FIG. 8, left panels). Note the increased tortuousness of vessels after the addition of VEGF, marked by the squiggly trace following some vessels in the VEGF frame (FIG. 8 lower left panel), which was copied and superimposed on the same vessel in the zero time image (FIG. 8 upper left panel). Obvious areas of dilated vessels after treatment with NG are also marked, although the magnitude of change is not as great as that obtained with VEGF. The circled area marks an area where small vessels became visible after the addition of NG (FIG. 8, right panels).

Figure 9:
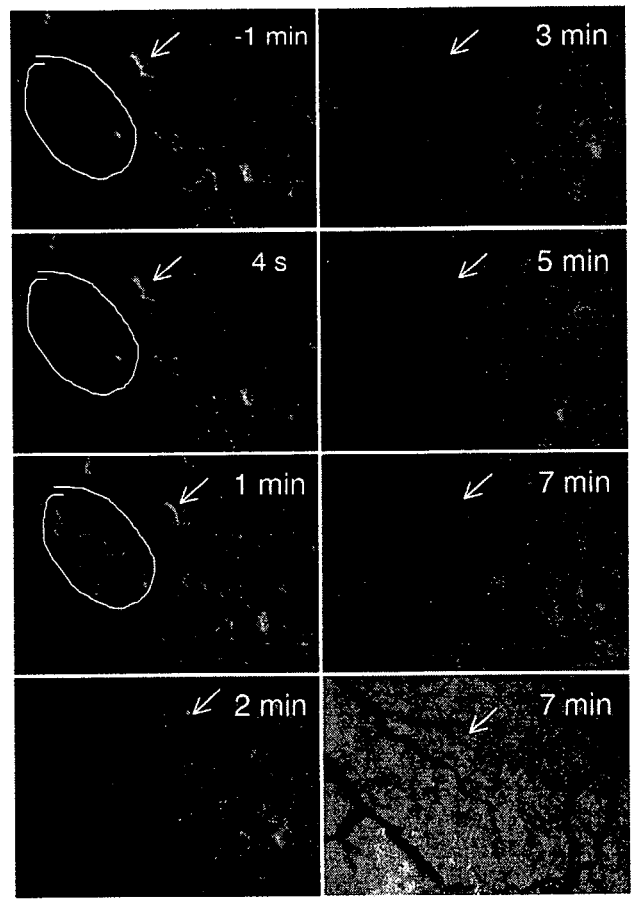
FIG. 9. Kinetics of VEGF-induced angioectasia. Control mice were injected intravenously with fluorescein-conjugated human serum albumin (FITC-HAS), anesthetized, and prepared as described in FIG. 8. VEGF was applied at time zero, the area was videotaped and frames of interest were digitized and captured. There are several notable features in this sequence. First, note the relatively sparseness of the fluorescent vessels in the circled area before the addition of VEGF. At 1 minute, the density of fluorescent vessels in this area increased significantly and then began to gradually disappear over the next 5 minutes. Second, note the fluorescent blood vessel marked with the white arrow before the addition of VEGF (−1 min). Within 2 minutes after the addition of VEGF the fluorescence disappeared (due to the vessel filling with red blood cells and quenching of FITC-HSA). At 7 minutes, a diffuse area of fluorescence seems to appear which may represent increased vessel permeability and leakage of small plasma proteins (FITC-HSA) to the surrounding tissue. The light image taken at 7 minutes shows a newly visible (red blood cell filled) blood vessel.

To better monitor small vessels and the kinetics of VEGF-induced angioectasia, control mice were injected with 0.1 mg of human serum albumin 16 hours and 4 hours before they were injected intravenously with FITC-HSA. After one hour, the mice were anesthetized and prepared as described above. In many cases, only very few fluorescent vessels could be seen by fluorescent microscopy in these mice. VEGF was applied at time zero, the area was videotaped, and frames of interest were digitized and captured. There are several notable features in this sequence as shown in FIG. 9. First, note the relative sparseness of the fluorescent vessels in the circled area before the addition of VEGF. Within seconds after the addition of VEGF, however, an increasing number of fluorescent vessels appeared. After 1 minute, the density of fluorescent vessels in this area increased significantly, and then began to gradually disappear over the next 5 minutes. Simultaneously, there was an increase in diffuse fluorescence throughout the specimen because of leakage of the FITC-HSA from the vasculature to the surrounding tissue. Second, note the fluorescent blood vessel marked with the white arrow before the addition of VEGF (−1 minute). Within 2 minutes after the addition of VEGF the fluorescence disappeared. This was because this vessel quickly filled with red blood cells, the hemoglobin of which quenches the fluorescence of FITC-HSA. After hemoglobin quenches fluorescein fluorescence, the vessels are visible only by light microscopy. After 7 minutes, a diffuse area of fluorescence seems to appear which may represent increased vessel permeability and leakage of small plasma proteins (FITC-HSA) to the surrounding tissue. The light image taken at 7 minutes also shows a newly visible (red blood cell filled) blood vessel.

These finding suggests the preexistence of a regulated blood supply, which under normal conditions, is closed. Conceivably, these vessels open upon an angiogenic stimulus such as exogenously-supplied VEGF, and also potentially with endogenously supplied factors from growing tumors. These data raise the possibility that an actively growing tumor recruits a collateral blood supply from an existing network of closed vessels reminiscent to "closed blood vessels" of smooth muscle (Krogh A. A Contribution to the physiology of the capillaries. Noble Lecture, December 11. 1920).

Figure 10:
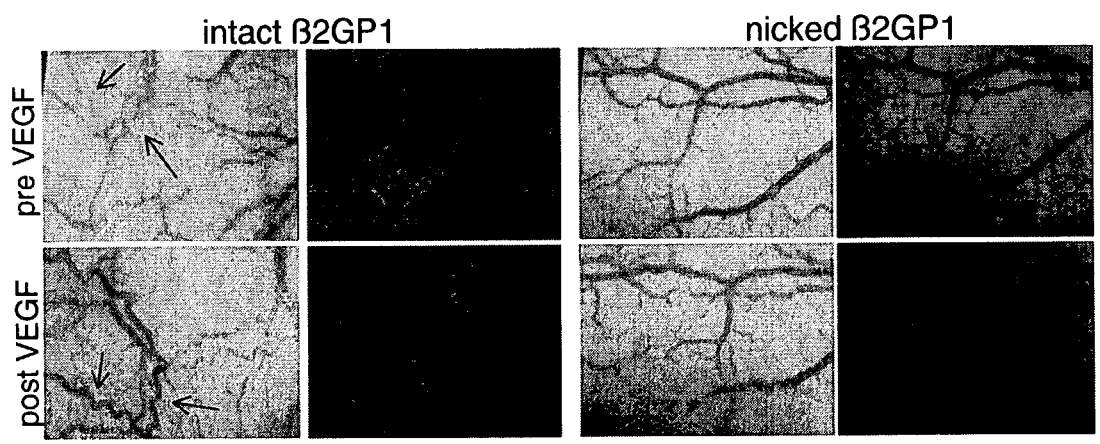
Figure 11:
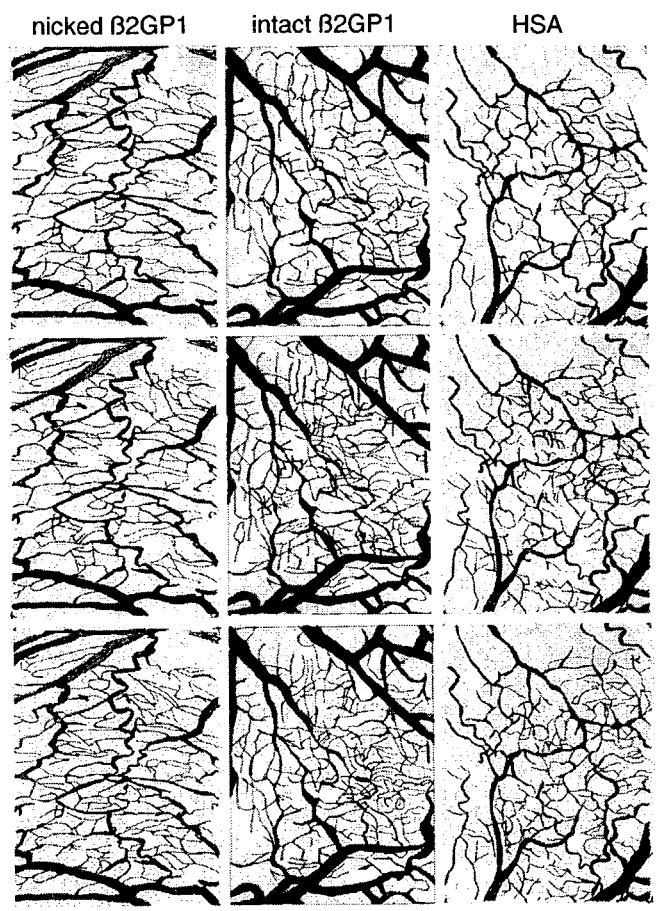
FIG. 11. Vessel pattern in VEGF-treated mesentery. To better describe typical patterns of fluorescent and "red" vessels, multiple frames from VEGF-induced angioectasia in mice injected with intact β2GP1, N-β2GP1, and HSA were carefully traced. Mice injected with intact β2GP1 or HSA generally showed a small number of fluorescent vessels that immediately increased upon addition of VEGF. No fluorescent vessels were seen in mice pretreated with N-β2GP1. Top, before; middle, 1 minute after; and bottom, 7 minutes after the addition of VEGF, respectively.

Next, the effect of β2GP1 and N-β2GP1 was examined on this in vivo model system. Mice that were injected intraperitoneally with 0.1 mg of β2GP1 or N-β2GP1 16 hours and 4 hours before the experiment were injected intravenously with FITC-HSA. The mice were then prepared as described above, and videotaped throughout the application of VEGF. Interestingly, the opening of vessels (vessel dilation and leakage of FITC-HSA) was completely inhibited in animals treated with N-β2GP1, but not in those treated intact β2GP1 (FIGS. 10 and 11). To better describe typical patterns of fluorescent and "red" vessels, multiple frames from VEGF-induced angioectasia in mice injected with intact 02GPI, N-02GPI, and HSA were carefully traced (FIG. 11). Mice injected with intact β2GP1 or HSA generally showed a small number of fluorescent vessels that immediately increased upon the addition of VEGF and then slowly disappeared as they filled with red blood cells and became visible under light microscopy. No fluorescent vessels were seen in animals pretreated with N-β2GP1, nor were any apparent differences in the degree of vessel dilation noticed over the time course of the experiment.

Figure 12:
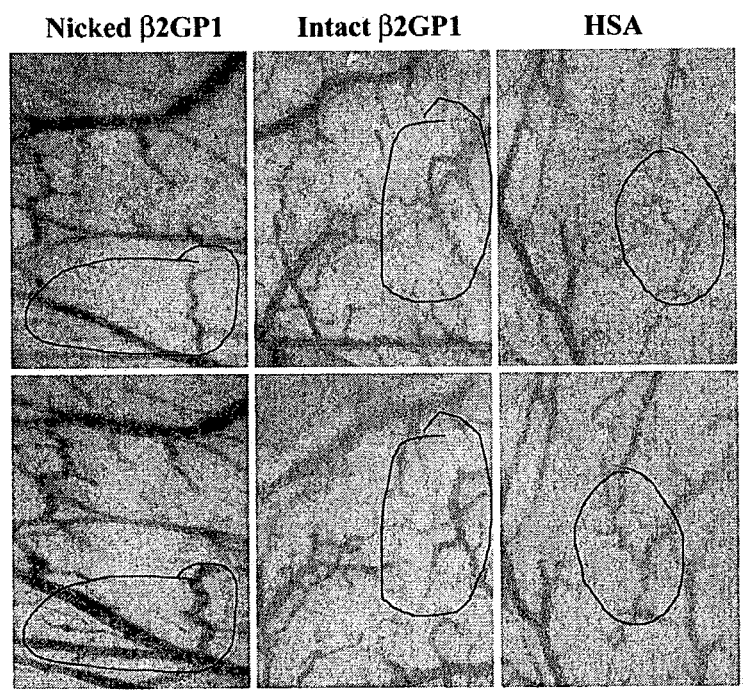

To determine if inhibition of angioectasia by N-β2GP1 was specific for tumor-derived factors (e.g., VEGF), the experiments described above were repeated with nitroglycerin (NG). Mice were injected intraperitoneally with 0.1 mg of β2GP1, N-β2GP1, or HSA 16 hours and 4 hours before the experiment. The mice were then prepared as described in FIG. 8, and videotaped before and after (0.5 hour) the application of NG. The circles in FIG. 12 mark areas of obvious vessel dilation in all of the animals studied. Therefore, unlike the inhibition of VEGF-induced angioectasia shown above, pretreatment of mice with N-β2GP1 was without effect on chemically-induced vessel dilation (FIG. 12). This suggests that the inhibitory effect of β2GP1 on blood vessel dilation is independent of the mitochondrial aldehyde dehydrogenase pathway in smooth muscle cells (Chen et al., *Proc. Natl. Acad. Sci.* (USA) 99:8306–11, 2002).

VEGF was initially purified and identified on the basis of its ability to induce increased vascular permeability and eventual leak of intravessel contents (Dvorak et al., *Current Topics in Microbiology & Immunology* 237:97–132, 1999; Ferrara, *Kidney International* 56:794–814, 1999; Ferrara, *Current Topics in Microbiology & Immunology* 237:1–30, 1999). It was therefore originally coined "vascular permeability factor" (VPF), a characteristic highlighted in the in vivo experiments presented above. Blood vessels in many tumors are abnormal in the sense that they have numerous fenestrations and openings, defects that make them inherently leaky. Although more studies are needed to assess the relative contribution of angioectasia on tumor growth, the data presented above raise the possibility that, in addition to true angiogenesis, angioectasia could provide a significant contribution to tumor "vascularity." If so, inhibition of angiogenesis and angioectasia with plasmin-cleaved (nicked) β2GP1 might provide a heretofore-unrecognized modality for cancer treatment.

EXAMPLE 6

Defining the Active Regions of β2GP1

To better understand the therapeutic potential of β2GP1 to inhibit or prevent endothelial cell proliferation, as well as to treat angiogenesis, angioectasia, and tumor growth, it is important to better define the active forms and mechanisms of action of β2GP1. To achieve this goal, expression cloning of domain-deleted β2GP1 will be done to determine the minimal structural unit of the protein required for inhibition of angiogenesis/angioectasia. Preparative amounts of these domain-deleted proteins can be isolated using site-specific enzymatic cleavage. Site-directed mutagenesis of human β2GP1 has clearly demonstrated that domain V carries the lipid binding region within the lysine-rich sequence motif (281CKNKEKKC288) and a hydrophobic loop (313LAFW316) important to partial intercalation of the protein into the lipid bilayer. Because the anti-angiogenic properties of β2GP1 may be dependent on cleavage at residues Lys 317/Thr 318 which results in a significant decrease in lipid and membrane binding, it is possible that the activity of N-β2GP1 depends on a concomitant alteration in the protein's structure that might be propagated to one or more domains.

Figure 13:
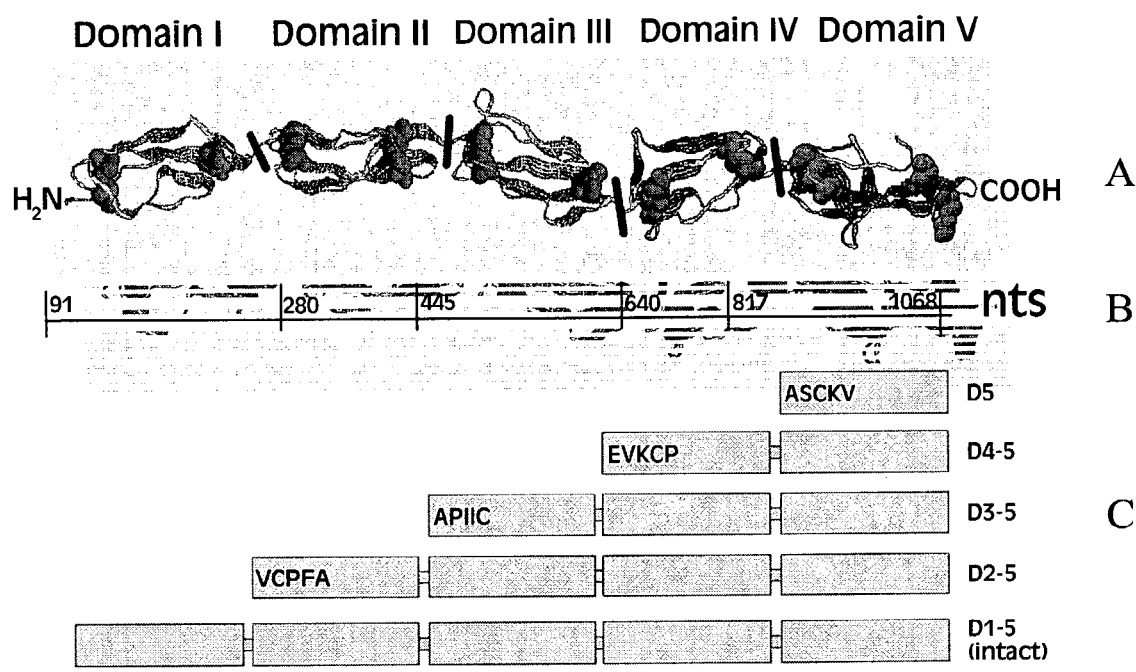
FIG. 13. Construction of β2GP1 domain deleted mutants. Deletion constructs were initiated from the linker region between the disulfide-linked domains in order to keep distal domains intact. The approximate locations of cut sites are illustrated by bold vertical bars in panel A. Panel B shows the schematic diagram of the primer start site of the respective PCR amplification products. Panel C maps the domains present in the different constructs with their respective N-terminal amino acid sequence. Constructs were based on human liver cDNA EMBL accession no. X57847.
Figure 14:
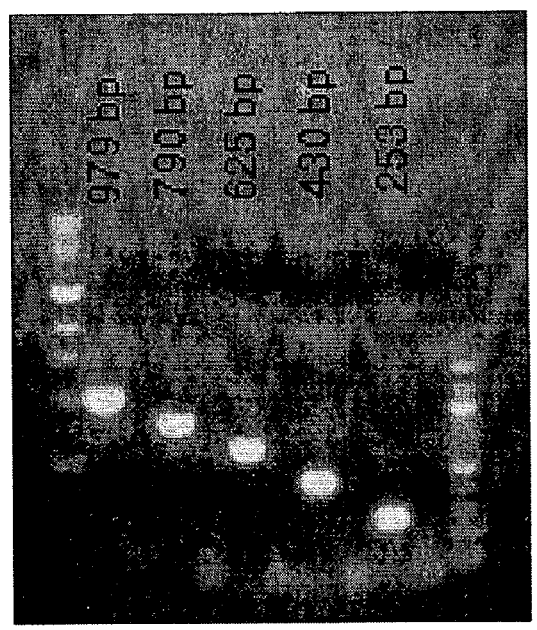
FIG. 14. Identification of PCR products set forth in FIG. 12. The PCR amplified products representing the sequential domains described in Example 4 were analyzed by agarose gel electrophoresis (cDNA fragments 979 bp, 790 bp, 625 bp, 430 bp, and 253 bp in length, respectively). The far left and right lanes are 1 kb and 100 bp ladders, respectively.
Figure 15:
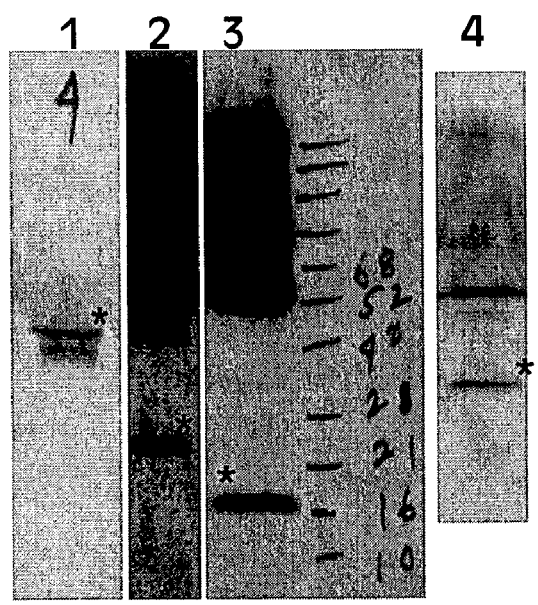
FIG. 15. Analysis of recombinant proteins of β2GP1 domain deleted mutants. Gels 1 and 4 show secreted recombinant full length protein and domain V, respectively. Gels 2 and 3 show constitutively-expressed recombinant domains 3–5 and 4–5, respectively (see FIG. 12). Asterisks indicate the recombinant products.

To identify the minimal structural unit of N-β2GP1 responsible for its anti-angiogenic properties, deletion mutants retaining domain V of the protein were constructed. The rationale for the design of these mutants is to specifically delete sequential domains from the N-terminus and determine which recombinant protein looses its ability to inhibit endothelial cell proliferation and angiogenesis. For example, if the critical motif resides in domain III, then Lys 317/Thr 318-cleaved recombinant proteins D1–5, D2–5 and D3–5 as shown in FIG. 13 should be inhibitory, whereas deletions distal to domain III (D4–5 and D5) would not. Briefly, five cDNA fragments, 979 base pairs (nucleotides 91–1069; D1–5), 790 bp (nucleotides 280–1069; D2–5), 625 bp (nucleotides 445–1069, D3–5), 430 bp (nucleotides 640–1069; D4–5) and 253 bp (nucleotides 817–1069, D5), were derived by PCR (see FIG. 14) and subcloned into the pAC 5.1/V5-HisA vector (Invitrogen). The original β2GP1 gene used was disclosed in Mehdi et al., *Gene* 108:293–298, 1991, incorporated herein by reference. The authenticities of the individual clones were determined by sequence analysis. Some of the recombinant proteins have been expressed in the *Drosophila* S2 expression system (DES, Invitrogen) (see FIG. 15). These recombinant proteins will be used in experiments such as those outlined in Examples 1–3 to determine which domains of the β2GP1 protein inhibit, treat, or prevent endothelial cell proliferation, angiogenesis, angioectasia, and/or tumor growth.

Figure 16:
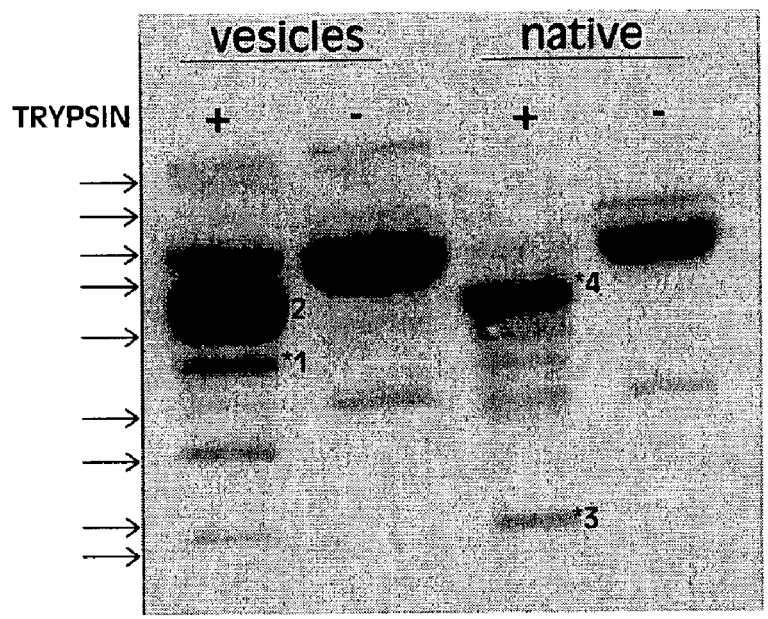
FIG. 16. Generation of β2GP1 domain-deleted mutants with trypsin. Two major fragments were generated with lipid-bound β2GP1 digested with trypsin: a ~30 kDa fragment (*1) with the N-terminal sequence DTAVFECLPQH, and a ~40 kDa (*2) fragment with the N-terminal sequence YTTFEYPNTIS. These two peptide fragments are consistent with single polypeptides encompassing domains III–V and II–V, respectively. Two major fragments were also generated with native unbound β2GP1: a ~10 kD a fragment (*3) and a ~40 kDa fragment (*4), both of which had the N-terminal sequence GRTCPKPDDLP. This sequence is consistent with polypeptides encompassing domain I and domains I-IV. Molecular weight markers (arrows) are 121, 86, 69, 52, 40, 28, 22, 17 and 9 kDa.

In an effort to rapidly generate large amounts of domain-deleted β2GP1, site-specific enzymatic hydrolysis of intact β2GP1 and intact β2GP1 bound to negatively charged lipid vesicles was carried out. The rational for generating different domains by this technique is based on our observations that β2GP1 undergoes dramatic structural alterations upon binding to its lipid ligand (Lee et al., *Biochim. Biophys. Acta* 1509:475–84, 2000). To generate the β2GP1 bound to vesicles, β2GP1 (1 mg) was incubated with sonicated PS/PC (7/3 mol/mol) vesicles (1 mg/mL) for 2 hours in 10 mM Tris pH 7.1. The precipitated vesicles were washed free of unbound protein and subsequently incubated with trypsin (1/100) at 37° C. for 20 hours. Native β2GP1 was also incubated with trypsin for 20 hours. SDS-PAGE analysis of these digests yielded significantly different profiles (FIG. 16). Two major fragments were generated with lipid-bound β2GP1. A ~30 kDa fragment (*1) with the N-terminal sequence DTAVFECLPQH, and a ~40 kDa (*2) fragment with the N-terminal sequence YTTFEYPNTIS. These two peptide fragments are consistent with single polypeptides encompassing domains III-V and II-V, respectively. With native unbound β2GP1, ~10 kDa (*3) and ~40 kDa (*4) polypeptides were recovered. Both fragments had the same GRTCPKPDDLP N-terminus consistent with polypeptides encompassing domain I and domains I–IV. Since the fragments formed in the presence of lipid contain "protected" domain V, these polypeptides together with the recombinant proteins will be used (before and after plasmin cleavage) to determine which domains of β2GP1 are critical to its anti-angiogenic/anti-angioectasia activity.

To determine whether both intact β2GP1 and N-β2GP1 are effective in inhibiting endothelial proliferation, angiogenesis, angioectasia, and/or tumor growth, or alternatively whether N-β2GP1 alone is the active anti-angiogenic/anti-angioectasia form of the protein, the minimal structural unit of the protein that is required to inhibit angiogenesis/angioectasia and tumor growth will be determined, in part by using the domain-deleted β2GP1 constructs disclosed above. To help answer this question, gel foam implants containing intact β2GP1 will be implanted into mice as described in Example 1, and removed at 2 day intervals. After removal, the ratios of intact to nicked protein will be determined by amino acid sequence analysis of extracted protein and staining with monoclonal antibodies specific to intact β2GP1 and N-β2GP1, which can be prepared using methods well known to those of skill in the art (see, e.g., Horbach et al., *Throm. Haemostasis* 81:87–95, 1999, incorporated herein by reference).

For antibody staining, implants will be removed, frozen in liquid $N_2$, thin sectioned, and directly stained with fluorescein-labeled anti-(intact) β2GP1 and rhodamine-labeled anti-N-β2GP1. Protein ratios will be determined by quantitative fluorescence microscopy ratio imaging. For sequence analysis, proteins will be extracted from the implants with 1% SDS, run on acrylamide gels, and transferred to PDF membranes. Protein ratios will be determined by the relative ratio of the N-terminal sequence of intact β2GP1 (GRTCP-KPDDLP) and the N-terminal sequence generated (by protease treatment) at the 317–318 clip site of N-β2GP1 (TDASDVKPP). Standard β2GP1 will be purified as described (see Polz et al., *Int. J. Biochem.* 11:265–270, 1980, incorporated herein by reference) and standard N-β2GP1 will be prepared by treatment with plasmin (see Ohkura et al., *Blood* 91:4173–4179, 1998, incorporated herein by reference), and purified by HPLC.

Once the active form of the protein is unequivocally determined, the ability of the recombinant (plasmin-cleaved) domain-deleted proteins to inhibit angiogenesis into the gel foam implants will also be determined. It is possible that the propensity of the increasingly smaller sequential domain-deleted recombinant proteins to diffuse out of the implants might become problematic. Therefore, diffusion of the proteins over the time course of the experiment will be monitored by including trace amounts of isotopically-labeled ($^{125}$I-) protein. Should the smaller proteins (~10 kDa—~40 kDa) diffuse significantly faster than the full length protein (~50 kDa), the fragments will be covalently coupled to albumin using n-hydroxysuccimidyl-human serum albumin, which will effectively increase fragment size.

To investigate which endothelial cell-dependent pathway may be involved in inhibiting neovascularization into growing tumors, the following in vitro assays can by used to assess the effect of β2GP1, N-β2GP1, and their domain-deleted recombinant fragments against human [umbilical cord (HUVEC) and microvascular (HMVEC)] and mouse microvascular endothelial cells. These endothelial cells will include cells from solid tumors or organs of particular interest (e.g., lungs in the case of B16 melanoma, liver with KM12L4a, and kidney with SN12 and RENCA). A growth inhibition and apoptosis assay can be done using endothelial cells ($1.5 \times 10^3$) plated in a 96-well plate with 100 µl of medium. After 24 hours (day 0), the test compounds will be added. Cell growth over 72 hours will be determined by staining with 3-(4,5-Dimethylthiazol-2-yl)-2,5-diphenyltetrazolium bromidethiazolyl blue (MTT assay). Absorbance at 570 nm will be determined with an ELISA reader (Dynatech Laboratories). Duplicate plates can be assessed for apoptosis using the APOPercentage apoptosis assay (Biocolor, Belfast Ireland). A tube formation assay can be done using 96-well plates coated with ice-cold Matrigel (60 µl of 10 mg/ml; Collaborative Labs) and incubated at 37° C. for 30 min for polymerization. The test compounds and endothelial cells will be plated on the polymerized matrigel, and after 24 hours of incubation, triplicate images will be processed. The effect of β2GP1 will be compared to untreated controls by measuring tube length and number of junctions. Finally, a cell migration assay can be determine using 48-well Boyden chamber and 8 µm collagen-coated polycarbonate filters. The bottom chamber wells will receive medium alone (baseline) or medium containing a chemo-attractant (bFGF, VEGF). The top chambers receive endothelial cells with or without β2GP1. After 5 hours at 37° C., the membrane will be washed, fixed, and stained in Diff-Quick. The filter will be placed on a glass slide with the migrated cells facing down. Negative unstimulated control values will be subtracted from stimulated control and β2GP1-treated values.

EXAMPLE 7

The Effect of Domain-Deleted Fragments of β2GP1 on Endothelial Cells In vivo

The ability of the domain-deleted recombinant fragments of β2GP1 generated in Example 6 to inhibit VEGF-induced angioectasia will be monitored and recorded in real-time as describe in Example 5. Briefly, mice will be injected with various amounts of N-β2GP1 and its domain-deleted fragments at 16 hours and 4 hours before the experiment. The mice will then be injected with fluorescein-albumin. Blood vessel dilation and plasma leak will be monitored in the exposed mesentery by simultaneous light and fluorescence microscopy immediately before and following the addition of VEGF. Monitoring will be controlled with an electronically actuated shutter mechanism that switches illumination from a 490 nm interference filtered xenon lamp to a broadband visible source at 2 second intervals. By monitoring the rate of closed vessel to plasma flow (green fluorescence) and plasma flow to red cell flow (fluorescein-negative, red visible), vessel dynamics, kinetics and bore size can be accurately quantified.

To assess vascular permeability in these mice, after the mice are treated with the domain-deleted fragments of β2GP1 as described above, they will be injected intradermally with VEGF, NG, histamine, Angiopoietin-1, or albumin. Vascular permeability will then be determined after injecting Evans blue (Thurston et al., *Science* 286:2511–4, 1999, incorporated herein by reference).

Once the minimal inhibitory size of the domain-deleted fragments of β2GP1 is determined, synthetic peptides of overlapping sequence will be constructed and further tested in the studies described above with the goal of identifying relatively short peptide sequences capable of inhibiting angioectasia. These studies will likely be very dependent on the size of the minimal structural unit. For example, if only one or two domains of N-β2GP1 is required to inhibit angioectasia, constructing a series of overlapping peptides that encompass the entire polypeptide would be worthwhile.

EXAMPLE 8

In vivo Angiogenesis Assay

The ability of intact β2GP1 and N-β2GP1, as well as intact and nicked domain deleted mutants of β2GP1, to inhibit angiogenesis will be tested in the gel foam plug assay as described in Example 1 in the presence and absence of pro-angiogenic molecules. Briefly, 5×5×7 mm pieces of sterile gel foam absorbable sponges (Pharmacia & Upjohn, Peapack, N.J.) will be hydrated overnight at 4° C. in phosphate-buffered saline (PBS). After removing excess buffer, 0.4% agarose (100µl) containing saline (control), the various β2GP1 preparations, and one of the following proangiogenic molecules: basic fibroblast growth factor (bFGF), vascular endothelial growth factor (VEGF), endothelial growth factor (EGF), tumor growth factor-alpha (TGF-α), or platelet-derived growth factor (PDGF) (R&D Systems, Minneapolis, Minn.), will be aliquoted onto each sponge cube. After hardening at room temperature, the sponge cubes will be implanted in mice into subcutaneous pockets formed on both sides of the chest (2–3 cm away from the incision). One gel foam sponge will be inserted into each pocket, and the wound will closed with surgical metal clips. Fourteen days later, the mice will be sacrificed and the gel foam sponges will be recovered, counted for $^{51}$Cr to assess vascular volume and neovascularization, and finally frozen in OCT compound.

EXAMPLE 9

Determining the Mechanism by which β2GP1 Inhibits Angiogenesis

A. Inhibition of Growth Factor/Receptor Interactions

Although the results of Examples 1 and 4 clearly suggest that β2GP1 inhibits endothelial cell angiogenesis, the results of the in vivo blood dilation studies shown in Example 5 suggest that smooth muscle cells could be influenced by β2GP1. Thus, other than the possible differential interactions of β2GP1 and N-β2GP1 on endothelial cells, β2GP1 might inhibit the interaction of VEFG with one or more of its receptors on endothelial cells, smooth muscle cells, or both.

Figure 20:
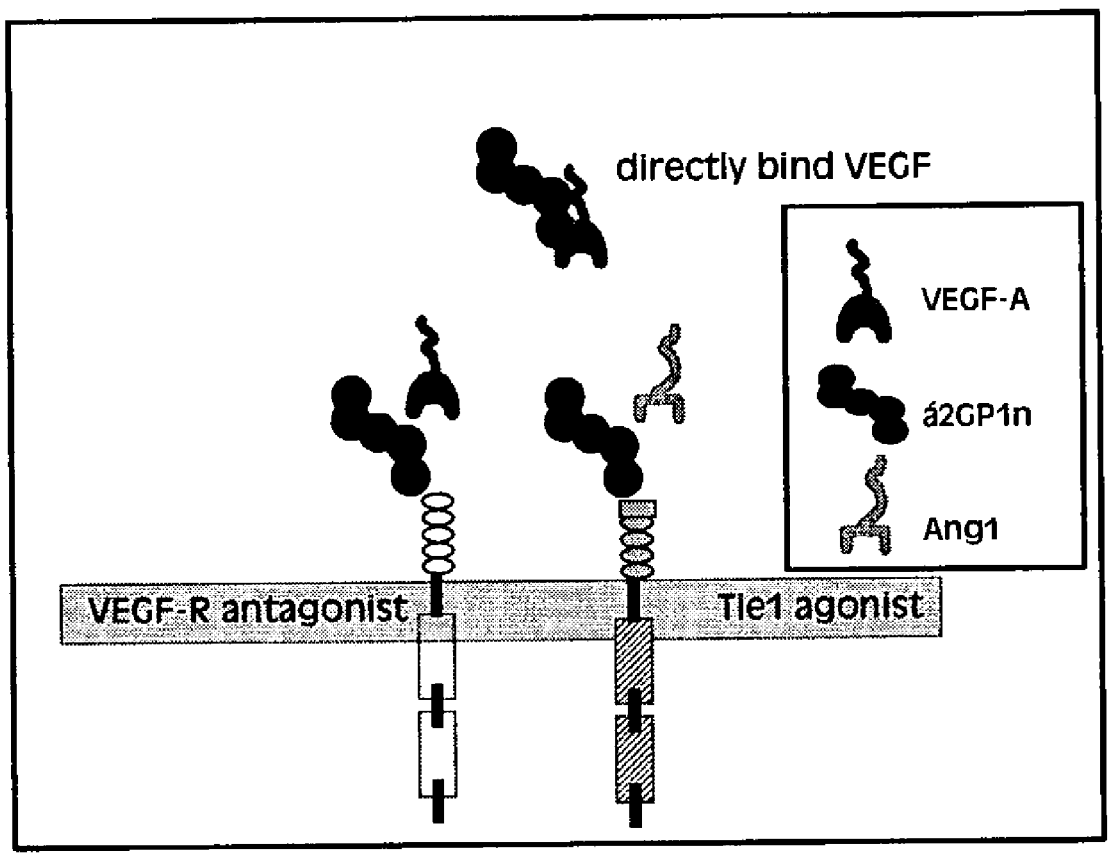
FIG. 20. Potential mechanism by which N-β2GP1 inhibits endothelial cell angiogenesis/angioectasia. The possibilities are: (i) direct binding to VEGF, which inhibits VEGF binding to its receptor; (ii) binding to VEGF-R (receptor antagonist); or (iii) binding to Tie-1 (receptor agonist).

The major endothelial cell receptors involved in initiating signal transduction cascades in response to VEGF is a family of closely related receptors with overlapping specificities known as VEGFR-1 (flt-1), VEGFR-2 (KDR), and VEGFR-3 (flt-3). These receptors bind VEGF-A, which is also known as vascular permeability factor (VPF), VEGF-B, and VEGF-C, respectively (Veikkola et al., *Cancer Res.* 60:203–12, 2000; Li and Eriksson, *International Journal of Biochemistry & Cell Biology* 33:421–6, 2001). Angiopoietins (Ang's) are another family of endothelial growth factors that are ligands for the receptor tyrosine kinase, Tie-2 (Davis et al, *Cell* 87:1161–9, 1996; Yancopoulos et al., *Nature* 407:242–8, 2000). Unlike VEGF, Ang's do not stimulate endothelial cell growth, but instead likely play a role in blood vessel stabilization. For example, blood vessel leaks induced by VEGF are inhibited by Ang-1 (Thurston et al., *Nature Medicine* 6:460–3, 2000). Although not wishing to be bound by any particular theory, given the dramatic inhibitory effect of N-β2GP1 on VEGF-induced vascular dilation/permeability, N-β2GP1 might act as (i) a VEGF binding protein that shields VEGF from interacting with its receptor; (ii) operates as a VEGF-R antagonist; or (iii) an Ang-1 agonist (FIG. 20).

To determine whether N-β2GP1 binds to VEGF, VEGF will be incubated with $^{125}$I-labeled intact β2GP1 and N-β2GP, and the ability of specific VEGF (Santa Cruz) and β2GP1 antibodies to co-precipitate both proteins will be assessed. In the case of anti-VEGF, precipitation of $^{125}$I will be determined. With anti-N-β2GP, the precipitate will be washed, run on SDS-PAGE, transferred to nitrocellulose membranes, and probed with anti-VEGF using conventional techniques. If the results of these experiments show that N-β2GP1 does not bind VEGF directly, the following experiment will be performed. VEGFR-2 autophosphorylates and becomes activated upon binding to specific ligands. Endothelial cells will be incubated with VEGF (~10 ng/mL) in the presence or absence of N-β2GP, and the ratio of phospho-VEGFR (Cell Signaling Technology) to VEGFR (Cascade Biologics) will be determined by quantitative immunoprecipitation and/or western blot analysis. Alternatively, cells will be labeled with $^{32}$P and direct phosphorylation of the receptor will be determined by immunoprecipitation of $^{32}$P-VEGFR.

If the results of these experiments demonstrate β2GP1-dependent inhibition of phosphorylation, additional experiments will be performed to determine whether N-β2GP1 binds to Tie-1 (agonist) or VEGFR (antagonist). Endothelial cells will be incubated with N-β2GP1 with or without VEGF and/or Ang-1. Then the cells will be solubilized in non-ionic detergent and immunoprecipitated with anti-N-β2GP1. Following SDS-PAGE, the proteins will be transferred to nitrocellulose membranes and probed with Tie-1 and VEGFR antibodies using conventional techniques.

Another approach to identify cell surface epitopes that bind β2GP1 is to directly crosslink cell bound β2GP1 with its "nearest neighbor" by reaction with hetero- or homo-bifunctional crosslinkers such as BS3. Briefly, unlabeled or radioiodinated-N-β2GP1 will be incubated with endothelial cells (in the presence or absence of VEGF, Ang-1, etc.), washed, and then immobilized with the crosslinking reagent. The cells will be solubilized, and the β2GP1 complexes will be isolated by affinity chromatography on anti-β2GP1 columns. If disulfide crosslinkers are used, the linked target epitope will be released with DTT. Proteins will also be identified by molecular weight, sequence analysis, and by western blotting using antibodies against suspect target proteins (e.g., VEGFR, Ang-1, annexin II).

B. Model Membrane Studies

Several studies have indicated that β2GP1 binds different target ligands through one or more binding sites. For example, both domain V and domain I participate in its interaction with anionic phospholipids (Hong et al., *Biochemistry* 40:8092–8100, 2001; Hoshino et al., *J. Mol. Biol.* 304:927–939, 2000; Hagihara et al., *J. Biochem.* 118:129–136, 1995; Hagihara et al., *Lupus* 4 Suppl 1:S3–S5, 1995; Hagihara et al., *J. Biochem.* 121:128–137, 1997), domain I (Cys-32 through Cys-47) binds calmodulin (Rojkjaer et al., *Biochim. Biophys. Acta* 1339:217–225, 1997; Klaerke et al., *Biochim. Biophys. Acta* 1339:203–216, 1997), and domain IV binds lipid/β2GP1 complex-dependent "antiphospholipid" antibodies. β2GP1 also binds megalin (Moestrup et al., *J. Clin. Invest.* 102:902–909, 1998) and annexin II (Ma et al., *J. Biol. Chem.* 275:15541–15548, 2000) through as yet unidentified sites. Because the vascular endothelium of tumors express both PS (Ran et al., *Cancer Res.* 58:4646–4653, 1998) and annexin II (Dreier et al., *Histochemistry & Cell Biology* 110:137–148, 1998; Hajjar et al., *J. Biol. Chem.* 271:21652–21659, 1996), β2GP1 may bind to endothelial cells through both ligands simultaneously, thereby protecting the cell from antiangiogenic stimuli that might involve PS/annexin II interactions.

Figure 17:
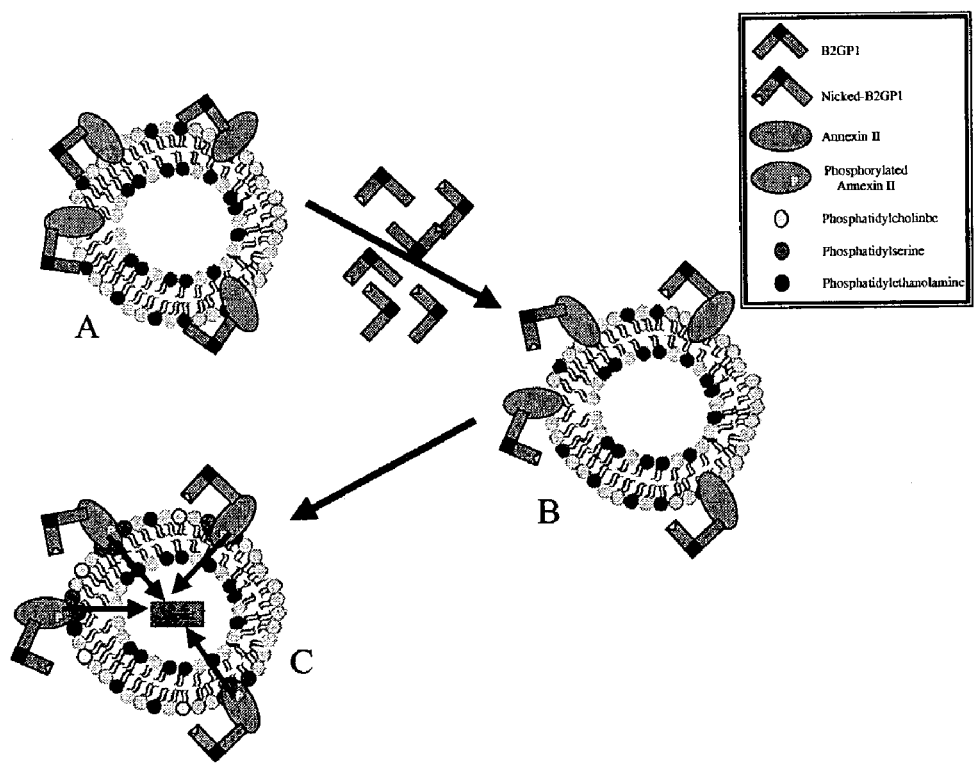
FIG. 17. Hypothetical β2GP1-dependent mechanism for the inhibition of endothelial cell angiogenesis/angioectasia. (A) β2GP1 in tumor vascular endothelial cells binds to both annexin II and PS, and prevents PS/annexin TI interactions. (B) Cleavage of β2GP1 with endogenous plasmin results in release of PS. Alternatively, exogenously-supplied N-β2GP1 competes for endogenous (intact) β2GP1 binding to annexin II. This results in its dissociation from PS because of its low affinity binding (~$10^{-6}$ M) in the absence of multivalent interactions. C) This enables the association of PS with annexin II that leads to a sequence of intracellular events that culminates in inhibition of angiogenesis.

Conceivably N-β2GP1 binds to the cells only through annexin II because it cannot bind PS because it is cleaved in domain V (Ohkura et al., *Blood* 91:4173–4179, 1998; Hagihara et al., *J. Biochem.* 118:129–136, 1995). Thus, although not wishing to be bound by any particular theory, it is possible that when N-β2GP1 is administered to tumor-bearing mice, it competes with endogenous β2GP1 for binding to annexin II. It is possible that such a scenario could favor annexin II/PS interactions that may lead to signaling pathways (Akiba et al., *British Journal of Pharmacology* 131:1004–1010, 2000; Bellagamba et al, *J. Biol. Chem.* 272:3195–3199, 1997; Chiang et al., *Mol. Cell Biochem.* 199:139–147, 1999), which results in the induction of PS-induced apoptosis (Uchida et al., *J. Biochem.* 123:1073–1078, 1998; Miyato et al., *FEBS Letters* 504:

73–77, 2001). This hypothetical model of β2GP1-dependent mechanism for the inhibition of angiogenesis/angioectasia is shown in FIG. 17.

Figure 18:
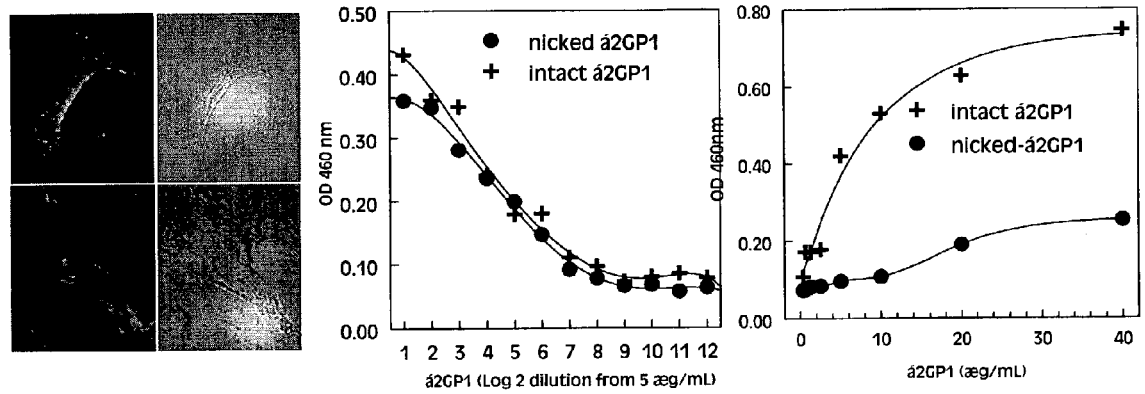
FIG. 18. Left panel. Vascular endothelial cells were incubated with intact β2GP1 (top) or N-β2GP1 (bottom), washed, and then stained with fluorescein-conjugated anti-β2GP1 (Left, fluorescence; right: light). Both intact β2GP1 and N-β2GP1 bind endothelial cells. Middle panel. ELISA plates coated with intact β2GP1 or N-β2GP1 were blocked with 1% ovalbumin and biotin labeled annexin was added. The plates were washed after 1 hr and developed with peroxidase-avidin. Both intact β2GP1 and N-β2GP1 bind annexin. Right panel. Phosphatidylserine-coated ELISA plates were blocked with 1% ovalbumin and incubated with intact β2GP1 or N-β2GP1. Protein binding to the plates was determined with rabbit β2GP1 antibodies followed by peroxidase-conjugated anti-rabbit 1 g. Note that only intact β2GP1 was able to bind lipid, and the comparatively significant decrease in the binding of N-β2GP1.

This idea is supported from a thermodynamic standpoint since high affinity binding of β2GP1 (~$10^{-9}$ M) requires "multiple" binding sites (Willems et al., *Biochemistry* 35:13833–42, 1996) that could be provided by multivalent PS-β2GP1-annexin II interactions. Upon cleavage with plasmin, however, β2GP1 loses its lipid binding capacity and undergoes structural alterations that could enhance its binding to annexin II. Physiologically, such a scenario could be operative during normal wound healing through the action of endogenously activated plasmin. From an interventional standpoint, the affinity of N-β2GP1 for annexin II could be significantly greater than that of intact β2GP1. Although still inconclusive, the results of recent experiments seem to support this hypothesis as shown in FIG. 18.

Vascular endothelial cells were incubated with intact β2GP1 or N-β2GP1 for 1 hour at 4° C. The cultures were then washed and stained with fluorescein-conjugated anti-β2GP1. As shown in the left panel of FIG. 18, both intact β2GP1 (top) and N-β2GP1 (bottom) bind endothelial cells (left, fluorescence; right: light). Next, ELISA plates were coated with intact β2GP1 or N-β2GP1. The plates were blocked with 1% ovalbumin and biotin labeled annexin was added. After 1 hour, the plates were washed and developed with peroxidase-avidin. As shown in the middle panel of FIG. 18, both intact 32GP 1 and N-β2GP1 bind annexin II. Finally, ELISA plates were coated with phosphatidylserine, blocked with 1% ovalbumin, and incubated with intact β2GP1 or N-β2GP1 preparations. Protein binding to the plates was determined with rabbit β2GP1 antibodies followed by peroxidase-conjugated anti-rabbit 1 g. As shown in the right panel of FIG. 18, only intact β2GP1 binds lipid, with a comparatively significant decrease in the binding of N-β2GP1.

Figure 19:
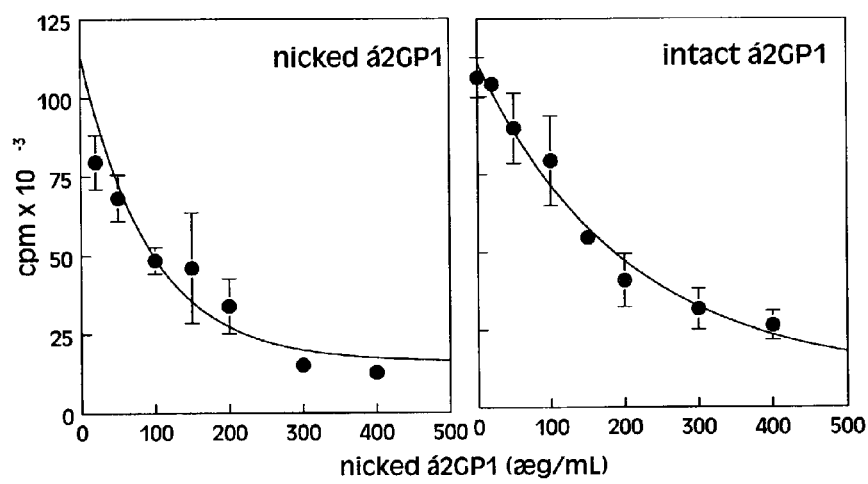
FIG. 19. Binding of β2GP1 to endothelial cells. Both intact β2GP1 and N-β2GP1 were labeled with $^{125}$I, and added in the presence of increasing concentrations of unlabeled N-β2GP1 to endothelial cells. Uptake was determined by scintillation counting. Increasing concentrations of unlabeled N-β2GP1 competed for the binding of both $^{125}$I-labeled proteins, suggesting that both intact β2GP1 and N-β2GP1 bind to the same endothelial cell binding site.

To determine if N-β2GP1 could compete for the binding of intact β2GP1, both intact β2GP1 and N-β2GP1 were labeled with $^{125}$I (1 mCi/100 μg protein with iodogen), and added in the presence of increasing concentrations of unlabeled nicked protein to HUVECS endothelial cells in 24 well plates (100 μg/mL by dilution with unlabeled protein). The plates were washed after 1 hour, and uptake was determined by scintillation counting. As shown in FIG. 19, increasing concentrations of unlabeled N-β2GP1 competed for the binding of both $^{125}$I-labeled proteins, suggesting that both intact β2GP1 and N-β2GP1 bind to the same endothelial cell binding site. This finding is particularly important since it suggests that the nicked protein could displace intact β2GP1, regardless of its ability to bind lipid.

The following are additional experiments that will be used to test the hypothesis that N-β2GP1 induces apoptosis through a PS/annexin II-dependent mechanism. These experiments will directly determine the association of intact β2GP1 and N-β2GP1 with PS and with annexin II, as well as the association of PS directly to annexin in both cell free model membrane systems and in in vitro cultivated endothelial cells. First, resonance energy transfer (RET), as described in Lee et al., *Biochim. Biophys. Acta* 1509:475, 2000, incorporated herein by reference, can be used to detect multiple specific β2GP1 interactions with lipid in model membranes. These experiments can be used to specifically test the association of intact β2GP1 and N-β2GP1 with PS and with annexin II, and the concomitant formation of PS/β2GP1 and PS/annexin II complexes, respectively.

Briefly, phosphatidylcholine vesicles containing increasing amounts of NBD-labeled PS or control NBD-labeled PC (the energy donors) will be generated by sonication or ethanol injection. The interaction of the labeled PS will then be monitored by incubating the vesicles with rhodamine-labeled intact β2GP1 and N-β2GP1. The kinetics of the interaction will then be monitored in real time. Similar experiments will be done to monitor the ability of the NBD-lipid to directly associate with rhodamine labeled annexin II tetramers intercalated into the vesicle membrane (Raynor et al., *Biochemistry* 38:5089–5095, 1999; Singh and Liu, *Arch. Biochem. Biophys.* 381:235–240, 2000; incorporated herein by reference) in the presence of intact β2GP1 and N-β2GP1.

Ellipsometric measurements of protein adsorption to lipid bilayers can also be used determine dissociation constants for annexin II to immobilized intact β2GP1 and N-β2GP1, essentially as previously described for annexin V (Balasubramanian et al., *Biochemistry* 40:8672–8676, 2001, incorporated herein by reference). The role of lipid will also be determined by depositing planar lipid bilayers on silicon slides by immersion for 5 minutes in a stirred suspension of sonicated vesicles in Tris buffer containing appropriate concentrations of PS. Protein adsorption to the lipid bilayers will be assessed using β2GP1, N-β2GP1, and annexin II alone. Additive protein adsorptions can also be determined.

The binding of PS to targets in the endothelial cell membrane will also be assessed using iodinated photoactivatable lipid analogs as disclosed in Schroit et al., *Biochemistry* 26:1812–1819, 1987; Schroit et al., *Biochemistry* 29:10303–10306, 1990; Connor et al., *J. Biol. Chem.* 267: 19412–19417, 1992; and Connor and Schroit, *Biochemistry* 28:9680–9685, 1989, incorporated herein by reference. $^{125}$I-labeled-$N_3$-PS and control $^{125}$I-labeled-$N_3$-PC can be exchanged into endothelial cells at 4° C. β2GP1 and N-β2GP1 will be incubated with the cells for 30 minutes. The cells will then be photolysed, solubilized, and analyzed by SDS-PAGE. Proteins labeled with lipid probes will be detected by autoradiograhy and identified by molecular weight, sequence analysis, and western blotting to suspect target ligands.

EXAMPLE 10

Therapeutic Potential of β2GP1

Additional experiments may be performed to determine optimal route, dosage, and frequency of β2GP1 administration for maximal inhibition of tumor growth. Additionally, the minimal effective structural unit of β2GP1 identified in the in vitro assays described above (smallest recombinant domain-deleted fragment) can be tested for efficacy. One experimental system that models colon cancer is described as follows: mice will be anesthetized, washed, and a left-center subcostal incision will be made to expose the spleen. The spleen is lifted onto sterile gauze just outside of the wound and 0.05 ml of the cell suspension ($10^6$ cultured KM12L4a) will be injected into the parenchyma. The incision will be closed in one layer with surgical clips. The mice are randomized into treatment groups (10 mice/group) on about day 7. Therapy will consist of either 5-fluorouracil alone (50 mg/kg, 3×/week for 4 weeks); gemeitabine (125 mg/kg, twice weekly for 4 weeks), and β2GP1 and N-β2GP1 alone, or in combination with the chemotherapeutic agents. When mice become symptomatic of liver tumor burden (ascites, palpable tumor, posture, body weight), they will be sacrificed and the spleens, livers, and adjacent lymph nodes will be removed for determination of tumor burden and for immunohistochemistry.

Another experimental model that may be used is primary and metastatic renal cell carcinoma of human cancer in nude mice. In this protocol, nude mice are washed with betadine and a left subcostal incision is made to expose the left kidney. A 30-gauge needle is inserted from the lower pole to just below the renal subcapsule on the superior pole of the kidney. A 0.05 ml cell suspension ($10^6$ cultured SN12pm6 cells) is injected, resulting in a subcapsular bleb. The incision is closed in one layer with wound clips. Nephrectomy of the injected kidney is performed on about day 30. At the time of nephrectomy, an incision parallel to the original is made to expose the tumorous left kidney, the kidney is removed by ligature below the organ pedicle, and the wound is closed with clips. This protocol results in a high incidence of spontaneous lung metastasis of moderate tumor burden. Some groups of mice (10 mice/group) will be treated for the growth of primary tumor with intact β2GP1, N-β2GP1, or Taxol, 100 µg/dose, 1×/week, for 4 weeks, or a combination thereof. The therapeutic efficacy will be determined by weight of the primary tumors (kidneys). Other groups of mice will be treated after nephrectomy to evaluate the effects of single agent or combination therapy on the development of spontaneous lung metastasis that develop about 3–4 weeks post-nephrectomy. The lungs of mice will be harvested and the number and size of individual lung tumor nodules determined.

The model described above for human renal cell carcinoma can also be evaluated in a syngeneic murine model of renal adenocarcinoma (RENCA) in Balb/c mice. The primary tumors are injected as described above ($10^5$ cultured RENCA cells) and nephrectomy occurs on about day 14. The lungs of mice will be harvested on about day 35 to determine the extent of spontaneous lung metastasis.

In another model, the effect of β2GP1 and N-β2GP1 on subcutaneous growth of A237 human melanoma cells in nude mice can be assessed. In this protocol, nude mice will receive a subcutaneous injection of $10^6$ cultured A375 cells on day 0 and therapy will begin when the tumors are about 2–4 mm in diameter. Treatment groups (10 mice/group) are randomized to receive either doxorubicin (10 mg/kg, 1× week for two weeks), β2GP1, N-β2GP1, or a combination thereof. Tumor growth can be assayed by two perpendicular measurements of tumor diameter (estimated tumor volume is a×$b^2$/2, where a and b are the long and short diameters, respectively).

In yet another model, the effect of β2GP1 and N-β2GP1 on a model of experimental lung metastasis of B16 melanoma in syngeneic C57BL/6 mice can be determined. In this protocol, mice receive an intravenous injection of 40,000 cultured B16F10 cells on day 0 and therapy begins on about day 4. Using 10 mice/group, mice receive either doxorubicin (10 mg/kg, 1×/week for two weeks), β2GP1, N-β2GP1, or a combination thereof. On day 21, mice are sacrificed and the number of individual lung tumor nodules are determined. Necropsy of mice will determine the extent of other organ metastases and harvest of tissue for immunohistochemistry for the determination of blood vessel cell density and cellular apoptosis.

All of the compositions and methods disclosed and claimed herein can be made and executed without undue experimentation in light of the present disclosure. While the compositions and methods of this invention have been described in terms of preferred embodiments, it will be apparent to those of skill in the art that variations maybe applied to the compositions and/or methods and in the steps or in the sequence of steps of the methods described herein without departing from the concept, spirit and scope of the invention. More specifically, it will be apparent that certain agents that are chemically or physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method of inhibiting angiogenesis and/or angioectasia within a tissue comprising administering an effective amount of N-β2GP1 to cells associated with the tissue, wherein the amount is sufficient to inhibit angiogenesis and/or angioectasia within the tissue.

2. The method of claim 1, wherein angiogenesis is inhibited within the tissue.

3. The method of claim 1, wherein angioectasia is inhibited within the tissue.

4. The method of claim 1, wherein the N-β2GP1 is substantially pure N-β2GP1.

5. The method of claim 1, wherein the N-β2GP1 is administered to the cells by exposing a composition comprising N-β2GP1 polypeptide to the cells.

6. The method of claim 1, wherein the cells associated with the tissue are endothelial cells.

7. The method of claim 6, wherein the endothelial cells are selected from the group consisting of vascular endothelial cells, pulmonary endothelial cells, heart endothelial cells, gastrointestinal endothelial cells, brain endothelial cells, lymphatic endothelial cells, genital-urinary endothelial cells, skin endothelial cells, bone endothelial cells, muscle endothelial cells, breast endothelial cells, retinal endothelial cells, endocrine endothelial cells, central nervous system endothelial cells, hepatic endothelial cells, and umbilical cord endothelial cells.

8. The method of claim 1, wherein the tissue is a tumor.

9. The method of claim 8, further comprising inhibiting neovascularization into the tumor.

10. The method of claim 1, further comprising administering an antiangiogenic agent to the cells in conjunction with N-β2GP1.

11. The method of claim 10, wherein the antiangiogenic agent is selected from the group consisting of angiostatin, endostatin, trastuzumab, thrombospondin, IFN-α, TIMP-1, PF4, fumagiulin, and mixtures thereof.

12. A method of inhibiting angiogenesis and/or angioectasia within a neoplasm comprising administering an effective amount of N-β2GP1 to the neoplasm, wherein the amount is sufficient to inhibit angiogenesis and/or angioectasia within the neoplasm.

13. The method of claim 12, wherein angiogenesis is inhibited within the neoplasm.

14. The method of claim 12, wherein angioectasia is inhibited within the neoplasm.

15. The method of claim 12, wherein the N-β2GP1 is substantially pure N-β2GP1.

16. The method of claim 12, further comprising inhibiting metastasis of the neoplasm.

17. The method of claim 12, wherein the neoplasm is a tumor.

18. The method of claim 17, further comprising inhibiting neovascularization into the tumor.

19. The method of claim 12, further comprising administering an antiangiogenic agent to the neoplasm in conjunction with N-β2GP1.

20. The method of claim 19, wherein the antiangiogenic agent is selected from the group consisting of angiostatin, endostatin, trastuzumab, thrombospondin, IFN-α, TIMP-1, PF4, and fumagillin.

21. The method of claim 12, further comprising administering a therapeutic agent useful in the treatment of the neoplasm in conjunction with N-β2GP1.

22. The method of claim 21, wherein the therapeutic agent is selected from the group consisting of cisplatin, doxorubicin, paclitaxel, vincristine, and vinblastin.

23. A method of inhibiting angiogenesis and/or angioectasia at a tumor site in a subject comprising administering an effective amount of N-β2GP1 to the subject, wherein the amount is sufficient to inhibit angiogenesis and/or angioectasia at the tumor site.

24. The method of claim 23, wherein angiogenesis is inhibited at the tumor site.

25. The method of claim 23, wherein angioectasia is inhibited at the tumor site.

26. The method of claim 23, wherein the subject is human.

27. The method of claim 23, wherein the N-β2GP1 is substantially pure N-β2GP1.

28. The method of claim 23, wherein the route of administration to the subject is oral, intravenous, intramuscular, intrathecal, intradermal, intraperitoneal, subcutaneous, intrapleural, intrauterine, rectal, vaginal, topical, intratumor, transdermal, or transmucosal.

29. The method of claim 23, wherein the tumor site is melanoma tissue, and the effective amount of N-β2GP1 is from about 50 to about 200 mg of N-β2GP1 administered topically.

30. The method of claim 23, wherein the tumor site is fibrosarcoma tissue, and the effective amount of N-β2GP1 is from about 200 to about 300 mg of N-β2GP1 administered intravenously.

31. The method of claim 23, wherein the tumor site is breast cancer tissue, and the effective amount of N-β2GP1 is from about 250 to about 400 mg of N-β2GP1 administered by direct injection.

32. The method of claim 23, wherein the tumor site is prostate cancer tissue, and the effective amount of N-β2GP1 is from about 150 to about 300 mg of N-β2GP1 administered by direct injection.

33. The method of claim 23, wherein the tumor site is colon cancer tissue, and the effective amount of N-β2GP1 is from about 50 to about 250 mg of N-β2GP1 administered intravenously.

34. A pharmaceutical composition comprising N-β2GP1 and a second antiangiogenic agent useful for the inhibition of angiogenesis and/or angioectasia.

35. The composition of claim 34, wherein the N-β2GP1 is substantially pure N-β2GP1.

36. The composition of claim 34, wherein the antiangiogenic agent is selected from the group consisting of angiostatin, endostatin, trastuzumab, thrombospondin, IFN-α, TIMP-1, PF4, and fumagillin.

37. A pharmaceutical composition comprising N-β2GP1 and a second therapeutic agent, wherein the second therapeutic agent is useful for the treatment of a neoplasm.

38. The composition of claim 37, wherein the N-β2GP1 is substantially pure N-β2GP1.

39. The composition of claim 37, wherein the therapeutic agent is selected from the group consisting of cisplatin, doxorubicin, paclitaxel, vincristine, and vinblastin.

40. A method of inhibiting endothelial cell proliferation comprising administering an effective amount of N-β2GP1 to the cells, wherein the amount is sufficient to inhibit endothelial cell proliferation.

41. The method of claim 40, wherein the N-β2GP1 is substantially pure N-β2GP1.

42. The method of claim 40, further comprising inhibiting endothelial cell migration.

43. The method of claim 40, further comprising inhibiting endothelial cell differentiation.

44. The method of claim 43, wherein the endothelial cells are inhibited from differentiating into tubular capillary structures.

* * * * *

UNITED STATES PATENT AND TRADEMARK OFFICE
CERTIFICATE OF CORRECTION

PATENT NO. : 7,329,642 B2 Page 1 of 1
APPLICATION NO. : 10/406158
DATED : February 12, 2008
INVENTOR(S) : Schroit et al.

It is certified that error appears in the above-identified patent and that said Letters Patent is hereby corrected as shown below:

Title Pg. Item (54) Title & Col. 1, Line 1, delete the word "β-2-GLYCOPROTEIN", and insert the word --β-2-GLYCOPROTEIN 1--.

Title Pg. Item (73), insert the word --The-- before the word "University".

Title Pg. In the References Cited Item (56), under the heading "U.S. PATENT DOCUMENTS", delete "6,593,291 B1" and insert --6,593,291 B1 *--.

Title Pg. In the References Cited Item (56), under the heading "FOREIGN PATENT DOCUMENTS", delete "WO 01/027079" and insert --WO 01/027079 *--.

Column 58, line 46, for the claim reference numeral 11, delete "fumagiulin" and insert --fumagillin--.

Signed and Sealed this

Seventeenth Day of June, 2008

JON W. DUDAS
*Director of the United States Patent and Trademark Office*

SEQUENCE LISTING

<160> NUMBER OF SEQ ID NOS: 1

<210> SEQ ID NO 1
<211> LENGTH: 326
<212> TYPE: PRT
<213> ORGANISM: Homo sapiens

<400> SEQUENCE: 1

```
Gly Arg Thr Cys Pro Lys Pro Asp Asp Leu Pro Phe Ser Thr Val Val
1               5                   10                  15

Pro Leu Lys Thr Phe Tyr Glu Pro Gly Glu Glu Ile Thr Tyr Ser Cys
            20                  25                  30

Lys Pro Gly Tyr Val Ser Arg Gly Gly Met Arg Lys Phe Ile Cys Pro
        35                  40                  45

Leu Thr Gly Leu Trp Pro Ile Asn Thr Leu Lys Cys Thr Pro Arg Val
    50                  55                  60

Cys Pro Phe Ala Gly Ile Leu Glu Asn Gly Ala Val Arg Tyr Thr Thr
65                  70                  75                  80

Phe Glu Tyr Pro Asn Thr Ile Ser Phe Ser Cys Asn Thr Gly Phe Tyr
                85                  90                  95

Leu Asn Gly Ala Asp Ser Ala Lys Cys Thr Glu Glu Gly Lys Trp Ser
            100                 105                 110
```

```
Pro Glu Leu Pro Val Cys Ala Pro Ile Ile Cys Pro Pro Pro Ser Ile
        115             120             125

Pro Thr Phe Ala Thr Leu Arg Val Tyr Lys Pro Ser Ala Gly Asn Asn
        130             135             140

Ser Leu Tyr Arg Asp Thr Ala Val Phe Glu Cys Leu Pro Gln His Ala
145             150             155             160

Met Phe Gly Asn Asp Thr Ile Thr Cys Thr Thr His Gly Asn Trp Thr
                165             170             175

Lys Leu Pro Glu Cys Arg Glu Val Lys Cys Pro Phe Pro Ser Arg Pro
        180             185             190

Asp Asn Gly Phe Val Asn Tyr Pro Ala Lys Pro Thr Leu Tyr Tyr Lys
        195             200             205

Asp Lys Ala Thr Phe Gly Cys His Asp Gly Tyr Ser Leu Asp Gly Pro
        210             215             220

Glu Glu Ile Glu Cys Thr Lys Leu Gly Asn Trp Ser Ala Met Pro Ser
225             230             235             240

Cys Lys Ala Ser Cys Lys Val Pro Val Lys Lys Ala Thr Val Val Tyr
        245             250             255

Gln Gly Glu Arg Val Lys Ile Gln Glu Lys Phe Lys Asn Gly Met Leu
        260             265             270

His Gly Asp Lys Val Ser Phe Phe Cys Lys Asn Lys Glu Lys Lys Cys
        275             280             285

Ser Tyr Thr Glu Asp Ala Gln Cys Ile Asp Gly Thr Ile Glu Val Pro
        290             295             300

Lys Cys Phe Lys Glu His Ser Ser Leu Ala Phe Trp Lys Thr Asp Ala
305             310             315             320

Ser Asp Val Lys Pro Cys
                325
```